US012611438B2

(12) United States Patent
Kim et al.

(10) Patent No.: US 12,611,438 B2
(45) Date of Patent: *Apr. 28, 2026

(54) ANTIVIRAL COMPOSITION COMPRISING A NUCLEOLIN-BINDING PEPTIDE

(71) Applicant: ANYGEN CO., LTD., Gwangju (KR)

(72) Inventors: Jaeil Kim, Gwangju (KR); Jae-Ha Ryu, Gwangju (KR); Kyoung-Oh Cho, Gwangju (KR)

(73) Assignee: ANYGEN CO., LTD., Gwangju (KR)

( * ) Notice: Subject to any disclaimer, the term of this patent is extended or adjusted under 35 U.S.C. 154(b) by 468 days.

This patent is subject to a terminal disclaimer.

(21) Appl. No.: 18/549,549

(22) PCT Filed: May 18, 2022

(86) PCT No.: PCT/KR2022/007131
§ 371 (c)(1),
(2) Date: Sep. 7, 2023

(87) PCT Pub. No.: WO2022/245136
PCT Pub. Date: Nov. 24, 2022

(65) Prior Publication Data
US 2024/0299487 A1 Sep. 12, 2024

(30) Foreign Application Priority Data

May 18, 2021 (KR) ........................ 10-2021-0064140

(51) Int. Cl.
*A61K 38/08* (2019.01)
*A61K 47/60* (2017.01)
(Continued)

(52) U.S. Cl.
CPC .............. *A61K 38/08* (2013.01); *A61K 47/60* (2017.08); *A61K 47/64* (2017.08); *A61P 31/14* (2018.01); *A61P 31/16* (2018.01)

(58) Field of Classification Search
None
See application file for complete search history.

(56) References Cited

U.S. PATENT DOCUMENTS

2018/0042843 A1 2/2018 Blum et al.

FOREIGN PATENT DOCUMENTS

KR 101169030 B1 7/2012
WO 2011031477 A2 3/2011
WO 2021234550 A1 11/2021

OTHER PUBLICATIONS

Office Action issued on Sep. 19, 2024 for Australian Patent Application 2022276988.

(Continued)

*Primary Examiner* — Kevin S Orwig
(74) *Attorney, Agent, or Firm* — HULTQUIST, PLLC; Steven J. Hultquist

(57) ABSTRACT

The present invention relates to an antiviral use of a novel peptide binding specifically to nucleolin and, more specifically, to: an antiviral composition comprising a peptide represented by a specific amino acid sequence; an antiviral composition comprising a fusion peptide in which the peptide and a cell-penetrating peptide are coupled to each other; a composition comprising the aforementioned compositions for preventing or treating a viral infection; and a health functional food composition for prevention or alleviation of a viral infection. In the present invention, a AGM peptide ligand and mutants thereof were found to inhibit viral proliferation and replication (in vitro and in vivo), as screened by an MAP synthesis method and an OBOC combination method. Therefore, NCL-targeting AGM can find advantageous applications in antiviral uses.

19 Claims, 29 Drawing Sheets
Specification includes a Sequence Listing.

AGM-330m
Monomeric AGM-330

AGM-330d
Dimeric AGM-330

AGM-330t
Tetrameric AGM-330

(51) Int. Cl.

| | |
|---|---|
| *A61K 47/64* | (2017.01) |
| *A61P 31/14* | (2006.01) |
| *A61P 31/16* | (2006.01) |
| *C07K 7/06* | (2006.01) |

(56) References Cited

OTHER PUBLICATIONS

Office Action issued on Sep. 27, 2024 for Japanese Patent Application 2023-557463.

English Translation of Office Action issued on Sep. 27, 2024 for Japanese Patent Application 2023-557463.

Niki, S., "Intracellular delivery of proteins and drugs using membrane-permeable peptides", Medchem News, 2014, pp. 20-24, No. 1.

English Translation of Niki, S., "Intracellular delivery of proteins and drugs using membrane-permeable peptides", Medchem News, 2014, pp. 20-24, No. 1.

Abdelmohsen, K., et al., "RNA-binding protein nucleolin in disease", RNA Biology, 2012, pp. 799-808, vol. 9, No. 6, Publisher: www.landesbioscience.com.

Gupta, V., et al., "Protein PEGylation for cancer therapy: bench to bedside", Journal of Cell Communication and Signaling, 2018, pp. 319-330; https://doi.org/10.1007/s12079-018-0492-0, vol. 13, Publisher: Springer.

Jia, W., et al., "New perspectives of physiological and pathological functions of nucleolin (NCL)", Life Sciences, 2017, http://dx.doi.org/10/1016/j.lfs.2017.07.025, vol. 186, Publisher: Elsevier.

Kim, J-H., et al., "A novel nucleolin-binding peptide for Cancer Theranostics", Theranostics, 2020, pp. 9153-9171, vol. 10, No. 20, Publisher: Ivyspring.

Lam, K.S., et al., "The One-Bead-One-Compound: Combinatorial Library Method", Chem Rev., 1997, pp. 411-448, vol. 97, Publisher: American Chemical Society.

Mcgregor, D.P., "Discovering and improving novel peptide therapeutics", Current Opinion in Pharmacology, 2008, pp. 616-619, vol. 8, Publisher: www.sciencedirect.com.

Mcguire, M.J., et al., "Identification and Characterization of a Suite of Tumor Targeting Peptides for Non-Small Cell Lung Cancer", Scientific Reports, 2014, DOI:10.1038/srep04480, vol. 4, No. 4480.

Milkawa, M., et al., "Novel Peptide ligands for integrin 41 overexpressed in cancer cells", Molecular Cancer Therapeutics, 2004, pp. 1329-1334, vol. 3, No. 10.

Moreno, A., et al., "Anti-PEG Antibodies Inhibit the Anticoagulant Activity of PEGylated Aptamers", Cell Chemical Biology, 2019, pp. 634-644, vol. 26, Publisher: CellPress.

Mori, T., "Cancer-Specific Ligands Identified from Screening of Peptide-Display Libraries", Current Pharmaceutical Design, 2004, pp. 2335-2343, vol. 10, Publisher: Bentham Science Publishers Ltd.

Palmieri, D., et al., "Human anti-nucleolin recombinant immunoagent for cancer therapy", PNAS, 2015, pp. 9418-9423; www.pnas.org/cgi/doi/10.1073/pnas.1507087112, vol. 112, No. 30, Publisher: CrossMark.

Pauletti, G.M., et al., "Improvement of oral peptide bioavailability: Peptidomimetics and prodrug strategies", Advanced Drug Delivery Reviews, 1997, pp. 235-256, vol. 27, Publisher: Elsevier.

Shen, N., et al., "A nucleolin-DNMT1 regulatory axis in acute myeloid leukemogenesis", Oncotarget, 2014, pp. 5494-5509, vol. 5, No. 14, Publisher: www.impactjournals.com/oncotarget/.

Wan, X., et al., "Effect of protein immunogenicity and PEG size and branching on the anti-PEG immune response to PEGylated proteins", Process Biochemistry, 2016, pp. 183-191; http://dx.doi.org/10.1016/j.procbio.2016.09.029, vol. 52, Publisher: Elsevier.

Search Report issued on Mar. 25, 2025 for European Patent Application No. 22804990.

Guidotti, G., et al., "Cell-Penetrating Peptides: From Basic Research to Clinics", Trends in Pharmacological Sciences, 2017, doi.org/10.1016/j.tips.2017.01.003, vol. 38, No. 4, Publisher: Elsevier.

Joshi, V.G., et al., "Multiple antigenic peptide (MAP): a synthetic peptide dendrimer for diagnostic, antiviral and vaccine strategies for emerging and re-emerging viral diseases", Indian J. Virol., 2013, pp. 312-320, vol. 24, No. 3, Publisher: Indian Virology Society.

FIG. 1

FIG. 3
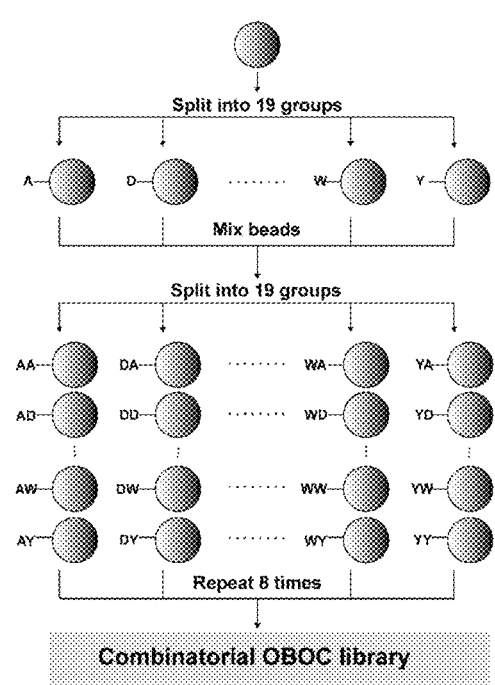
1. OBOC library synthesis
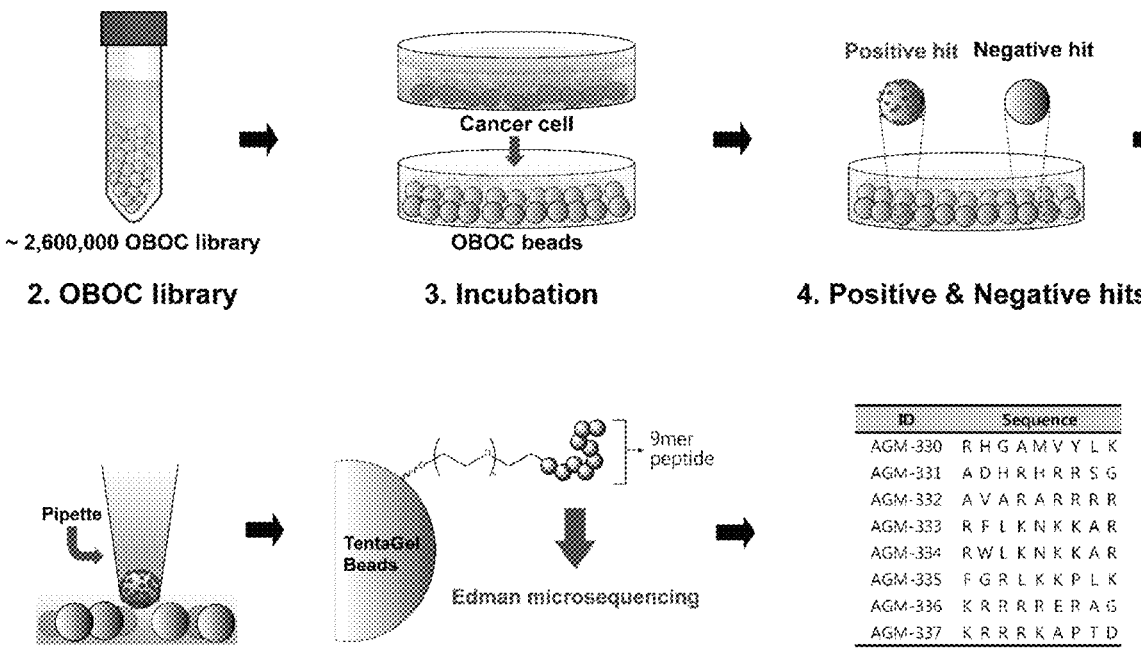
~ 2,600,000 OBOC library
2. OBOC library
3. Incubation
4. Positive & Negative hits
5. Collect positive hits
6. Automatic edman microsequencing
7. Sequence of peptide candidates

| Parameters | AGM-330m | AGM-330d | AGM-330t |
|---|---|---|---|
| $T_{1/2}$ (h) | 0.42 ± 0.33 | 1.82 ± 0.36 | 9.43 ± 1.21 |
| $T_{max}$ (h) | 0.167 | 0.167 | 0.167 |
| $C_{max}$ (µg/ml) | 1.27 ± 0.12 | 1.71 ± 0.11 | 1.875 ± 0.67 |
| AUC (µg/h/ml) | 0.64 ± 0.09 | 1.77 ± 0.12 | 21.42 ± 0.81 |

$T_{1/2}$: The distribution half-time; $T_{max}$: Time to reach maximum plasma concentration; $C_{max}$: Maximum plasma concentration; AUC: Area under the plasma concentration-time curve

FIG. 6

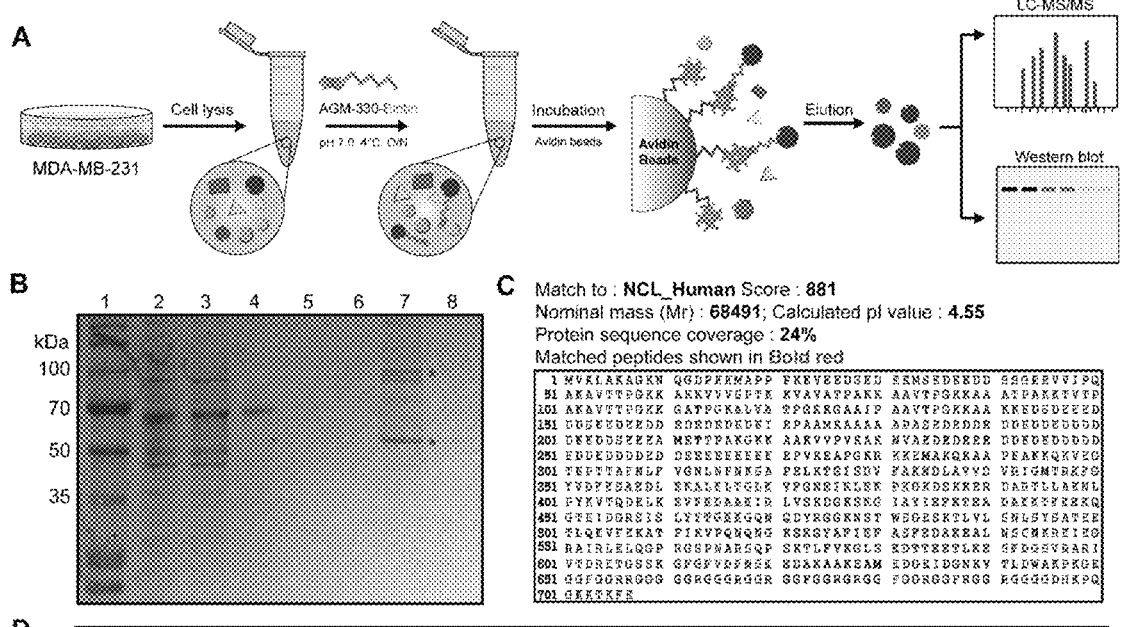

C

Match to : NCL_Human Score : 881
Nominal mass (Mr) : 68491; Calculated pI value : 4.55
Protein sequence coverage : 24%
Matched peptides shown in Bold red

D

| Gene name | NM number | Protein identification | Confidence score[a] | Peptide count | Mass |
|---|---|---|---|---|---|
| NCL | NM_005381 | Nucleolin | 881 | 22 | 68491 |
| ACTN4 | NM_004924 | Actinin alpha 4 | 155 | 12 | 105353 |
| ACTN1 | NM_001102 | Actinin alpha 1 | 127 | 6 | 103666 |
| HSP90B1 | NM_003299 | Heat shock protein 90 beta family member 1 | 110 | 3 | 90362 |
| VCP | NM_007126 | Valosin containing protein | 83 | 5 | 90019 |
| COPG1 | NM_016128 | Coatomer protein complex subunit gamma 1 | 65 | 2 | 79201 |

[a] Confidence score obtained from Mascot.

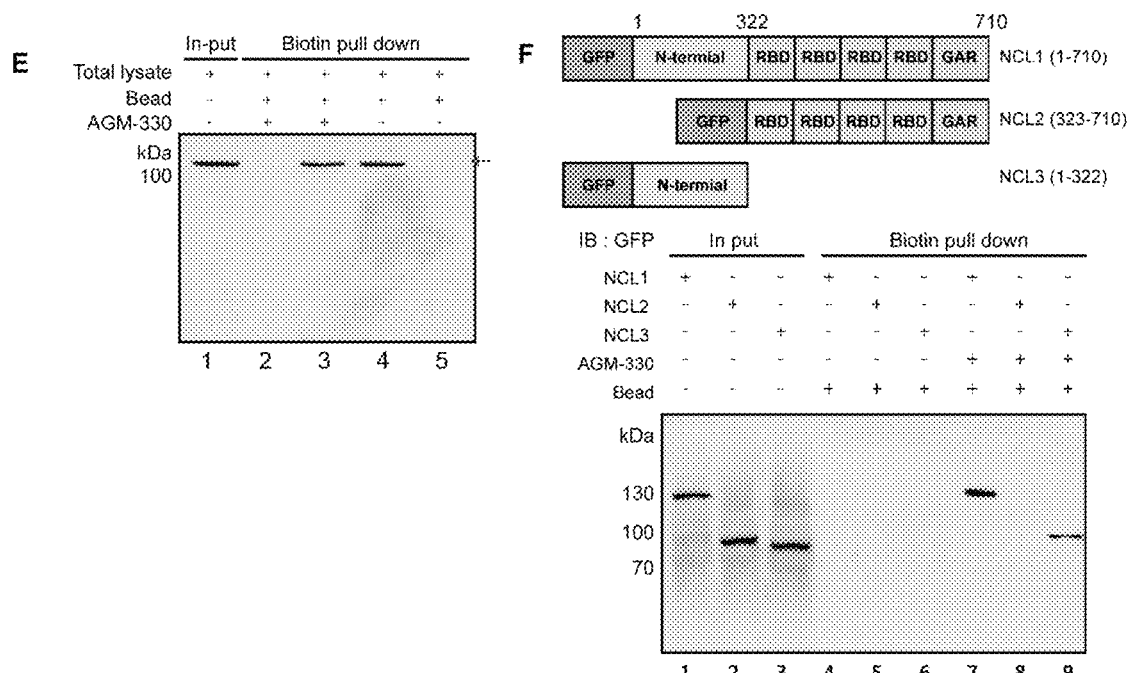

1 : Protein marker

2 : Purified nucleolin

3 : Flow through

4 ~ 6 : Washing

7 ~ 9 : Elution

AGM-330t

Cell surface nucleolin
targeting ligand

Maleimide-mCPP

Maleimide
conjugated CPP

AGM-330t-mCPP

Intracellular nucleolin
targeting ligand pH 7.0~7.5

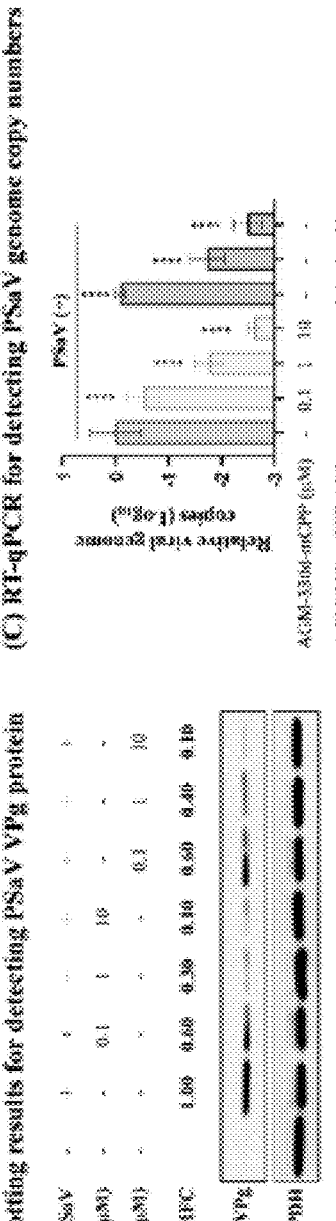
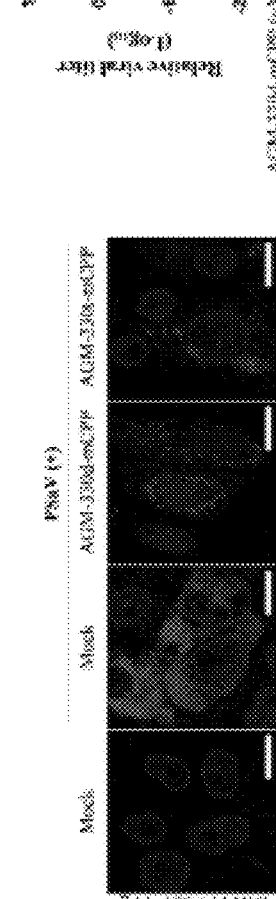
FIG. 16

Hamster Lung Structure

| Lung lobe | % of lung weight (%) |
|-----------|---------------------|
| ① | 40 |
| ② | 10 |
| ③ | 5 |
| ④ | 30 |
| ⑤ | 15 |
| Total area % | 100 |

Macroscopic pneumonia lesion improvement rate (%) =
[pneumonia induction rate in test group / pneumonia induction rate in virus-infected group] X 100

Macroscopic lesion improvement rate (%)

| | NC | VC | AGM 380D-0.2 MPK | AGM 380D-2 MPK | AGM 380D-6 MPK |
|---|---|---|---|---|---|
| • Macroscopic pneumonia lesion improvement rate (%) | 100 | 1 | 6.4 | 14.0 | 41.6 |

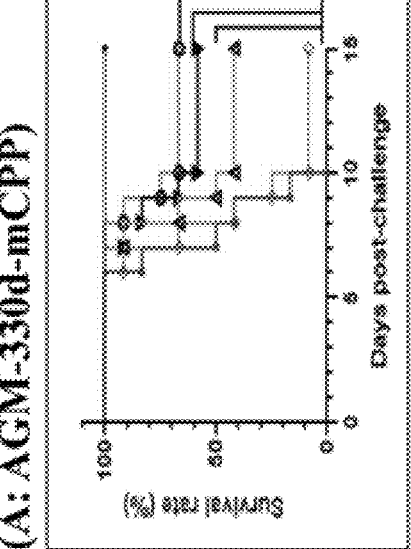
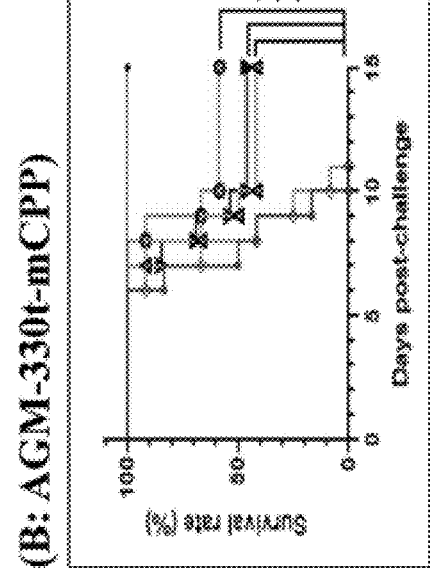
FIG. 27

FIG. 28

FIG. 29
A. Western blot
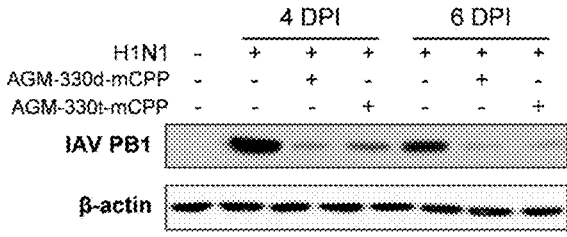
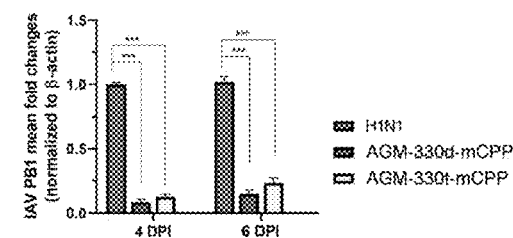
B. qPCR
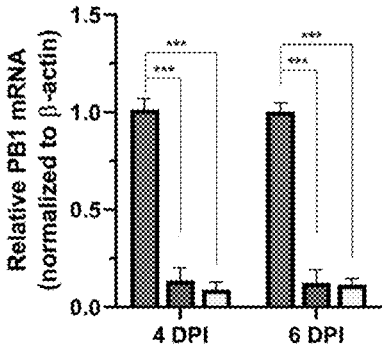
C. Viral titer
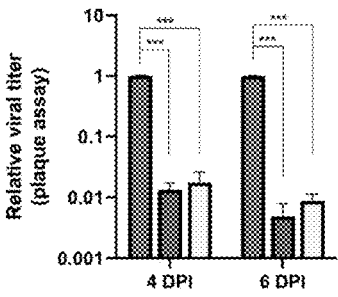
DPI: Days post infection

ANTIVIRAL COMPOSITION COMPRISING A NUCLEOLIN-BINDING PEPTIDE

CROSS-REFERENCE TO RELATED APPLICATIONS

This is a U.S. national phase under 35 U.S.C. § 371 of International Patent Application No. PCT/KR2022/007131 filed May 18, 2022, which in turn claims priority under 35 U.S.C. §119 of Korean Patent Application No. 10-2021-0064140 filed May 18, 2021. The disclosures of all such applications are hereby incorporated herein by reference in their respective entireties, for all purposes.

REFERENCE TO SEQUENCE LISTING

This application includes an electronically submitted sequence listing in .txt format. The .txt file contains a sequence listing entitled "696_UpdatedSeqListing_ST25.txt" created on Feb. 10, 2026 and is 25, 315 bytes in size. The sequence listing contained in this .txt file is part of the specification and is hereby incorporated by reference herein in its entirety.

TECHNICAL FIELD

The present invention relates to antiviral use of a novel peptide that specifically binds to nucleolin, and more specifically, to an antiviral composition comprising a peptide represented by a specific amino acid sequence, an antiviral composition comprising a fusion peptide in which the peptide is fused with a cell-penetrating peptide, a composition for preventing or treating viral infections comprising the compositions, and a health functional food composition for preventing or ameliorating viral infections.

BACKGROUND ART

As an alternative to classical diagnostic and treatment methods, cancer-specific peptides may be used to increase therapeutic efficiency and reduce side effects associated with nanoparticles and antibody cancer therapies (Mori T. Curr Pharm Des. 2004; 10:2335-43). Peptide ligands have many advantages including easy large-scale synthesis, low immunogenicity, generation of non-toxic metabolites, and high in vivo biocompatibility (McGregor D P. Curr Opin Pharmacol. 2008; 8:616-9). Among many methods for developing peptides, a one-bead-one-compound (OBOC) combinatorial method is a powerful method for screening peptide ligands (Lam K S, et al. Chem Rev. 1997; 97:411-48). Peptide screening approaches based on OBOC combinatorial libraries have facilitated the discovery of novel peptide ligands for cellular targeting in cancer and other diseases (Mikawa M, et al. Mol Cancer Ther. 2004; 3:1329-34). Although a number of cancer-specific peptides have been isolated using in vitro OBOC combinatorial screening or other methods, several challenges remain. In particular, the major drawback of drugs using peptides is very short half-life due to very rapid cleavage by peptidases (Borchardt T R, et al. Adv Drug Deliv Rev. 1997; 27:235-56). The present inventors have attempted to overcome the problems by developing a dedicated approach to synthesize bioactive peptides in the dendrimeric form of a multiple-antigen peptide (MAP). Synthesis of monomeric peptides in the dendrimeric form increases stability due to acquired resistance to protease and peptidase activity (McGuire M J, et al. Sci Rep. 2014; 4:4480).

Accordingly, the present inventors conceived a series of peptide ligands called "AGM" or "AGM peptides" that specifically bind to human breast cancer and colorectal cancer cells by combining OBOC combinatorial screening with MAP synthesis. Furthermore, the present inventors identified that nucleolin (NCL) is a target protein of AGM through pull-down analysis and LC-MS/MS. NCL is the most abundant protein in the nucleolus. In the present invention, it was found that NCL expression was increased by viral infection using an anti-NCL antibody or the like and that when cells infected with various viruses including Coronavirus and influenza virus are treated with AGM peptides, the proliferation and replication of viruses are inhibited and antiviral efficacy is obtained. Based thereon, the present invention has been completed.

The information disclosed in this Background section is provided only for enhancement of understanding of the background of the present invention, and therefore it may not include information that forms the prior art that is already obvious to those skilled in the art.

SUMMARY OF THE INVENTION

It is an object of the present invention to provide an antiviral composition comprising a peptide that specifically binds to nucleolin (NCL).

It is another object of the present invention to provide an antiviral composition comprising a fusion peptide in which a peptide specifically binding to nucleolin (NCL) is fused with a cell-penetrating peptide (CPP).

It is another object of the present invention to provide a composition for preventing or treating viral infections comprising the antiviral compositions.

It is another object of the present invention to provide a method for preventing or treating viral infections comprising administering the antiviral composition to a subject.

It is another object of the present invention to provide the use of the antiviral composition for preventing or treating viral infections.

It is another object of the present invention to provide the use of the antiviral composition for preparing a drug for preventing or treating viral infections.

In accordance with one aspect of the present invention, the above and other objects can be accomplished by the provision of an antiviral composition comprising an AGM peptide specifically binding to nucleolin (NCL), wherein the AGM peptide comprises an amino acid sequence selected from the group consisting of:
(a) an amino acid sequence represented by any one of SEQ ID NOS: 1 to 8; and
(b) an amino acid sequence comprising at least one amino acid mutation selected from the following group in the amino acid sequence represented by SEQ ID NO: 1:
(i) substitution of the fifth methionine residue from the N-terminus;
(ii) substitution of the seventh tyrosine residue from the N-terminus; and
(iii) insertion of a leucine or lysine residue at the C-terminus.

In accordance with another aspect of the present invention, provided is an antiviral composition comprising an AGM peptide-CPP fusion peptide in which the AGM peptide specifically binding to nucleolin (NCL) is fused with a cell-penetrating peptide (CPP).

In accordance with another aspect of the present invention, provided is a composition for preventing or treating viral infections comprising the peptide, the fusion peptide or the antiviral composition.

In accordance with another aspect of the present invention, provided is a method for preventing or treating viral infections comprising administering the peptide, the fusion peptide or the antiviral composition to a subject.

In accordance with another aspect of the present invention, provided is the use of the peptide, the fusion peptide or the antiviral composition for preventing or treating viral infections.

In accordance with another aspect of the present invention, provided is the use of the peptide, the fusion peptide or the antiviral composition for preparing a drug for preventing or treating viral infections.

BRIEF DESCRIPTION OF DRAWINGS

Figure 1:
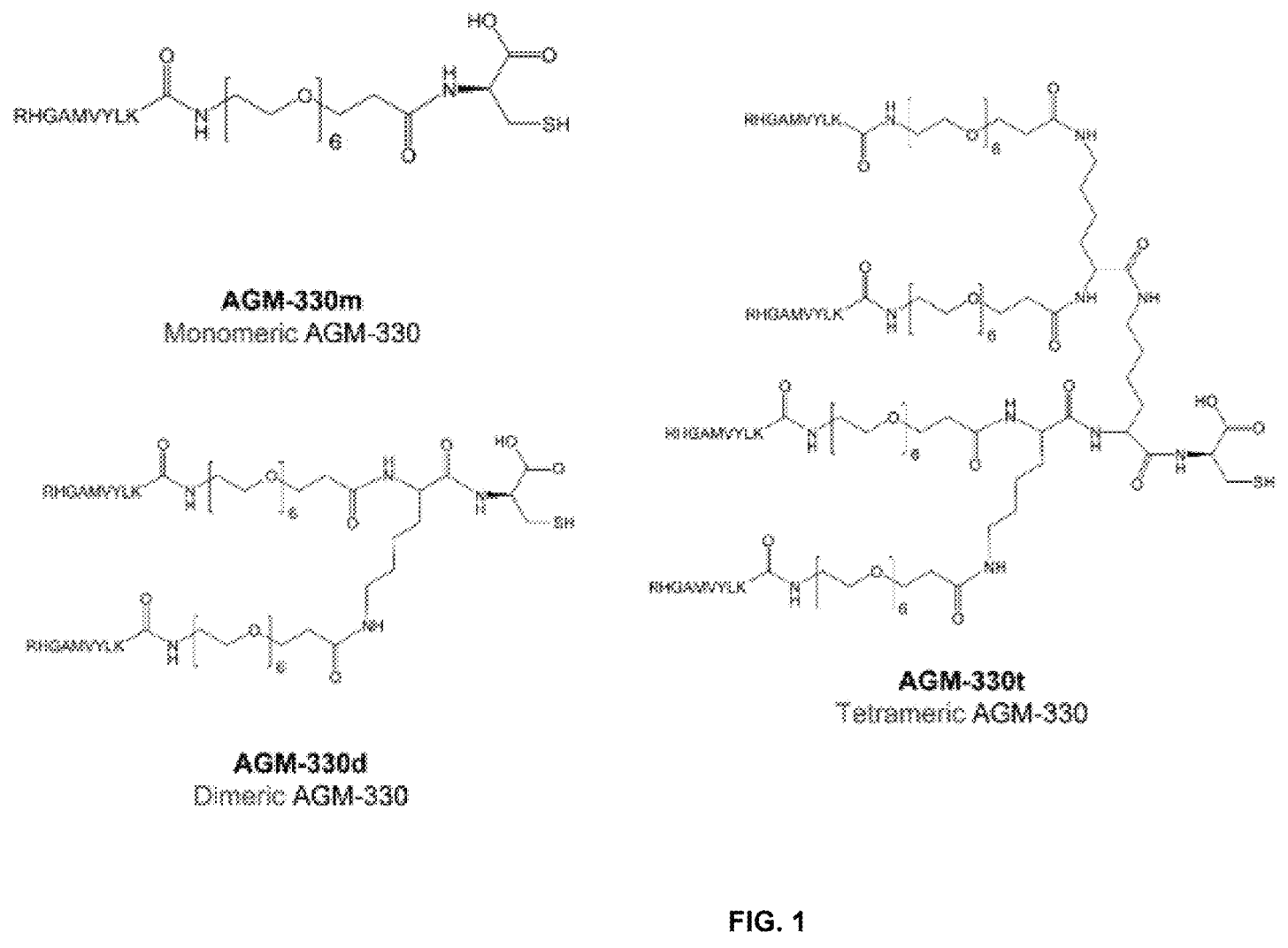

FIG. 1 is a diagram illustrating monomeric (AGM-330m), dimeric (AGM-330d), and tetrameric (AGM-330t) structures of a conjugate of AGM-330 and PEG according to the present invention, in which the monomer, dimer, and tetramer include pendant group RHGAMVYLK (SEQ ID NO: 1).

FIG. 3 is a schematic diagram illustrating peptide library synthesis and screening steps: 1, constructing an OBOC combinatorial library through split-mix synthesis; 2, synthesis of approximately ~2,600,000 libraries; 3, incubation of OBOC library along with cancer cells in a $CO_2$ incubator; 4, beads carrying ligands with affinity for cell surface molecules covered with cells; 5, pipetting the positive beads under an inverted microscope; 6, sequencing of positive beads by Edman microsequencing; 7, identification of cancer-specific peptide ligand candidates by OBOC combinatorial peptide library screening (RHGAMVYLK (SEQ ID NO: 1); ADHRHRRSG (SEQ ID NO: 2); AVARARRRR (SEQ ID NO: 3); RFLKNKKAR (SEQ ID NO: 4); RWLKNKKAR (SEQ ID NO: 5); FGRLKKPLK (SEQ ID NO: 6); KRRRRERAG (SEQ ID NO: 7); and KRRRKAPTD (SEQ ID NO: 8)).

FIG. 4 in A thereof shows the binding specificity of the peptide to cancer cell lines and normal cells (RHGAMVYLK (SEQ ID NO: 1); ADHRHRRSG (SEQ ID NO: 2); AVARARRRR (SEQ ID NO: 3); RFLKNKKAR (SEQ ID NO: 4); RWLKNKKAR (SEQ ID NO: 5); FGRLKKPLK (SEQ ID NO: 6); KRRRRERAG (SEQ ID NO: 7); and KRRRKAPTD (SEQ ID NO: 8)), and FIG. 4 in B thereof shows the results of whole-cell binding analysis showing the cell binding specificity of the selected 8 beads, wherein a plurality of breast and colorectal cancer cells and normal breast and colorectal cells were resuspended at $10^6$ cells/ml and incubated along with beads, all experiments were repeated three times, and the scale bar is 200 μm. FIG. 4 in C thereof shows the binding specificity determined by confocal imaging of immunofluorescence of FITC-labeled AGM-330, AGM-331 and AGM-332, nuclei were stained with DAP (blue), and scale bar is 50 μm. FIG. 4 in D thereof shows the binding specificity of AGM-330, wherein a

Figure 2:
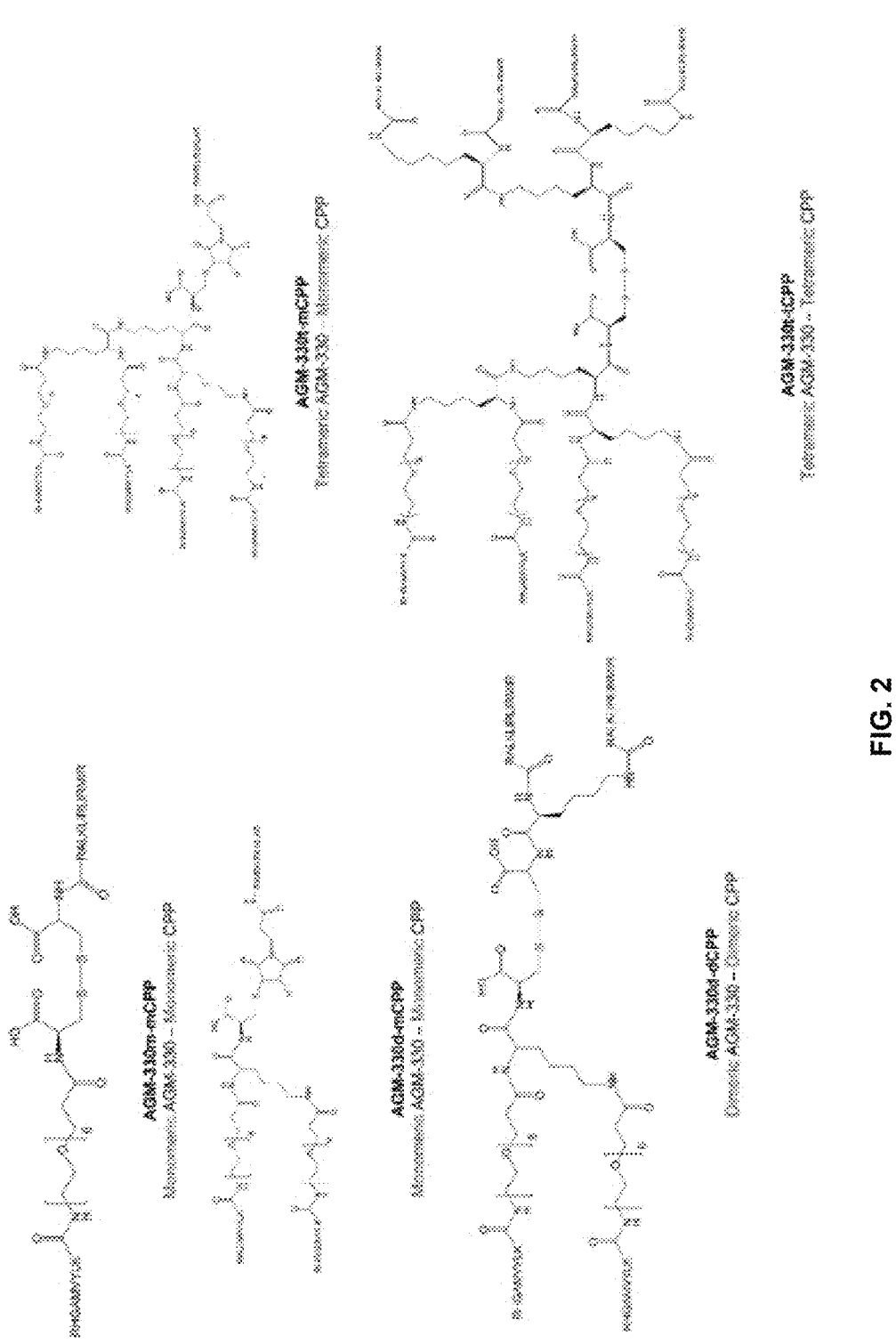
FIG. 2 illustrates the structure of an AGM-330-CPP fusion peptide in which an AGM-330-PEG conjugate is fused with a cell-penetrating peptide (CPP) according to the present invention, including pendant groups RHGAMVYLK (SEQ ID NO: 1), RALKLIRLIRMIR (SEQ ID NO: 83), and RIMRILRILKLAR (SEQ ID NO: 38).
Figure 4:
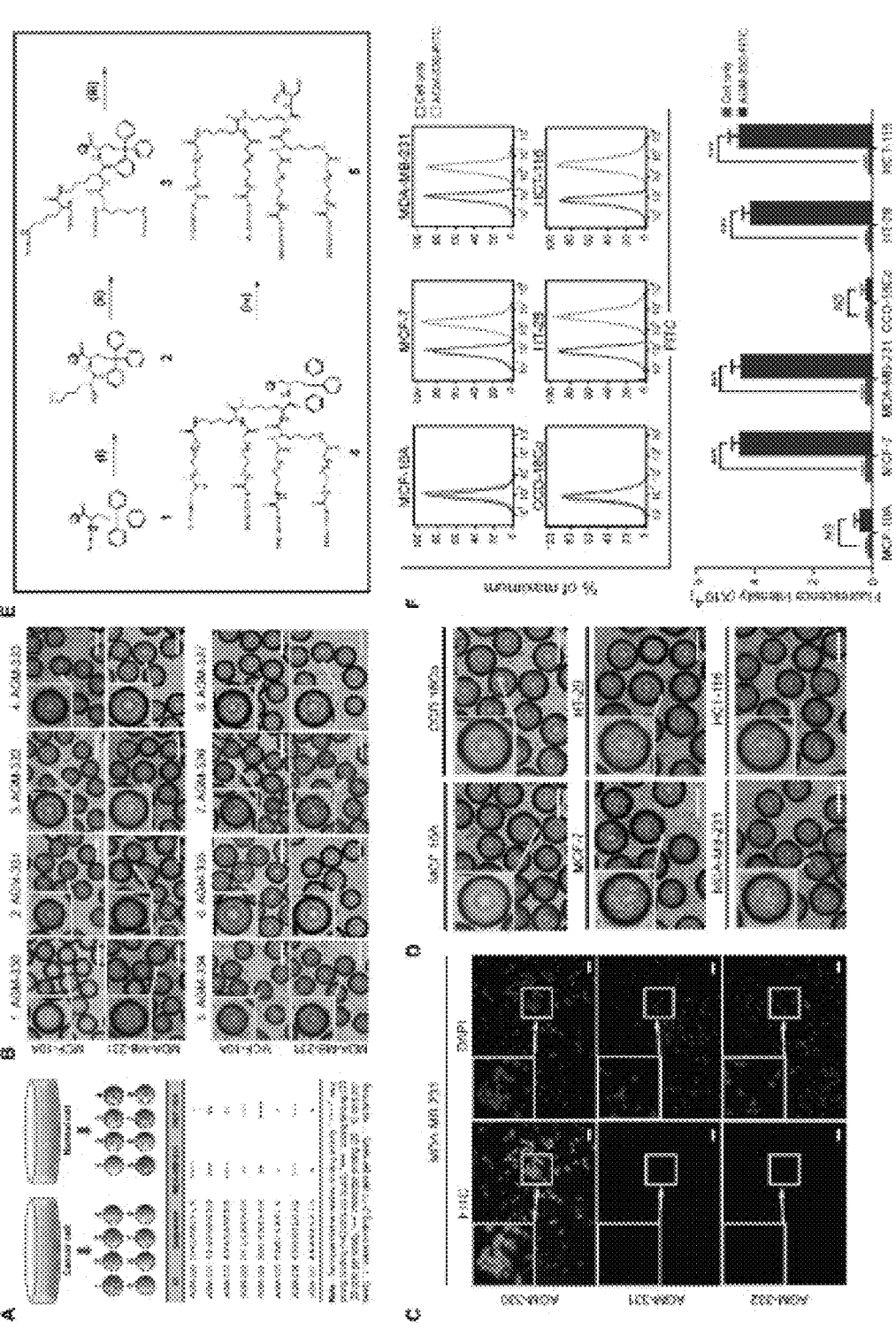
FIG. 4 shows screening of the OBOC library for cancer-specific ligands and MAP synthesis.

4 whole-cell binding assay was performed to determine cell binding of AGM-330 and the scale bar is 200 μm. FIG. 4 in E thereof shows the synthesis procedure of AGM-330, reagents and conditions of which are as follows: (i) Fmoc-Lys-(Fmoc)-OH, piperidine, DMF; (ii) Fmoc-Lys-(Fmoc)-OH, piperidine, DMF; (iii) RHGAMVYLK-OH, piperidine; (iv) piperidine, DMF. Fmoc=9-fluorenylmethoxycarbonyl, DMF=dimethylformamide. FIG. 4 in F thereof shows the result of FACS analysis showing the specificity of AGM-330 for cancer cells among a large number of breast cancer and colorectal cancer cells, and normal breast and colorectal cancer cells, the bar graph shows mean+SD, statistical analysis was performed by one-way ANOVA with Dunnett's multiple comparison, and *,  and * indicate P<0.05, P<0.01 and P<0.001, respectively.

Figure 5:
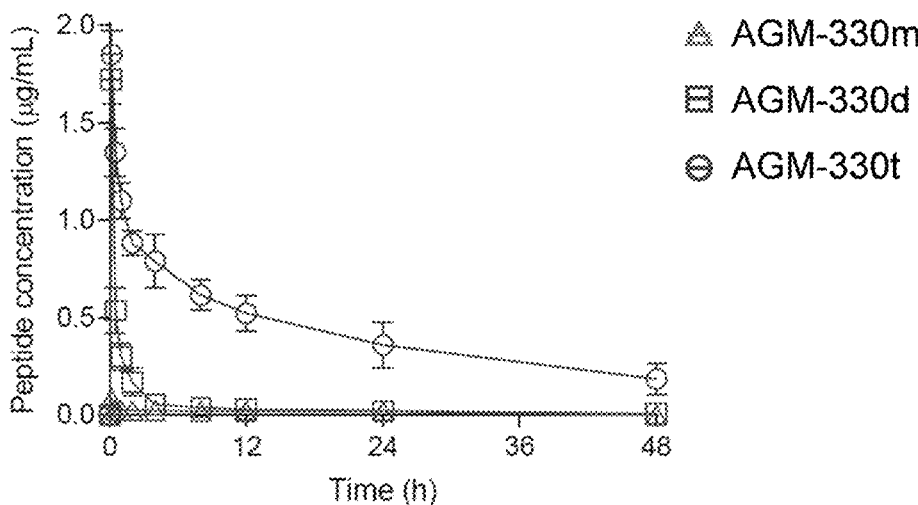

FIG. 5 shows the result of the test of peptide in vivo stability by AGM-330 (AGM-330m, AGM-330d, AGM-330t), wherein, after administering 2 mg/kg of AGM-330 to the tail vein of the mouse, blood was collected from the eye using a heparin-coated tube every 0, 0.167, 1, 2, 4, 6, 8, 12, 24 and 48 hours, the blood was allowed to clot at 4° C., and serum was collected by centrifugation at 5,000 rpm at 4° C. for 10 minutes, the peptide residue in serum was immediately immobilized on the ELISA plate by an anti-AGM-330 antibody, absorbance was measured at a wavelength of 450 nm using a VersaMax ELISA plate reader (Molecular Devices), and pharmacokinetics were analyzed with the phoenix WinNonlin 8.1 (Pharsight Corporation, Mountain View, CA, USA) program.

FIG. 6 shows the results of identification of the molecular target and characteristics of AGM-330.

FIG. 6 in A thereof is a schematic diagram illustrating biotin pull-down analysis, mass spectrometry, and Western blotting. FIG. 6 in B thereof shows results of Coomassie brilliant blue staining of proteins eluted from the affinity column after separation by 10% SDS-PAGE, wherein Lane 1: protein marker; Lane 2: total lysate before biotin pull-down assay; Lane 3: flow-through after incubation with AGM-330-biotin; Lane 4-6: bead washing fraction; Lane 7-8: elution of AGM-330 binding proteins, and * red star indicates that LC-MS/MS analysis was performed after protein bands were excised for lysis in the gel. FIG. 6 in C thereof shows the result of identification of NCL as an AGM-330 binding partner through a protein database search of peptides detected by MS, wherein the illustrated peptide sequence MVKLAKAGKNQGDPKKMAPPPKEVEED-SEDEEMSEDEEDDSSGEEVVIPQ AKAVTTPGK-KAKKVVVSPTKKVAVATPAKKAAVTPGKKAAAT-PAKKTVTP
AKAVTTPGKKGATPGKALVATPGKKGAAI-PAAVTPGKKAAKKEDSDEEED DDSEEDEEDDEDED-EDEDEIEPAAMKAAAAAPASEDEDDEDDED-DEDDDD
DEEDDSEEEAMETTPAKGKKAAKVVPVKAKNVAE-DEDEEEDDEDEDDDDD EDDEDDDDED-DEEEEEEEEEEEPVKEAPGKRKKEMAKQ-KAAPEAKKQKVEG
TEPTTAFNLFVGNLNFNKSAPELKTGISDVFAKND-LAVVDVRIGMTRKFG YVDFESAEDLEKA-LELTGLKVFGNEIKLEKPKGKDSKKERDARTL-LAKNL
PYKVTQDELKEVFEDAAEIRLVSKDGKSKGIAYIEFK-TEADAEKTFEEKQ GTEIDGRSISLYYT-GEKGQNQDYRGGKNSTWSGESKTLVLSNLSYSATEE
TLQEVFEKATFIKVPQNONGKSKG-YAFIEFASFEDAKEALNSCNKREIEG RAI-RLELQGPRGSPNARSQPSKTLFVKGLSEDTTEETL- KESFDGSVRARI
VTDRETGSSKGFGFVDFNSEEDAKAAKEAMED-
GEIDGNKVTLDWAKPKGE    GGFGGRRGGGGGRGG-
GRGGRGGFGGRGRGGFGGRGGFRG-
GRGGGGDHKPQ GKKTKFE is SEQ ID NO: 84. FIG. 6 in
D thereof shows a gene list obtained by LC-MS/MS analy-
sis, wherein the confidence score represents the mascot score
of the identified protein. FIG. 6 in E thereof shows the result
of immunoblotting analysis of proteins eluted by biotin
pull-down using an anti-NCL antibody and arrows indicate
the presence of NCL. FIG. 6 in F thereof shows the result of
analysis of the NCL domain binding to AGM-330, different
GFP-NCL constructs were transfected into HEK293T cells,
and AGM-330-biotin was added to NCL residues 1-710 and
1-322, or residues 323-710 bound with streptavidin beads,
and the protein on the beads was analyzed by immunoblot-
ting using an anti-GFP antibody.

Figure 7:
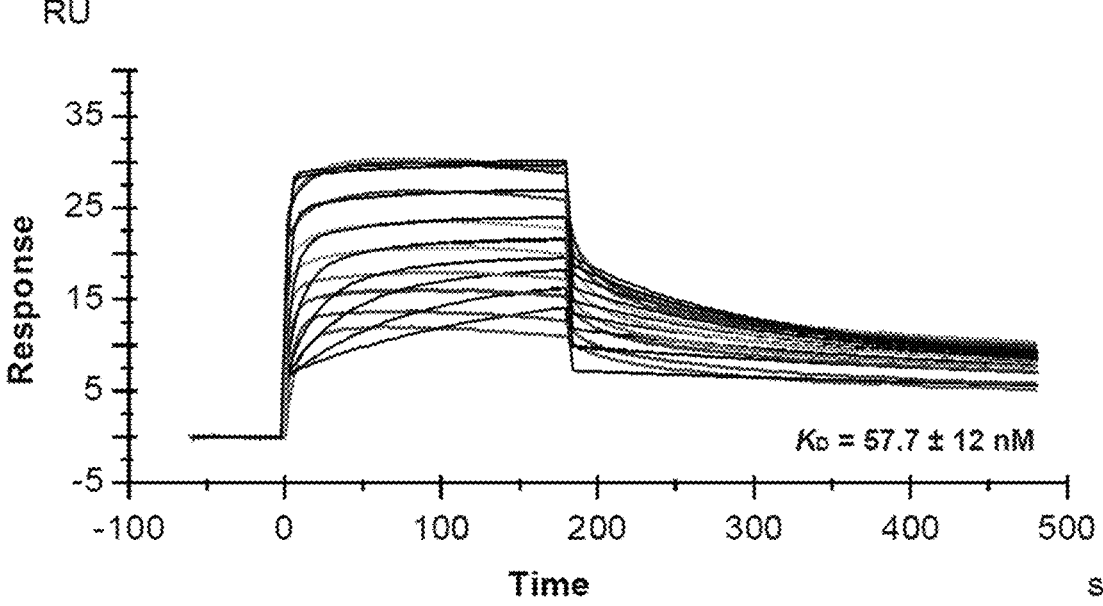

FIG. 7 shows the results of test of the affinity of AGM-330
for NCL by SPR, expressed as $K_d$. The SPR sensorgrams
result from experiments representative of a set of three
separate experiments using different sensor chips with simi-
lar results. Recombinant NCL was immobilized on a CM5
sensor chip. Various concentrations of AGM-330 (20
nM-2.5 µM) were incubated with immobilized NCL and
analyzed on a Biacore T-200 instrument.

Figure 8:
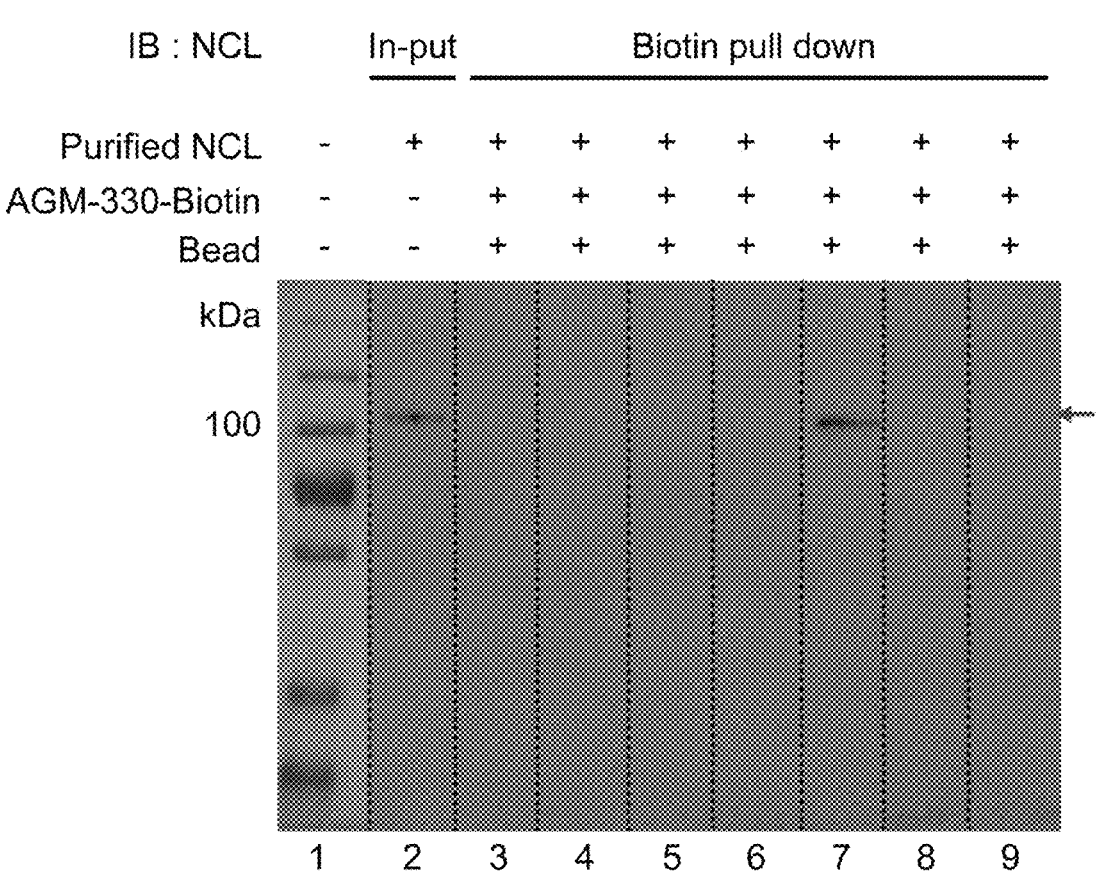

FIG. 8 shows the results of direct interaction analysis
between AGM-330 and purified NCL by biotin pull-down
analysis. Immunoblotting analysis of the eluted protein
shows formation of biotin pull-down using an anti-NCL
antibody. Lane 1: protein marker; Lane 2: input of purified
NCL; Lane 3: flow through after incubated with AGM-330-
biotin; Lane 4-6: bead washing fraction; Lane 7-8: elution of
AGM-330 binding proteins. Arrows indicate the presence of
NCL.

Figure 9:
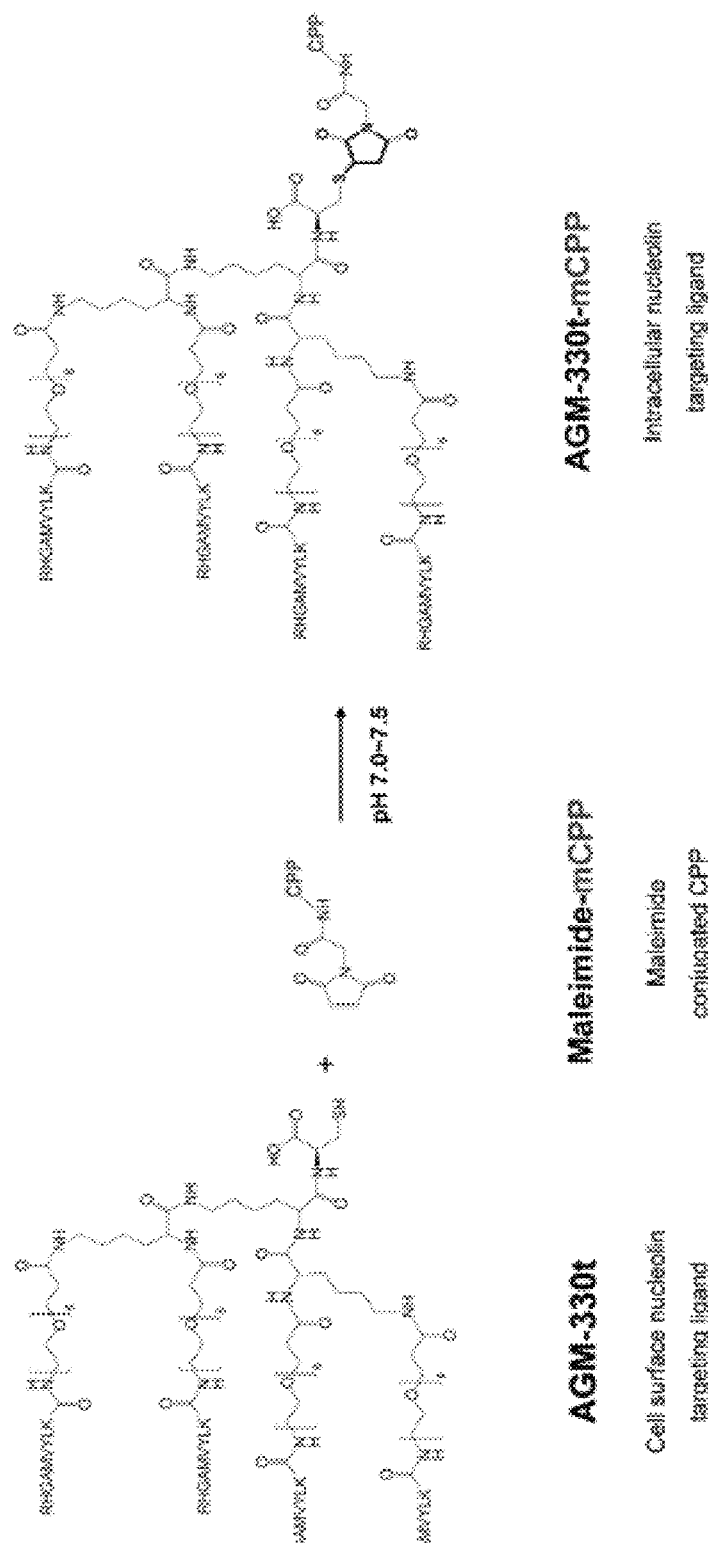

FIG. 9 is a diagram showing the synthesis process of the
AGM-330t-mCPP fusion peptide including the pendant
groups RHGAMVYLK (SEQ ID NO: 1).

Figure 10:
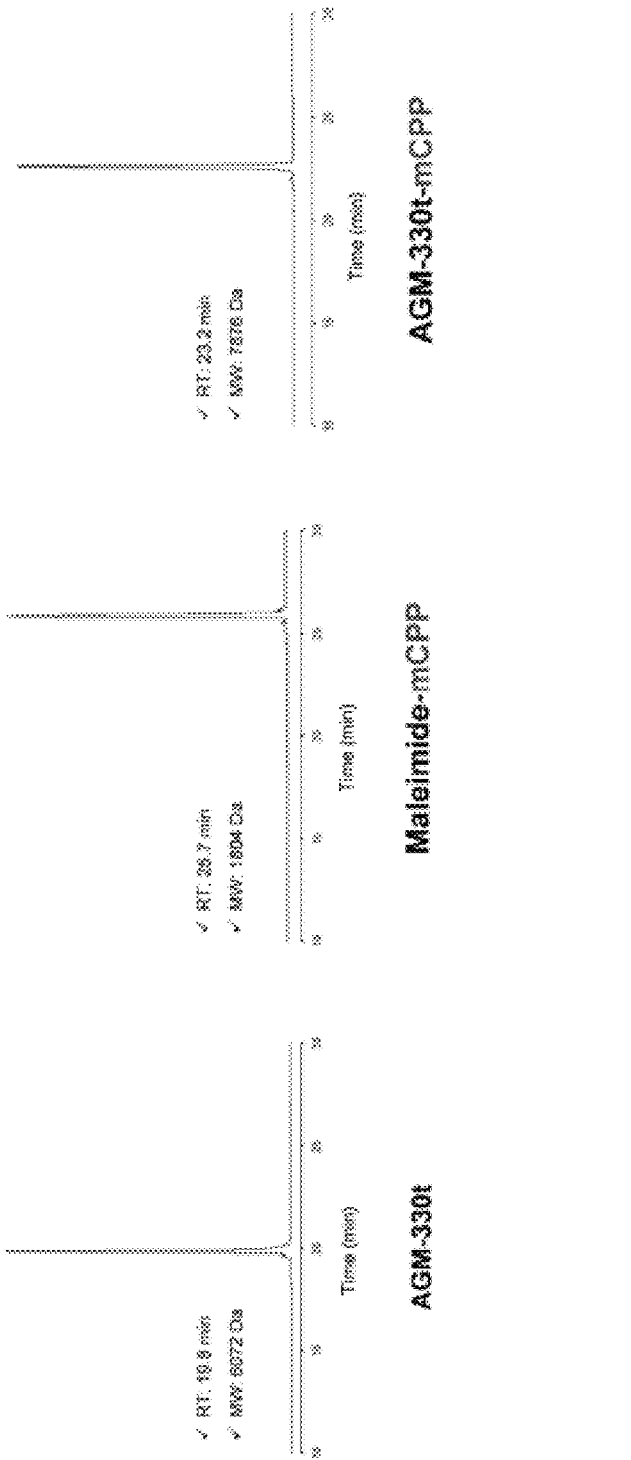

FIG. 10 shows the results of HPLC and MS analysis of the
AGM-330t-mCPP fusion peptide, AGM-330t and maleim-
ide-CPP.

Figure 11:
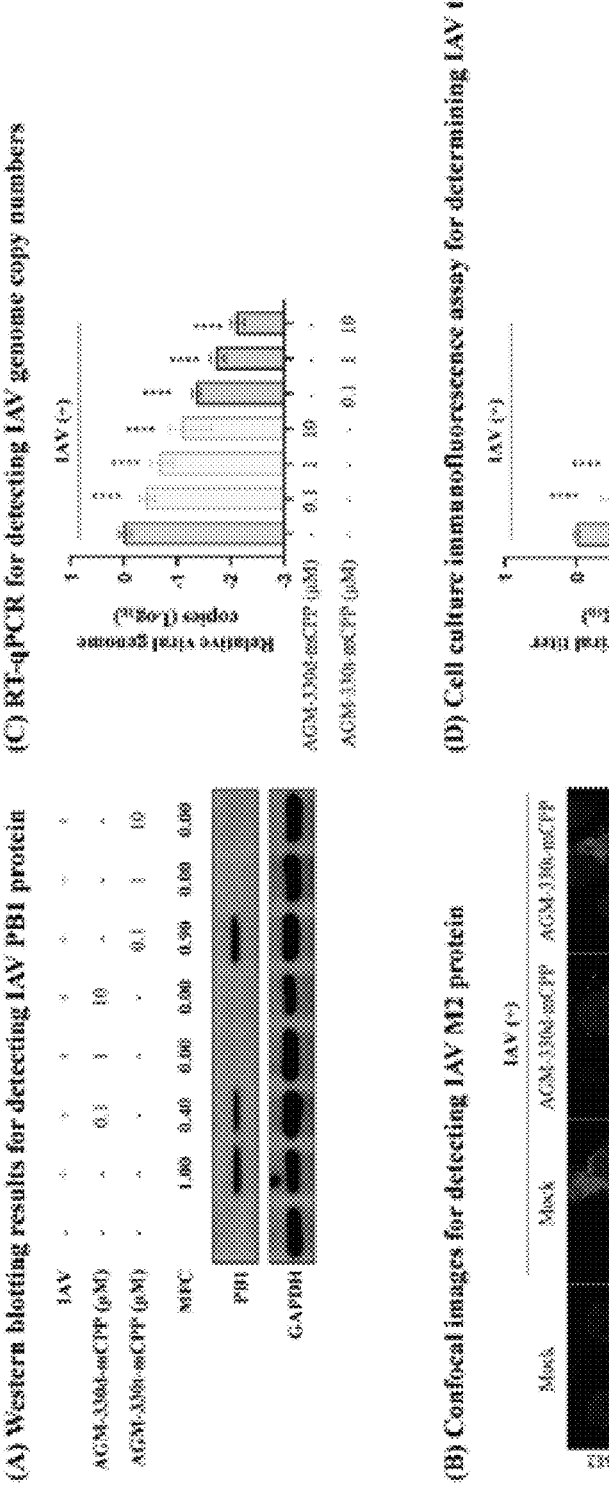

FIG. 11 shows the inhibitory effect of AGM-330 against
influenza A virus (IAV) proliferation.

Figure 12:
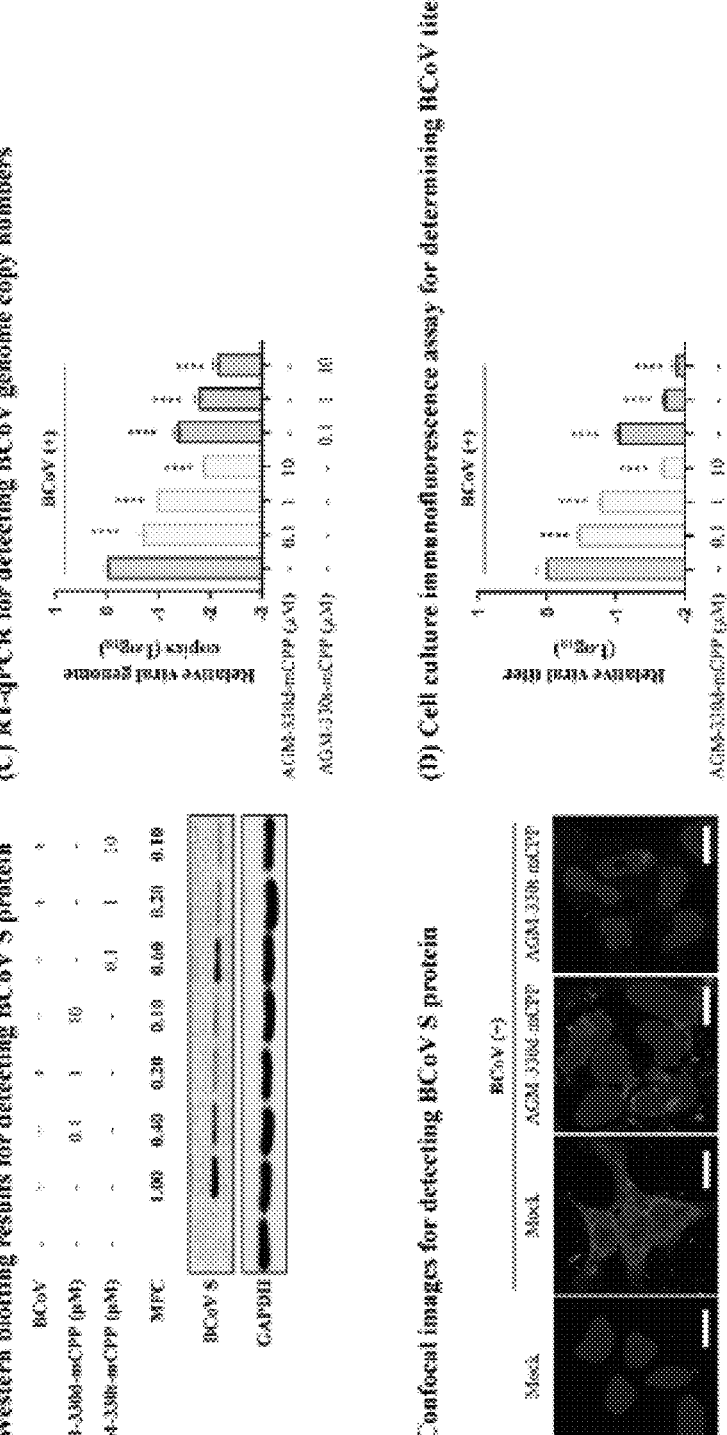

FIG. 12 shows the inhibitory effect of AGM-330 against
bovine coronavirus (BCoV).

Figure 13:
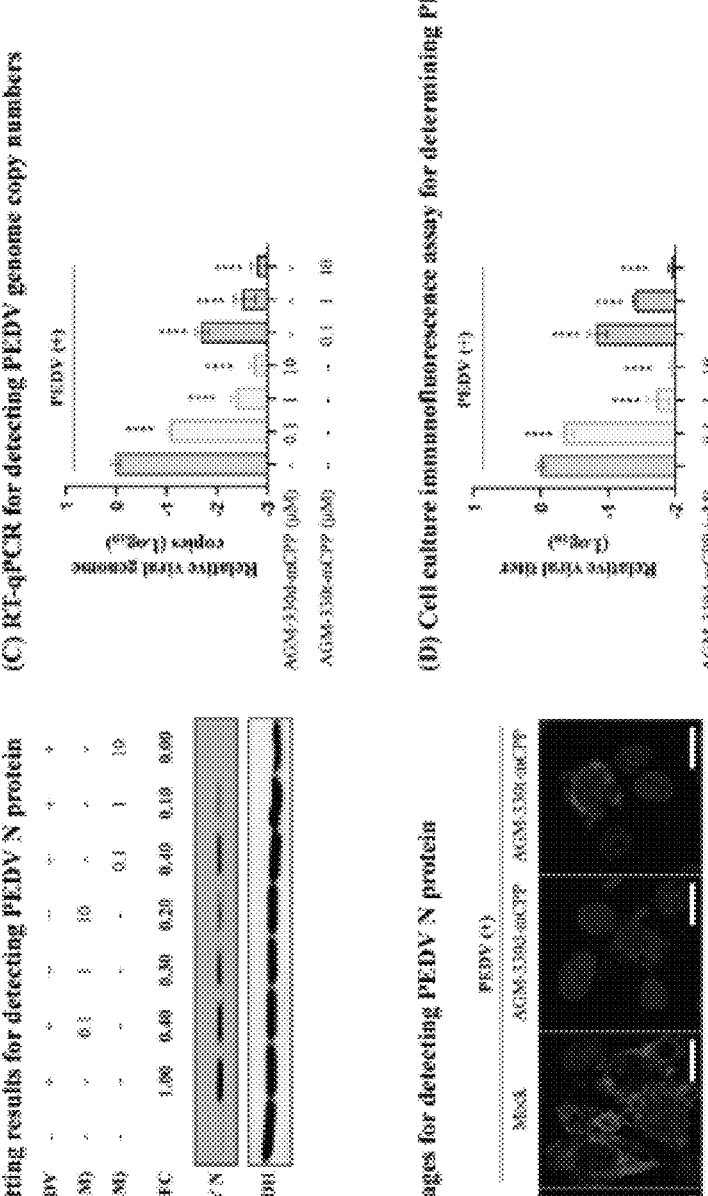

FIG. 13 shows the inhibitory effect of AGM-330 against
porcine epidemic diarrhea virus (PEDV).

Figure 14:
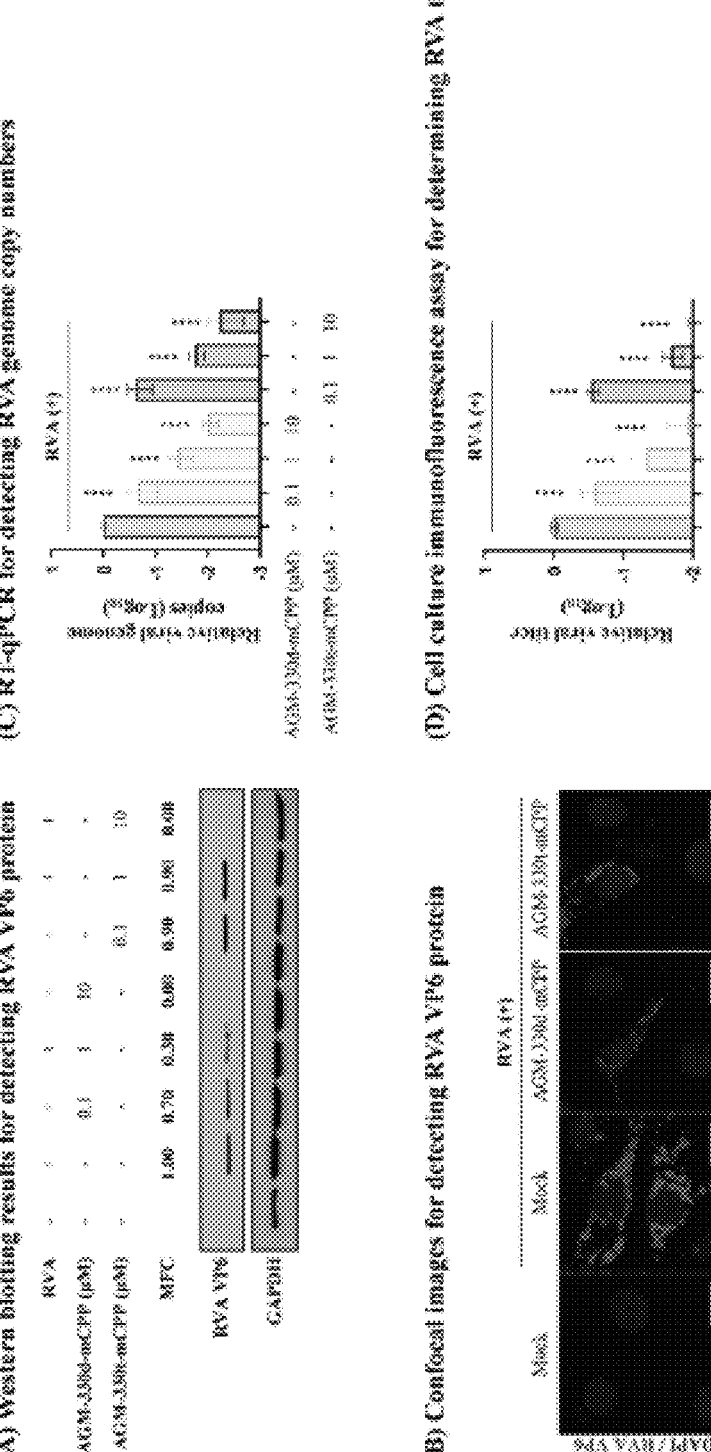

FIG. 14 shows the inhibitory effect of AGM-330 against
bovine rotavirus (RVA).

Figure 15:
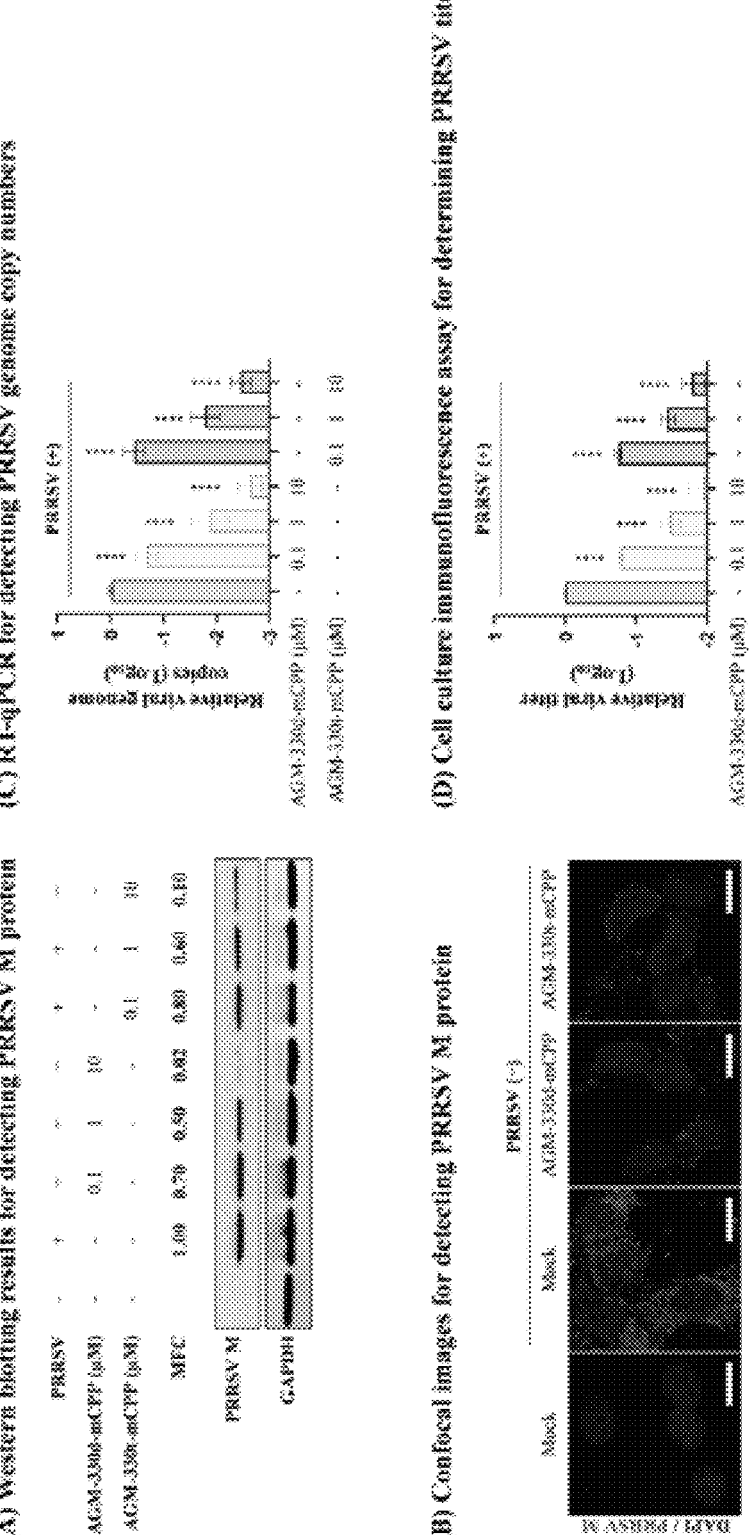

FIG. 15 is a graph showing the inhibitory effect of
AGM-330 against porcine reproductive and respiratory syn-
drome virus (PRRSV) proliferation.

FIG. 16 is a graph showing the inhibitory effect of
AGM-330 against porcine sapovirus (PSaV) proliferation.

Figure 17:
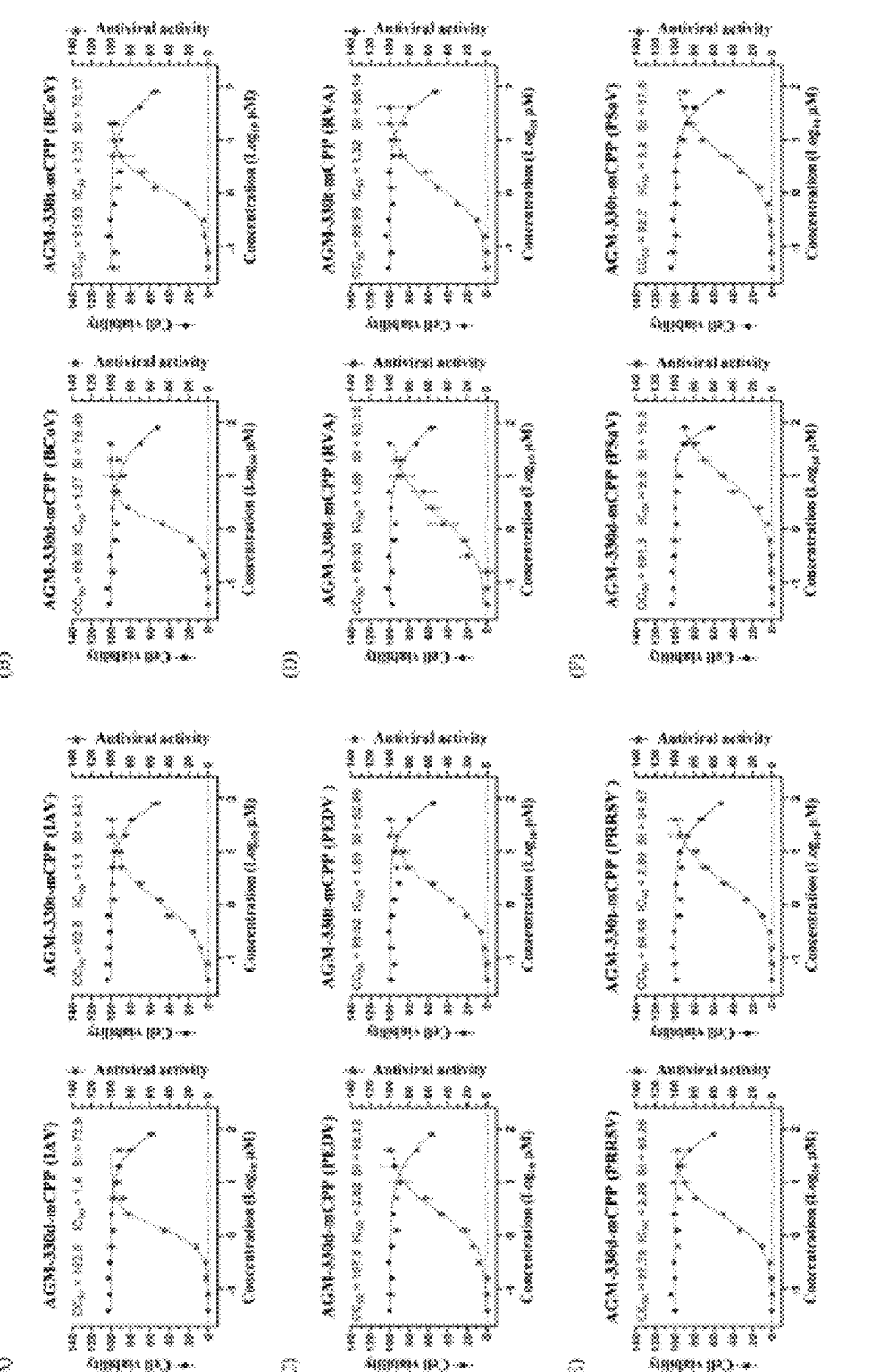

FIG. 17 is a graph showing the half maximal cytotoxic
concentration ($CC_{50}$) of AGM-330, the half maximal inhibi-
tory concentration ($IC_{50}$) of influenza A virus (IAV), bovine
coronavirus (BCoV), porcine epidemic diarrhea virus
(PEDV), bovine rotavirus, porcine reproductive and respi-
ratory syndrome virus (PRRSV), and porcine sapovirus
(PSaV) of AGM-330 (RVA), and selective index [$SI=CC_{50}/
IC_{50}$]).

Figure 18:
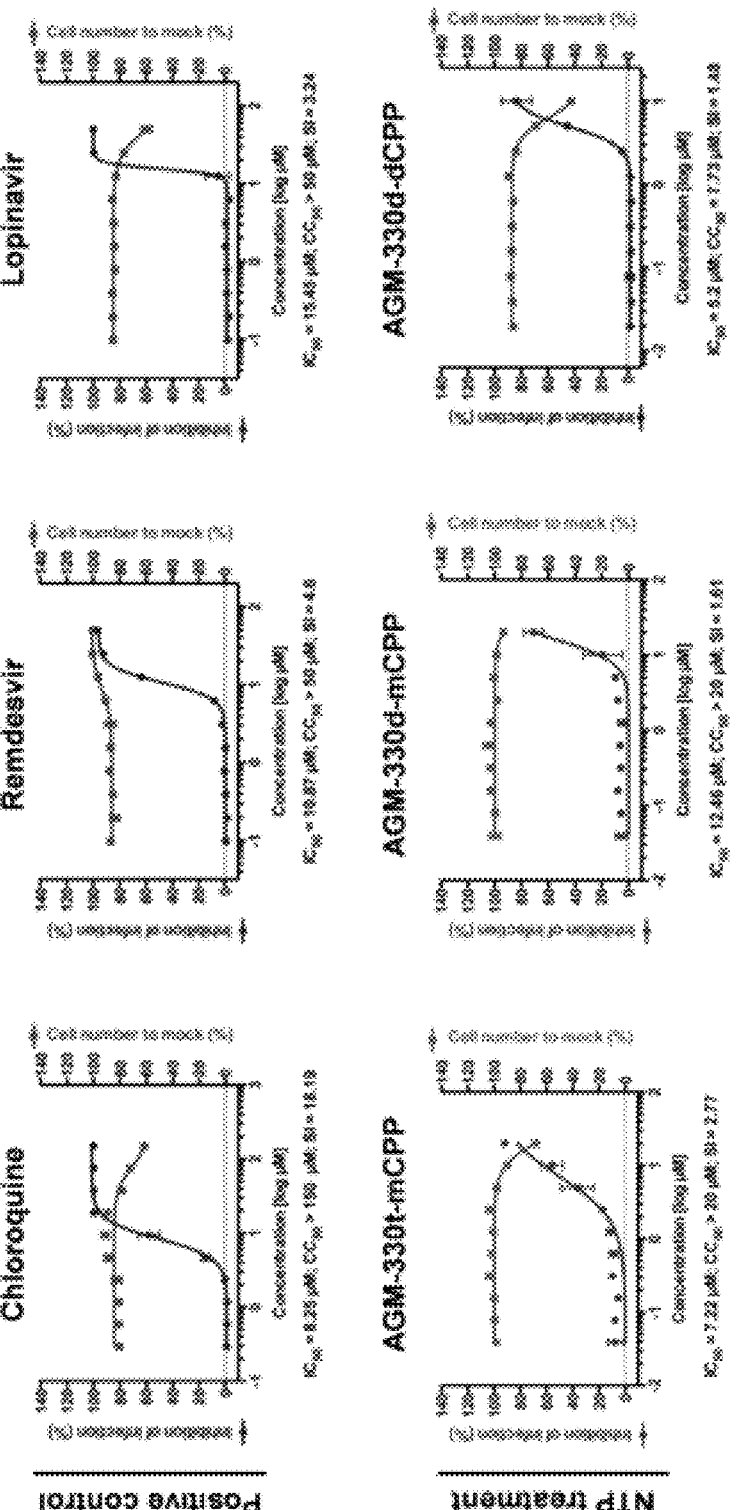

FIG. 18 is a graph showing the half maximal cytotoxic
concentration ($CC_{50}$) of AGM-330, the half maximal inhibi-
tory concentration ($IC_{50}$) of severe acute respiratory syn-
drome coronavirus 2 (SARS-COV-2) of AGM-330, and the
selective index ([$SI=CC_{50}/IC_{50}$]).

Figure 19:
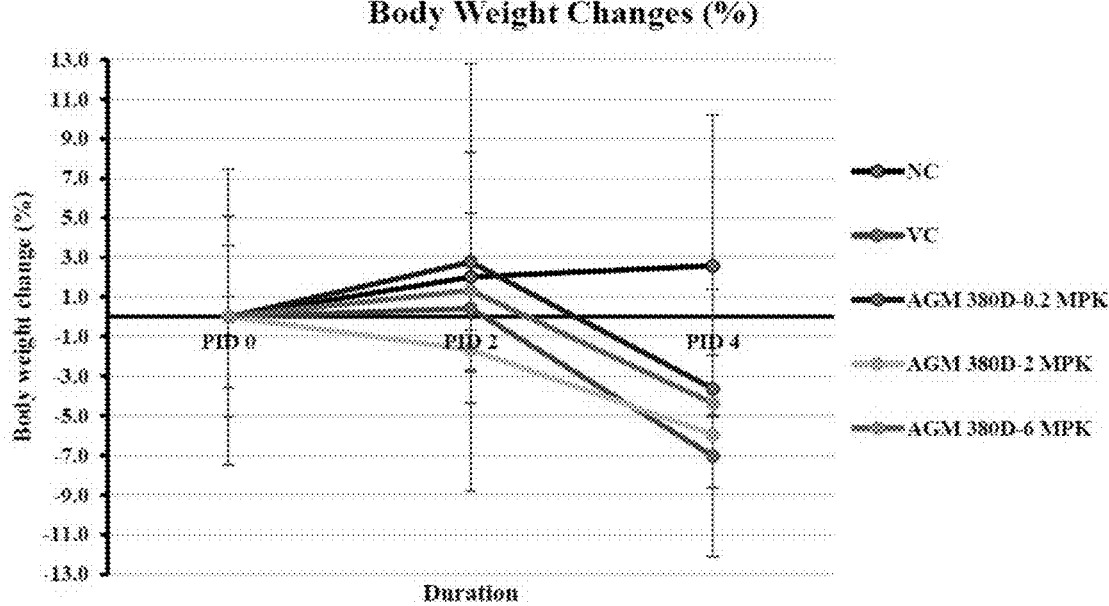

FIG. 19 is a graph showing the effect of AGM-330d-
mCPP (AGM-380D) t changes in SARS-COV-2-infected
hamsters.

Figure 20:
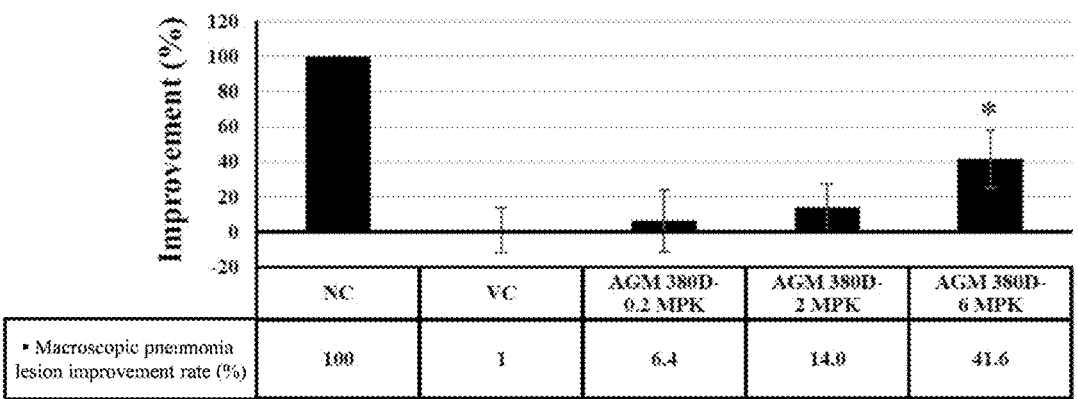

FIG. 20 shows the improved macroscopic lung lesions of
AGM-330d-mCPP (AGM-380D) in SARS-COV-2-infected
hamsters.

Figure 21:
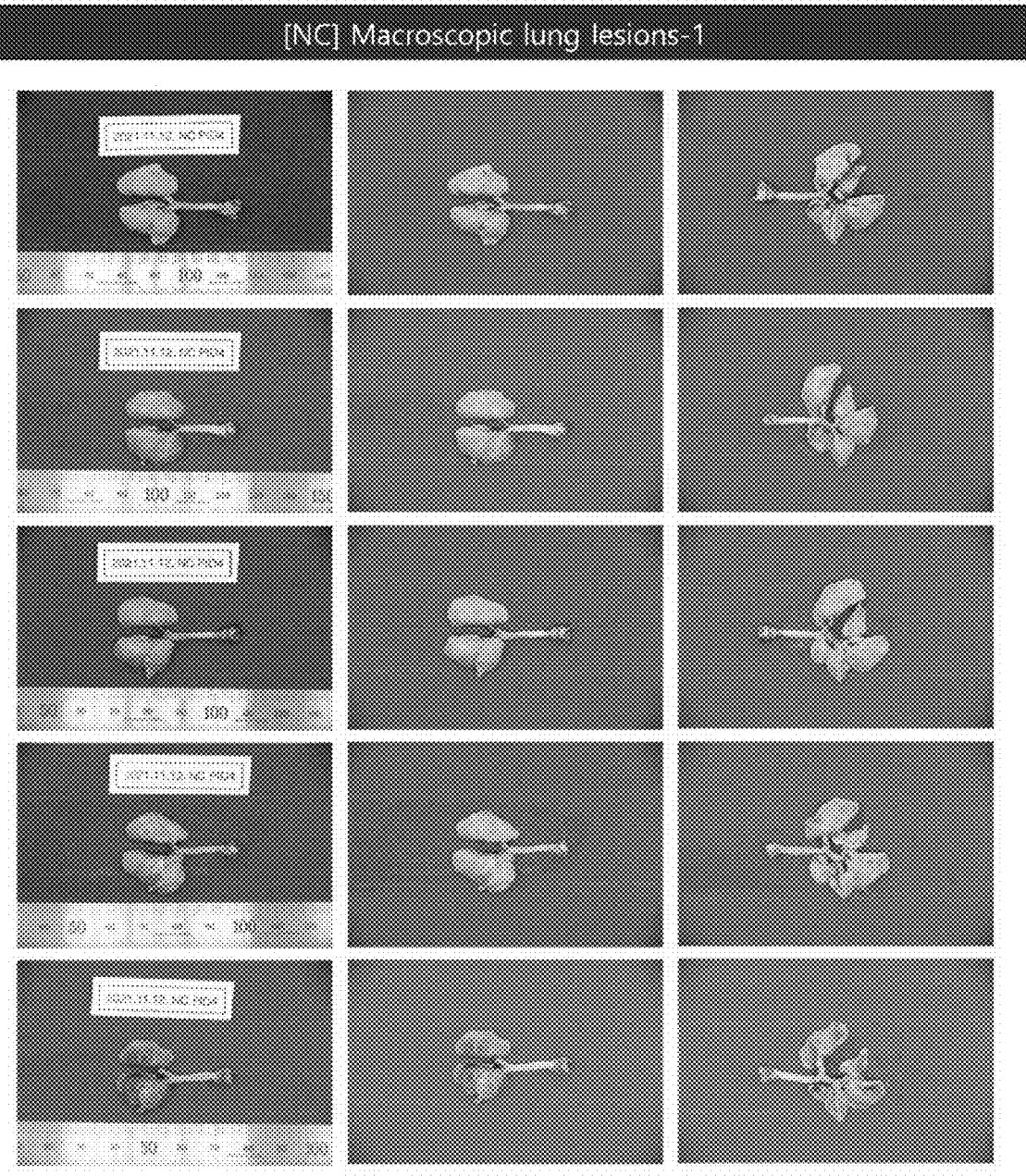

FIG. 21 shows macroscopic lung lesions of negative
control (NC) lung tissues in SARS-COV-2-infected ham-
sters.

Figure 22:
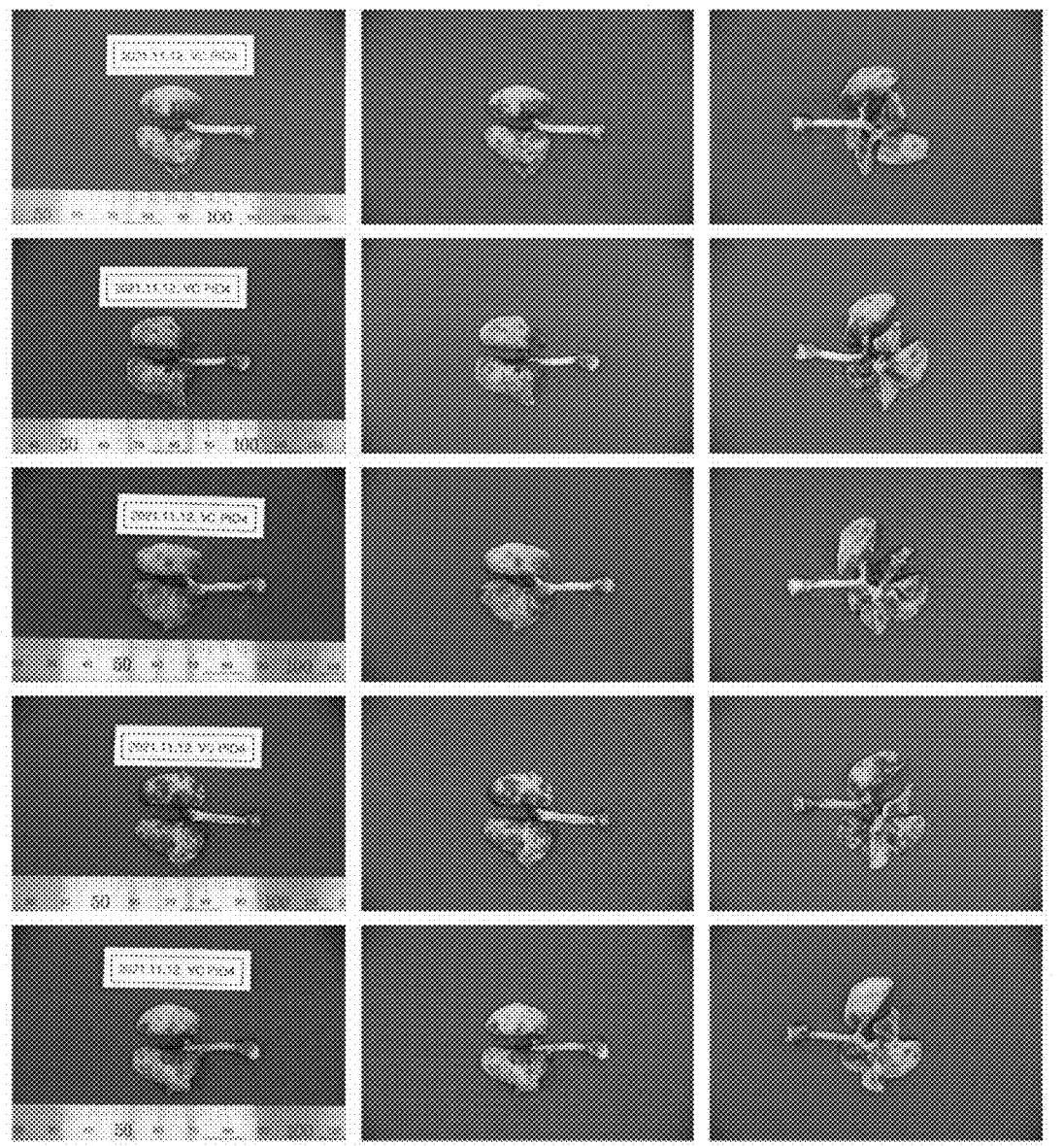

FIG. 22 shows macroscopic lung lesions of virus control
(VC) lung tissues in SARS-COV-2-infected hamsters.

Figure 23:
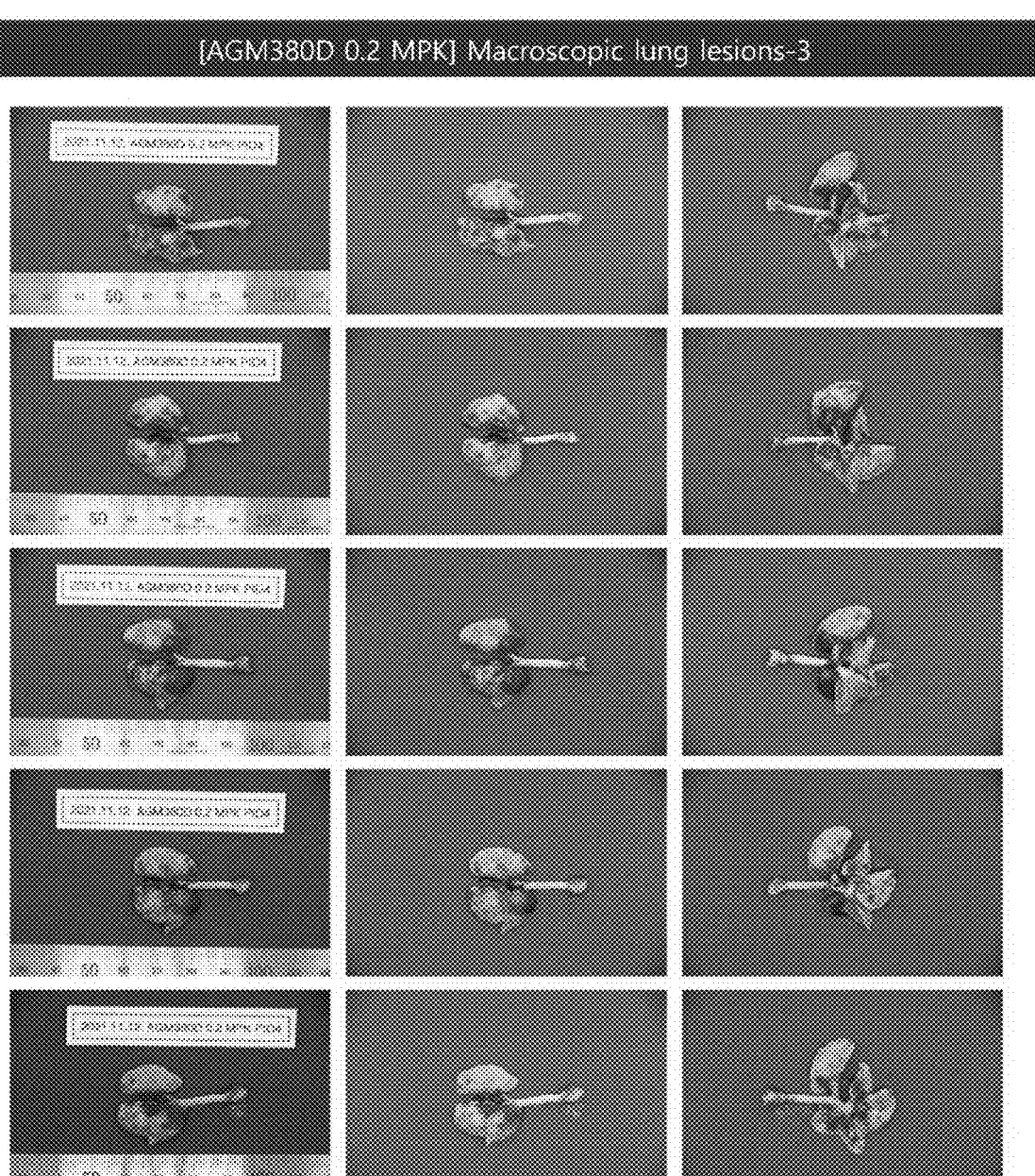

FIG. 23 shows macroscopic lung lesions of lung tissues of
SARS-COV-2-infected hamsters administered AGM-330d-
mCPP (AGM-380D, 0.2 mg/kg).

Figure 24:
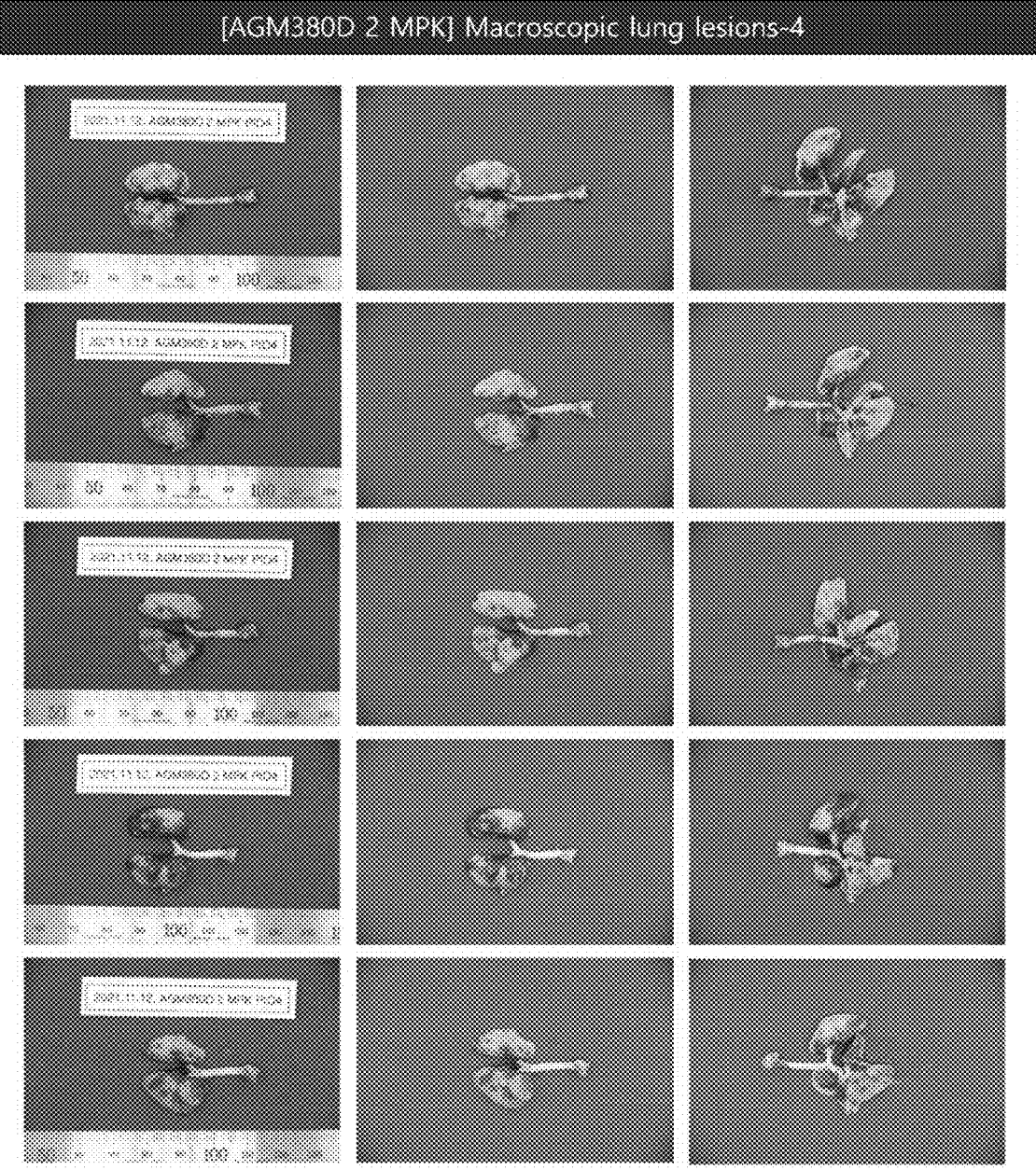

FIG. 24 shows macroscopic lung lesions of lung tissues of
SARS-COV-2-infected hamsters administered AGM-330d-
mCPP (AGM-380D, 2 mg/kg).

Figure 25:
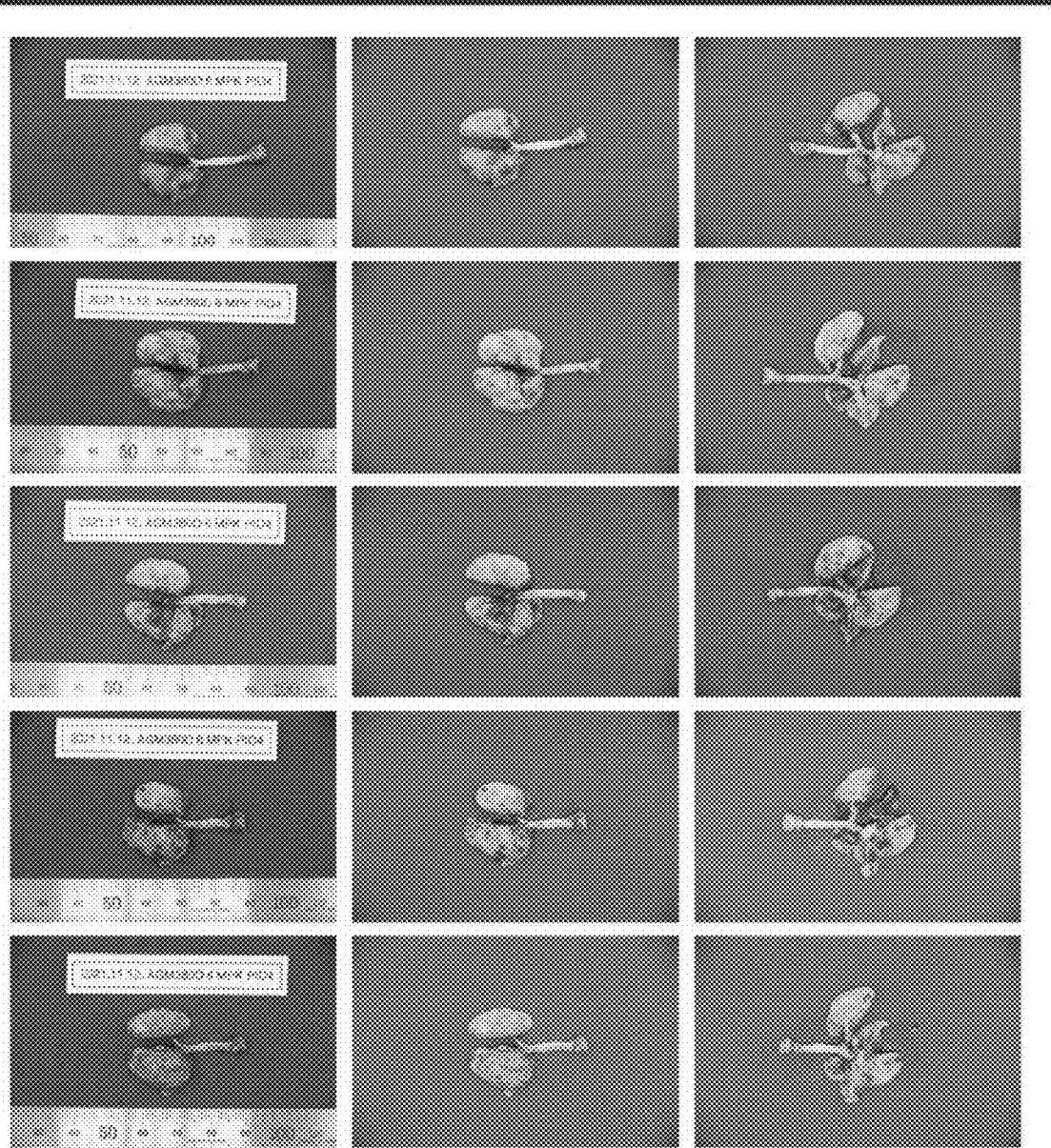

FIG. 25 shows macroscopic lung lesions of lung tissues of
SARS-COV-2-infected hamsters administered AGM-330d-
mCPP (AGM-380D, 6 mg/kg).

Figure 26:
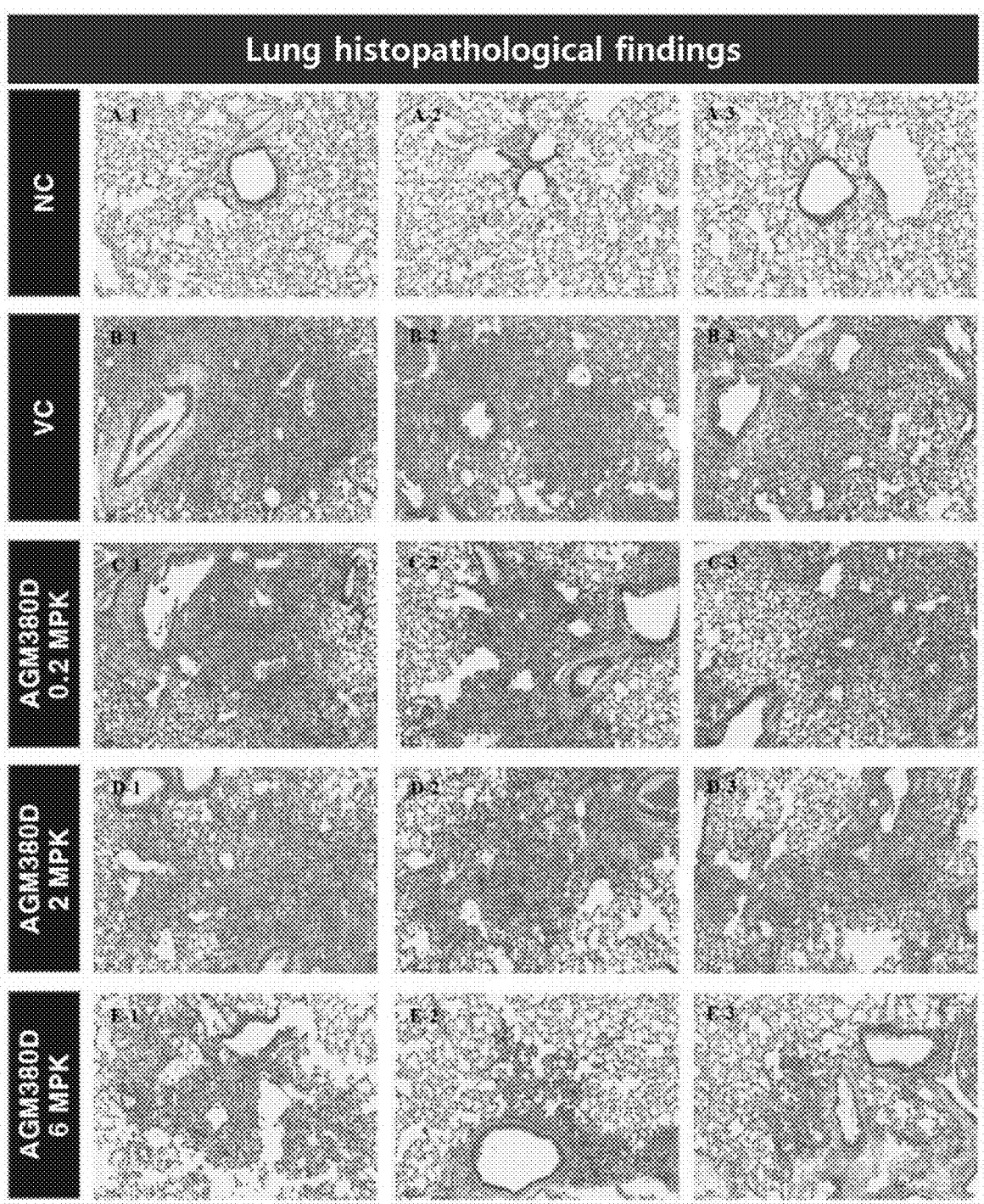

FIG. 26 shows histopathology analysis of lung tissues of
control and test groups for SARS-COV-2-infected hamsters.

FIG. 27 shows the in vivo antiviral effect of AGM-330
against influenza A virus (IAV) infection.

Figure 28:
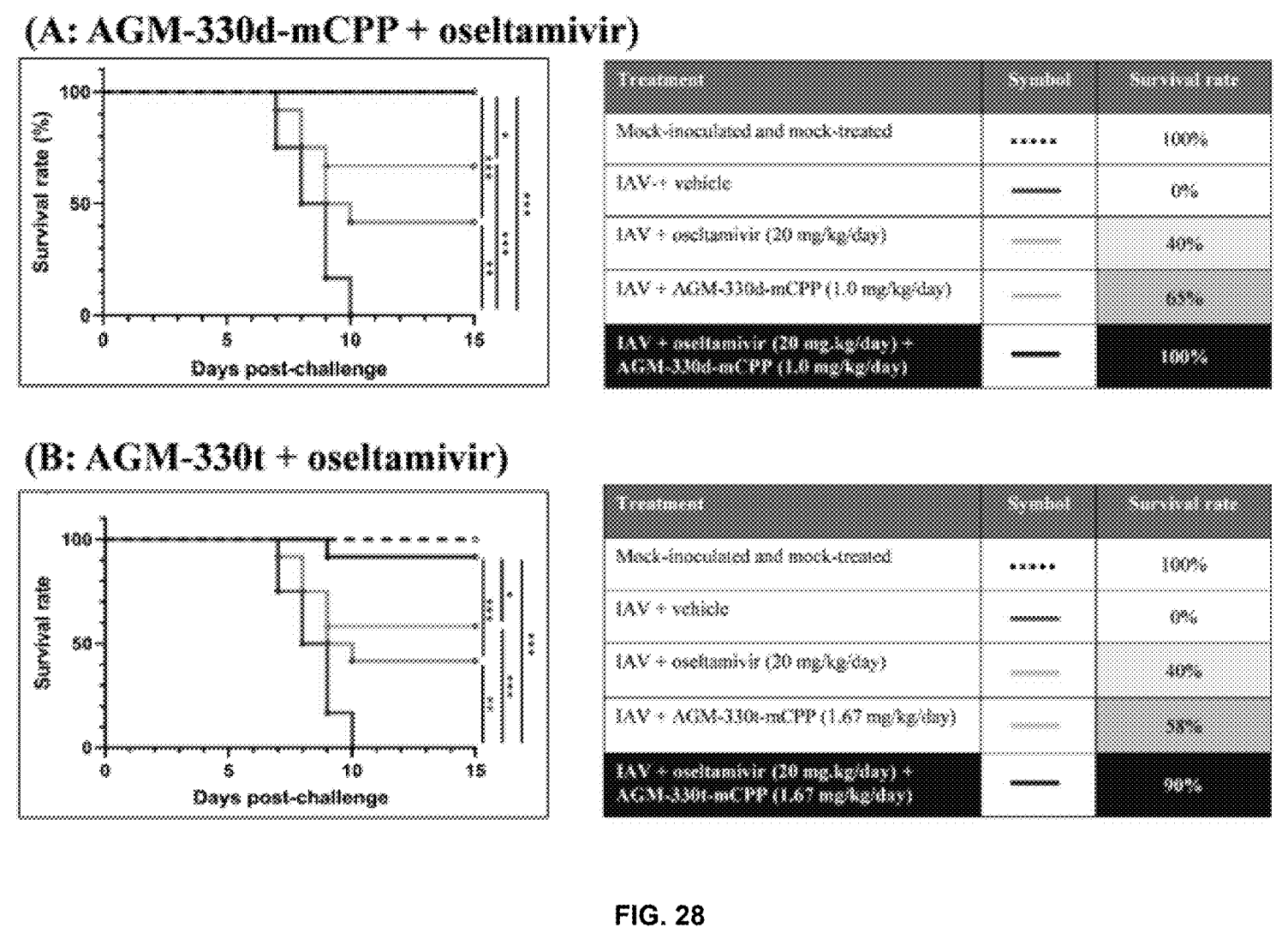

FIG. 28 shows t the in vivo antiviral effect of combined
administration of AGM-330 and oseltamivir against influ-
enza A virus (IAV) infection.

FIG. 29 shows the inhibitory effect of AGM-330 against
influenza A virus (IAV) replication.

DETAILED DESCRIPTION AND PREFERRED EMBODIMENTS OF THE INVENTION

Unless defined otherwise, all technical and scientific
terms used herein have the same meanings as appreciated by
those skilled in the field to which the present invention
pertains. In general, the nomenclature used herein is well-
known in the art and is ordinarily used.

In one aspect, the present invention is directed to:

an antiviral composition comprising an AGM peptide
specifically binding to nucleolin (NCL), wherein the
AGM peptide comprises an amino acid sequence
selected from the group consisting of:

(a) an amino acid sequence represented by any one of
SEQ ID NOS: 1 to 8; and (b) an amino acid sequence comprising at least one amino
acid mutation selected from the following group in the
amino acid sequence represented by SEQ ID NO: 1:

(i) substitution of the fifth methionine residue from the
N-terminus;

(ii) substitution of the seventh tyrosine residue from the
N-terminus; and (iii) insertion of a leucine or lysine residue at the C-ter-
minus.

The discovery of peptide ligands capable of functionally
and specifically targeting tumors provides new opportunities
for cancer diagnosis and treatment. However, the use of
peptide ligands has been greatly limited due to the short
biological half-lives thereof.

In the present invention, 2,600,000 peptide synthesized
using one-bead-one-compound libraries are (OBOC) com-
bination along multiple-antigen-peptide with (MAP) synthe-
sis, and then AGM-330, AGM-331, AGM-332, AGM-333,
AGM-334, AGM-335, AGM-336, and AGM-337, which are
novel cancer-specific peptide ligands having the amino acid
sequences shown in Table 1, are identified (FIG. 3), and the
peptide ligands specifically binding to cancer cells in vitro and in vivo were identified by cell binding assay, flow cytometry, and fluorescence confocal microscopy.

In addition, it was found by pull-down analysis and LC-MS/MS analysis that membrane nucleolin (NCL) was the target protein of AGM-330, AGM-331, AGM-332, AGM-333, AGM-334, AGM-335, AGM-336 and AGM-337.

TABLE 1

| Name | Amino acid sequence | SEQ ID NO: |
|---|---|---|
| AGM-330 | RHGAMVYLK | 1 |
| AGM-331 | ADHRHRRSG | 2 |
| AGM-332 | AVARARRRR | 3 |
| AGM-333 | RFLKNKKAR | 4 |
| AGM-334 | RWLKNKKAR | 5 |
| AGM-335 | FGRLKKPLK | 6 |
| AGM-336 | KRRRRERAG | 7 |
| AGM-337 | KRRRKAPTD | 8 |

Three (AGM-330, AGM-331 and AGM-332) of the eight peptides had strong, specific, and preferential binding to a breast cancer cell line (MDA-MB-231) and a human normal breast cell line (MCF) and did not bind or weakly bind to a human normal breast cell line (MCF-10A) (see FIG. 4 in A and B thereof).

In addition, it was confirmed that AGM-330 having the amino acid sequence of SEQ ID NO: 1 still maintains the strong and specific binding to nucleolin although it has mutation in some amino acid residues.

Specifically, in the present invention, the amino acid mutation in the amino acid sequence of SEQ ID NO: 1 may comprise at least one mutation selected from the group consisting of:

(i) substitution of the fifth methionine residue from the N-terminus;

(ii) substitution of the seventh tyrosine residue from the N-terminus; and (iii) insertion of a leucine or lysine residue into the C-terminus, but is not limited thereto.

Preferably, in the present invention, the amino acid mutation in the amino acid sequence of SEQ ID NO: 1 may comprise at least one mutation selected from the group consisting of:

(i) substitution of the fifth methionine residue from the N-terminus with leucine or norleucine;

(ii) substitution of the seventh tyrosine residue from the N-terminus with phenylalanine; and (iii) insertion of a leucine or lysine residue into the C-terminus, but is not limited thereto.

In the present invention, the amino acid sequence comprising the mutation may be selected from the group consisting of SEQ ID NO: 9 to SEQ ID NO: 15 and SEQ ID NO: 20, but is not limited thereto (Table 2).

TABLE 2

| Amino acid mutation in AGM-330 | Amino acid sequence | SEQ ID NO: |
|---|---|---|
| R1 → K1 | KHGAMVYLK | 9 |
| H2 → R2 | RRGAMVYLK | 10 |
| A4 → L4 | RHGLMVYLK | 11 |
| M5 → L5 | RHGALVYLK | 12 |
| M5 → Nle5(Nle: Norleucine) | RHGA(Nle)VYLK | 13 |
| V6 → A6 | RHGAMAYLK | 14 |
| Y7 → F7 | RHGAMVFLK | 15 |
| R1H2 → Deletion | GAMVYLK | 16 |
| R1H2 → Insertion | RHRHGAMVYLK | 17 |
| R1H2R3H4 → Insertion | RHRHRHGAMVYLK | 18 |
| Reverse sequence | KLYVMAGHR | 19 |
| L10K11L12K13 → Insertion | RHGAMVYLKLKLK | 20 |

In the amino acid sequence of SEQ ID NO: 13, "Nle" means Norleucine.

As used herein, the term "AGM", "AGM peptide", or "AGM peptide ligand" collectively refers to a peptide having an amino acid sequence selected from the group consisting of SEQ ID NO: 1 to SEQ ID NO: 20, or refers to at least one of such peptide.

In the present invention, the AGM peptide specifically binds to nucleolin (NCL).

In normal cells, nucleolin is mainly present in the nucleolus, but is also found in the nucleoplasm, cytoplasm or cell membrane and is involved in various cellular functions such as ribosome biosynthesis, chromatin reorganization and stabilization, DNA and RNA metabolism, rRNA transcription, cell cycle regulation, cell division, angiogenesis and microRNA processing (Dario Palmieri, et al., *Proc Natl Acad Sci USA*. 2015 Jul. 28; 112 (30): 9418-23).

It has been reported that the expression of NCL is significantly up-regulated in various cancer cells (thyroid cancer, breast cancer, lung cancer, gastric cancer, pancreatic cancer, prostate cancer, and the like) (Shen N, et al. Oncotarget. 2014; 5:5494-509) and up-regulated expression of NCL is associated with malignancy and cancer metastasis.

NCL overexpressed in the cytoplasm is involved in the proliferation and differentiation of cancer cells by stabilizing anti-apoptotic factors such as Bcl-2 and IL2 and suppressing the expression of tumor suppressors such as p53. NCL overexpressed in the cell membrane acts as a receptor for growth factors such as HDGF or VEGF, moves into the nucleus by endocytosis, and promotes cancer cell proliferation and metastasis. Cell membrane NCL mediates the attachment or entry of viruses (RSV, HIV, H1N1, H3N2, H5N1 and H7N9) into host cells and thus affects viral infection and proliferation (Kotb Abdelmohsen and Myriam Gorospe, RNA Biology. 2012; 9:799-808).

Human cells abnormally overexpress nucleolin due to carcinogenesis and viral infection, and these overexpressed NCLs are distributed at high concentrations in the cell membrane and cytoplasm. Therefore, NCL may be a novel target for the development of antitumor and antiviral drugs.

In one embodiment of the present invention, it was confirmed that the AGM peptide, specifically AGM-330, not only exhibits anticancer activity, but also exhibits antiviral activity of inhibiting viral infection by inhibiting the proliferation and replication of viruses.

As used herein, the term "anti-viral activity" or "anti-viral (efficacy) ability" refers to the ability to inhibit the replication or proliferation of various subtypes and mutant particles of the virus in host cells.

In the present invention, the antiviral composition comprises an AGM peptide-PEG conjugate conjugated with a polyethylene glycol (PEG) chain comprising two or more ethylene glycol groups having a structure of —[CH₂—CH₂—O]— in the AGM peptide.

In the present invention, the polyethylene glycol chain may comprise not only a general polyethylene glycol chain having a structure of Formula 1, but also a derivative thereof and the derivative of the polyethylene glycol chain is for example polyethylene glycol carboxylic acid having a structure of Formula 2, but is not limited thereto.

$$H\text{---}\left[O\diagup\diagdown\diagup\diagdown\right]_n O\diagdown H \qquad \text{(Formula 1)}$$

(Polyethylene glycol)

$$H_2N\diagup\diagdown\left(\diagup O\diagdown\right)_x\diagup\diagdown\underset{\underset{O}{\|}}{C}\text{---}OH \qquad \text{(Formula 2)}$$

(Amino Polyethylene glycol Carboxylic acid)

The conjugation with polyethylene glycol (PEG) (PEGylation) has been widely used to improve the pharmacological properties of therapeutic proteins (Gupta V, et al. J Cell Commun Signal. 2019; 13:319-30). In the present invention, PEGylation was used to reduce steric hindrance and increase hydrophilicity. However, PEG has negative clinical effects on therapeutic molecules due to immunogenicity thereof (Moreno A, et al. Cell Chem. Biol. 2019; 26:634-44.e3). Previous studies have suggested that the anti-PEG immune response to PEGylated molecules depends on immunogenicity corresponding n and the molecular weight of PEG (Wan X, et al. Process Biochem. 2017; 52:183-91).

In the present invention, the polyethylene glycol chain may have 2 to 24 ethylene glycol units, preferably 4 to 20 ethylene glycol units, more preferably 6 to 18 ethylene glycol units, and most preferably 6 to 12 ethylene glycol units, but is not limited thereto.

The polyethylene glycol chain may be linked to the AGM peptide through a linker. Accordingly, the AGM peptide-PEG conjugate may have the structure of Formula 1 below, but is not limited thereto.

AGM-L₁-PEG (Formula 1)

In Formula 1, 'PEG' represents a polyethylene glycol chain, and Li means a linker.

The linker Li is preferably selected from the group consisting of a single bond (direct bond), $C_1$-$C_{20}$ alkyl, $C_1$-$C_{20}$ alkylene, —S—, —NH— and —O—, but is not limited thereto, and may comprise a peptide bond having the form of —CONH— along with the carboxy group of the C-terminal amino acid of the AGM peptide, but is not limited thereto.

In addition, a functional group for conjugating another substance, preferably a drug, may be introduced into the opposite end of the PEG bonded to AGM in the AGM peptide-PEG conjugate of Formula 1. Examples of such functional groups include carboxyl (COOH), amine (NH₂) and thiol groups, but are not limited thereto.

For example, as shown in Formulas 2 to 4, lysine (K) having amine (NH₂) and/or cysteine (C) having a thiol group may be a conjugated at the other end of PEG bound to the AGM peptide in the AGM peptide-PEG conjugate, but is not limited thereto.

AGM-L₁-PEG-K (Formula 2)

AGM-L₁-PEG-C (Formula 3)

AGM-L₁-PEG-K-C (Formula 4)

For example, in one embodiment of the present invention, the AGM-300 monomer (AGMm), in which lysine and cysteine are introduced at the other end of PEG bound to AGM-330, the AGM-330-PEG conjugate, which is a conjugate of AGM-300 as the AGM peptide with PEG, may have the structure of Formula 5.

RHGAMVYLK-L₁-PEG-K-C (Formula 5)

In Formula 5, PEG may be linked by a linker (L₁) comprising a peptide bond in the structure of Formula 6 formed through a condensation reaction between the carboxyl group of the lysine (K) at the AGM-330 C-terminus and the amine, but is not limited thereto.

$$\text{RHGAMVYLK}\diagdown\underset{\underset{O}{\|}}{\phantom{C}}\diagup\overset{H}{\underset{}{N}}\diagup\diagdown\diagup\diagdown\left(O\diagdown\right)_{12}\diagup\diagdown \qquad \text{(Formula 6)}$$

In the present invention, the composition may comprise a multimer comprising two or more AGM peptide-PEG conjugates comprising the AGM peptide-PEG conjugate.

In the present invention, the multimer may comprise 2 to 8 AGM peptides or AGM peptide-PEG conjugates, preferably 2 to 6 AGM peptides, or AGM peptide-PEG conjugates, more preferably 2 to 4 AGM peptides, or AGM peptide-PEG conjugates, but is not limited thereto.

For example, in the present invention, among the multimer, the dimer may have a configuration in which two AGM peptides or AGM peptide-PEG conjugates are linked to each other by a linker (L₂). Among the multimers, the tetramer may have a configuration in which the dimers are linked to each other by an additional linker (L₃), but is not limited thereto. Furthermore, it is obvious to those skilled in the art that hexamers, octamers, and higher multimers may be linked in a similar manner.

For example, in one embodiment of the present invention, the dimer and tetramer of the AGM peptide-PEG conjugate according to the present invention may have structures shown in Formula 7 and Formula 8, but are not limited thereto.

$$\begin{array}{l} \text{AMG}\text{---}\text{L}_1\text{---}\text{PEG}\text{---}\!\!\!\rceil \\ \qquad\qquad\qquad\quad \text{L}_2\text{---} \\ \text{AGM}\text{---}\text{L}_1\text{---}\text{PEG}\text{---}\!\!\!\rceil \end{array} \qquad \text{(Formula 7)}$$

-continued (Formula 8)

The linkers $L_2$ and $L_3$ may be the same as or different from each other and may be independently cleavable or non-cleavable.

The linkers $L_1$ and $L_2$ are preferably selected from the group consisting of a single bond (direct bond), amino acids or derivatives thereof, $C_1$-$C_{20}$ alkyl, $C_1$-$C_{20}$ alkylene, —S—, —NH— and —O—, but are not limited thereto, and are preferably amino acids or derivatives thereof, more preferably lysine (Lys, K) or arginine (Arg, R) having two or more amine groups, but are not limited thereto.

Most preferably, the linkers $L_2$ and $L_3$ may be lysine (Lys, K), and the amine group ($NH_2$) of the lysine may be linked to PEG in a similar structure to a peptide bond such as —C—CONH—, but is not limited thereto.

In addition, a functional group for conjugating another substance, preferably a drug, may be introduced into one end of the AGM peptide or the linker of the AGM peptide-PEG conjugate. For example, a functional group for conjugating a drug to $L_2$ in Formula 7 and $L_3$ in Formula 8 may be introduced.

Examples of such functional groups include amine ($NH_2$) and thiol groups, but are not limited thereto. For example, the functional group include amine ($NH_2$)-having lysine (Lysine, K) and/or thiol-having cysteine (C), but is not limited thereto.

For example, in one embodiment of the present invention, the AGM-330 dimer (AGM-330d) and AGM-330 tetramer (AGM-330t) may have structures shown in Table 3 below, but are not limited thereto.

TABLE 3

| Name | Formula |
|---|---|
| AGM-330d | |
| AGM-330t | |

In the present invention, the composition has antiviral activity against at least one selected from the group consisting of coronavirus (CoV), influenza virus, porcine epidemic diarrhea virus (PEDV), bovine rotavirus (RVA), porcine sapovirus, porcine reproductive and respiratory syndrome virus, Alfuy virus, Banzi virus, Chikungunya virus, Dengue virus, hepatitis B virus (HBV), hepatitis C virus (HCV), human cytomegalovirus, human immunodeficiency virus (HIV), Japanese encephalitis virus, Kokobera virus, Kunjin virus, Kyasanur forest disease virus, louping ill virus, measles virus, metapneumovirus, mosaic virus, Murray Valley virus, parainfluenza virus, polio virus, Powassan virus, respiratory syncytial virus (RSV), Rocio virus, Saint Louis encephalitis virus, tick-borne encephalitis virus, West Nile virus and Yellow fever virus, but is not limited thereto.

Preferably, the coronavirus is severe acute respiratory syndrome coronavirus 2 (SARS-COV-2) or bovine coronavirus (BCoV), and the influenza virus is influenza A virus (IAV), but is not limited thereto.

In the present invention, the antiviral composition may be used in combination with a conventional drug used in the art, preferably, an antiviral agent.

The antiviral composition of the present invention may comprise a pharmaceutically acceptable carrier.

The carrier used in the pharmaceutical composition may comprise a pharmaceutically acceptable carrier, excipient and vehicle and broadly refers to "pharmaceutically acceptable carrier". Examples of the pharmaceutically acceptable carrier that can be used in the present invention comprise, but are not limited to, ion exchangers, alumina, aluminum stearate, lecithin, serum proteins (e.g., human serum albumin), buffer substances (e.g., several phosphates, glycine, sorbic acid, potassium sorbate and partial glyceride mixtures of saturated vegetable fatty acids), water, salts or electrolytes (e.g., protamine sulfate, disodium hydrogen phosphate, potassium hydrogen phosphate, sodium chloride and zinc salts), colloidal silica, magnesium trisilicate, polyvinyl pyrrolidone, cellulose-based substrates, polyethylene glycols, sodium carboxymethylcellulose, polyarylates, waxes, poly-ethylene-polyoxypropylene-blocking polymers, polyethylene glycols, wool fats and the like.

The composition of the present invention is preferably administered orally or parenterally. Parenteral administration may be intranasal, buccal, intravenous, intramuscular, intraarterial, intramedullary, intrathecal, intracardiac, transdermal, subcutaneous, intradermal, intraperitoneal, enteral, topical, sublingual or rectal administration, but is not limited thereto.

Preferably, the composition may be administered orally, intranasally or buccally, and in particular, the intranasal or parenteral administration is preferably administration through spray or aerosol, or is more preferably administration through inhalation, but is not limited thereto. The pharmaceutical composition for intranasal or buccal administration is prepared according to techniques well-known in the pharmaceutical field and is prepared as a solution in saline using benzyl alcohol or other suitable preservatives, absorption accelerators to enhance bioavailability, fluorocarbons and/or other solubilizers or dispersants known in the art.

In an embodiment, the pharmaceutical composition may also be provided in the: sterile injectable preparation as a sterile injectable aqueous or oily suspension. This suspension may be formulated in accordance with methods known in the art using suitable dispersing or wetting agents (e.g., Tween 80) and suspending agents. The sterile injectable preparation may also be a sterile injectable solution or suspension in a non-toxic parenterally acceptable diluent or solvent (e.g., a solution in 1,3-butanediol). Acceptable vehicles and solvents include mannitol, water, Ringer's solution and isotonic sodium chloride solution. In addition, sterile non-volatile oils are usually used as solvents or suspending media. For this purpose, any non-volatile oil including synthetic mono- or di-glyceride may be used. Fatty acids such as oleic acid and glyceride derivatives thereof are useful as injectable preparations like pharmaceutically acceptable natural oils (e.g., olive oils or castor oils), especially polyoxyethylated forms thereof.

The composition of the present invention may be administered orally in any orally acceptable formulations including, but not limited to, capsules, tablets, and aqueous suspensions and solutions. The oral tablets include, as commonly used carriers, lactose and corn starch. Typically, the oral tablets also include a lubricant such as magnesium stearate. The diluents useful for oral administration in a capsule formulation include lactose and dried cornstarch. When aqueous suspensions are administered orally, the active ingredient is combined with an emulsifier and suspending agent. If necessary, sweetening and/or flavoring and/or coloring agents may be added.

The composition of the present invention may also be administered in the form of a suppository for rectal administration. Such a composition may be prepared by mixing the compound of the present invention with suitable non-irritating excipients which are solid at room temperature but liquid at rectal temperature. Such substances include, but are not limited to, cocoa butter, beeswax, and polyethylene glycols.

The composition of the present invention may be formulated into a pill, dragée, capsule, solution, gel, syrup, slurry, or suspension.

In a preferred embodiment, the pharmaceutical composition for oral administration may be prepared by mixing the active ingredient with a solid excipient and may be prepared in the form of a granule to obtain a tablet or dragée formulation. Suitable excipients include sugar forms such as lactose, sucrose, mannitol and sorbitol, starch from corn, flour, rice, potatoes or other plants, or cellulose such as methyl cellulose, hydroxypropylmethyl-cellulose or sodium carboxymethylcellulose, carbohydrates such as gums, including arabic gum and tragacanth gum, or protein fillers such as gelatin and collagen. If necessary, a disintegrant or solubilizer, such as crosslinked polyvinylpyrrolidone, agar and alginic acid or a salt form thereof, for example, sodium alginate, may be added.

In another aspect, the present invention is directed to an antiviral composition comprising an AGM peptide-CPP fusion peptide in which an AGM peptide specifically binding to nucleolin (NCL) is fused with a cell-penetrating peptide (CPP), wherein the AGM peptide comprises an amino acid sequence selected from the group consisting of:

(a) an amino acid sequence represented by any one of SEQ ID NOS: 1 to 8; and (b) an amino acid sequence comprising at least one amino acid mutation selected from the following group in the amino acid sequence represented by SEQ ID NO: 1:

(i) substitution of the fifth methionine residue from the N-terminus;

(ii) substitution of the seventh tyrosine residue from the N-terminus; and (iii) insertion of a leucine or lysine residue at the C-terminus.

As used herein, the term "cell-penetrating peptide (CPP)" is a kind of signal peptide, which is a combination of specific amino acid sequences used to deliver macromolecules such as proteins, DNA, RNA, and the like into cells. The cell-penetrating peptide (CPP) has been used to date for intracellular delivery of various low molecular weight compounds, proteins, peptides, RNA, and high molecular weight substances such as DNA. Most of the cell-penetrating peptides are derived from protein-transduction domains or membrane-translocating sequences, and unlike general entry pathways for foreign substances into cells, the cell-penetrating peptide (CPP) is expected to have a key role in delivering even DNA or proteins, which are known to be unable to pass through the cell membrane, into cells without causing damage to the cell membrane.

The fusion peptide of the present invention uses a cell-penetrating peptide, and the cell-penetrating peptide is not particularly limited as long as it enters cells by endocytosis, and is preferably selected from the group consisting of cell-penetrating peptides or mutants thereof shown in Table 4 below.

TABLE 4

| Peptide | References | Sequence | SEQ ID NO: |
|---------|-----------|----------|------------|
| TAT | Takeshima et al., (2003) *J. Biol. Chem.* 278(2), 1310-1315 | YGRKKRRQRRR | 21 |
| TAT $_{(48-60)}$ | Dennison et al., (2007) *Biochem. and Biophy. Res. Comm.* 363, 178 | GRKKRRQRRRPPQ | 22 |
| TAT $_{(49-57)}$ | Baoum et al., (2012) *Int. J. Pharm.* 427, 134-142 | RKKRRQRRR | 23 |
| Penetratin | Derossi et al., (1994) *J. Biol. Chem.* 269(14), 10444-10450 | RQIKIWFQNRRMKWKK | 24 |
| R8 | Chu et al., (2015) *Nanotechnol. Biol. Med.* 11, 435-446 | RRRRRRRR | 25 |
| R9-TAT | Futaki et al., (2001) *J. Biol. Chem.* 276, 5836-5840 | GRRRRRRRRRPPQ | 26 |
| Pep-1 | Deshayes et al., (2008) *Advanced Drug Delivery Reviews*, 60, 537-547 | KETWWETWWTEWSQPKKKRKV | 27 |
| Hph-1 | Choi et al., (2006) *Nat. Med.* 12, 574-579. | YARVRRGPRR | 28 |
| MAP | Wada et al., (2013) *Bioorg. Med. Chem.* 21, 7669-7673 | KLALKLALKALKAALKLA | 29 |
| pVEC | Elmquist et al., (2006) *Biochim. Biophys. Acta.* 1758, 721-729 | LLIILRRRIRKQAHAHSK | 30 |
| MPG | Simeoni, (2003) *Nucleic Acids Res.* 31, 2717-2724 | GALFLGFLGAAGSTMGAWSQPKKKRKV | 31 |
| Transportan | Pae et al., (2014) *J. Controlled Release*, 192, 103-113 | GWTLNSAGYLLGKINLKALAALAKKIL | 32 |
| gH625 | Galdiero et al., (2015) *Biochim. Biophys. Acta (BBA) Biomembr.* 1848, 16-25. | HGLASTLTRWAHYNALIRAF | 33 |
| VP22 | Elliott and O'Hare (1997) Cell, 88, 223-233 | NAKTRRHERRRKLAIER | 34 |

More preferably, the cell-penetrating peptide may be selected from the group consisting of cell-penetrating peptides or variants thereof, and the production and characteristics of the peptide shown in Table 5 below refer to Korean Patent No. 1169030. Most preferably, the cell-penetrating peptide may comprise the amino acid sequence of SEQ ID NO: 38.

TABLE 5

| Peptide | Sequence | SEQ ID NO: |
|---------|----------|------------|
| DS 4 | VQIFRIMRILRILKLARHST | 35 |
| DS 4-1 | RIMRILRILKLARHST | 36 |
| DS4-2 | VQIFRIMRILRILKLAR | 37 |
| DS4-3 | RIMRILRILKLAR | 38 |
| KS4 | FRLVRLLRFLRILLIIS | 39 |
| KS4-1 | FRLVRLLRFLRILL | 40 |
| KS4-2 | RLVRLLRFLR | 41 |
| N1 | RIL | 42 |
| N3 | RILRILRIL | 43 |
| N5 | RILRILRILRILRIL | 44 |
| N7 | RILRILRILRILRILRILRIL | 45 |
| K3 | RIFWVIKLARHFI | 46 |
| C3 | KSLRVLRVLRPLKTIK | 47 |
| C4 | RLFRVMRLVKLLSRG | 48 |
| S2 | RSFRLLRVFKLAKSW | 49 |
| S4 | RVIRLARIGRILRLVKGAKGIR | 50 |
| D1 | RAGRILRILKLAR | 51 |
| D2 | RIMRGLRILKLAR | 52 |
| D3 | RIMRILRLMKLAR | 53 |
| D4 | RIMRILRILKMFR | 54 |
| D5 | RIMRILRALKLAR | 55 |
| D6 | RIMRGMRILKLAR | 56 |
| D7 | RLFRILRILKLAR | 57 |
| D8 | RIMRMVRILKLAR | 58 |
| D9 | RIMRILRLVKLAR | 59 |
| D10 | RIMRILRILKGVR | 60 |
| D11 | RNLRILRILKLAR | 61 |
| D12 | RIMRDIRILKLAR | 62 |
| D13 | RIMRILRELKLAR | 63 |
| D14 | RIMRILRILKQLR | 64 |
| D15 | RIMRILRHMKLAR | 65 |
| D16 | RIMRSVRILKLAR | 66 |
| D17 | RTMRILRILKLAR | 67 |
| D18 | RIMRYARILKLAR | 68 |

TABLE 5-continued

| Peptide | Sequence | SEQ ID NO: |
|---------|----------|------------|
| D19 | RIMRILRQIKLAR | 69 |
| D20 | RIMRILRILKEVR | 70 |

In one embodiment of the present invention, the cell-penetrating peptide of SEQ ID NO: 38 represented by the DS4-3 peptide in Table 5 is selected and used to perform the experiment, and it will be apparent to those skilled in the art that fusions of cell-penetrating peptides other than the actually used cell-penetrating peptide with the peptide of the present invention exert effects similar to those of the present invention.

In the present invention, the AGM peptide-PEG conjugate and the cell-penetrating peptide may be linked through a linker. Preferably, the AGM peptide-PEG conjugate and the cell-penetrating peptide may be linked through a maleimide-carboxy bifunctional linker, but is not limited thereto.

In the present invention, the description of the antiviral composition comprising the AGM peptide-CPP fusion peptide may be the same as that of the antiviral composition comprising the AGM peptide, and the amino acid sequence, AGM peptide-PEG conjugate, multimer and virus type are as defined above.

In another aspect, the present invention is directed to a pharmaceutical composition for preventing or treating viral infections comprising the AGM peptide, the AGM peptide-CPP fusion peptide or the antiviral composition.

In another aspect, the present invention is directed to a method for preventing or treating viral infections comprising administering the peptide, the fusion peptide or the antiviral composition to a subject.

In another aspect, the present invention is directed to the use of the peptide, the fusion peptide or the antiviral composition for preventing or treating viral infections.

In another aspect, the present invention is directed to the use of the peptide, the fusion peptide or the antiviral composition for preparing a drug for preventing or treating viral infections.

In the present invention, since the pharmaceutical composition, method, use and application comprise the AGM peptide, AGM peptide-CPP fusion peptide or antiviral composition according to the present invention, the details of the AGM peptide, AGM peptide-CPP fusion peptide or the antiviral composition will not be described again.

As used herein, the term "prevention" means any action that suppresses viral infections or delays the progression thereof by administration of the AGM peptide, AGM peptide-CPP fusion peptide, or antiviral composition. As used herein, the term "treatment" means any action that ameliorates or completely cures the symptoms of viral infections by administration of the AGM peptide, AGM peptide-CPP fusion peptide, or antiviral composition.

The composition for preventing or treating viral infections according to the present invention may comprise a pharmaceutically effective amount of the AGM peptide, the AGM peptide-CPP fusion peptide, or the antiviral composition alone, or may further comprise one or more pharmaceutically acceptable carriers, excipients, or diluents. The expression "pharmaceutically effective amount" refers to an amount sufficient to prevent, ameliorate, and treat symptoms of viral infections.

In addition, the term "pharmaceutically acceptable" used herein refers to a composition that is physiologically acceptable and does not usually cause allergic reactions such as gastrointestinal disorders and dizziness or similar reactions thereto when administered to humans. Specific examples of the carrier, excipient or diluent comprised in the pharmaceutical composition comprise lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like. In addition, fillers, anti-coagulants, lubricants, wetting agents, flavoring agents, emulsifiers and preservatives may be further comprised. Suitable pharmaceutically acceptable carriers and agents are described in detail in Remington's Pharmaceutical Sciences (19th ed., 1995).

In addition, the pharmaceutical composition of the present invention may comprise one or more known active ingredients having a therapeutic effect on viral infections, along with the AGM peptide, the AGM peptide-CPP fusion peptide, or the antiviral composition.

The composition of the present invention may be formulated using methods known in the art to provide rapid, sustained or delayed release of the active ingredient after administration to mammals. The formulation may be in the form of a powder, granule, tablet, emulsion, syrup, aerosol, soft or hard gelatin capsule, sterile injectable solution, or sterile powder.

The composition according to the present invention may be administered through any of various administration routes, including oral, transdermal, subcutaneous, intravenous or intramuscular administration, the dose of the active ingredient may be appropriately selected according to various factors such as the route of administration, the patient's age, gender and weight, and the severity of the disease of the patient, and the composition for preventing or treating viral infections according to the present invention may be administered in conjunction with a known compound having an effect of preventing, ameliorating or treating symptoms of viral infection.

In the present invention, the viral infection may be caused by a virus against which the antiviral composition exhibits antiviral activity and non-limiting examples thereof include cold, flu (influenza), infectious mononucleosis, cytomegalovirus infections, measles, polio, yellow fever, dengue fever, hepatitis B, hepatitis C, AIDS and Covid-19.

In another aspect, the present invention is directed to a health functional food composition for preventing or ameliorating viral infections comprising the AGM peptide, the AGM peptide-CPP fusion peptide or the antiviral composition.

The functional food of the present invention may be utilized in a variety of applications such as pharmaceuticals, foods, and beverages for preventing oxidation. Examples of functional foods of the present invention include a variety of foods, candy, chocolate, beverages, gum, tea, vitamin complexes, health supplements, and the like, and may be used in the form of powders, granules, tablets, capsules, or beverages.

The antiviral composition of the present invention may be added to food or beverages to prevent or ameliorate viral infections. In this case, the health functional food composition of the present invention is generally added in an amount of 0.01 to 50% by weight, preferably 0.1 to 20% by weight of the total weight of the food, and the health beverage composition is added in an amount of 0.02 to 10 g, preferably 0.3 to 1 g, based on 100 ml of the total weight of the food.

The health beverage composition of the present invention has no particular limitations on the liquid ingredient except that it contains the extract as an essential ingredient in the indicated amount, and may contain various flavors or natural carbohydrates as additional ingredients like conventional beverages. Examples of the natural carbohydrates include monosaccharides such as glucose and fructose, disaccharides such as maltose and sucrose, polysaccharides, for example, common sugars such as dextrins and cyclodextrins, and sugar alcohols such as xylitol, sorbitol, and erythritol. Useful flavoring agents other than those mentioned above include natural flavoring agents (thaumatin, and stevia extracts such as rebaudioside A and glycyrrhizin) and synthetic flavoring agents (such as saccharin and aspartame). The amount of the natural carbohydrate is generally about 1 to 20 g, preferably about 5 to 12 g per 100 ml of the composition of the present invention.

The composition of the present invention may comprise various nutrients, vitamins, electrolytes, flavoring agents such as synthetic flavoring agents and natural flavoring agents, colorants and fillers (such as cheese and chocolate), pectic acid and salts thereof, alginic acid and salts thereof, organic acids, protective colloid thickeners, pH adjusters, stabilizers, preservatives, glycerin, alcohols, and carbonates used in carbonated beverages. In addition, the composition of the present invention may comprise pulp for the production of natural fruit juices, fruit juice beverages and vegetable beverages. These components may be used alone or in combination. The content of these additives is generally selected within the range of 0 to about 20 parts by weight per 100 parts by weight of the composition of the present invention although it is not that important.

In the present invention, since the health functional food composition comprises the AGM peptide, AGM peptide-CPP fusion peptide or antiviral composition according to the present invention, the details of the AGM peptide, AGM peptide-CPP fusion peptide or the antiviral composition will not be described again.

Hereinafter, the present invention will be described in more detail with reference to examples. However, it will be obvious to those skilled in the art that these examples are provided only for illustration of the present invention, and should not be construed as limiting the scope of the present invention.

Example 1: Materials and Methods

Example 1-1: OBOC Library Synthesis

The OBOC library was synthesized on solid-phase Tentagel MB $NH_2$ resin (Rapp Polymere GmbH, Tubingen, Germany). Combinatorial OBOC libraries including random libraries of several millions of beads/ligands were constructed by performing the synthetic method. 5 g of Tentagel MB $NH_2$ resins (200 μm, 520,000 beads/g) were used for the synthesis of approximately 2, 600,000 OBOC libraries. Ligands on the surface of the beads were synthesized by standard solid-phase peptide synthesis using 9-fluorenylmethoxycarbonyl (Fmoc) chemistry and N-hydroxybenzotriazole (HOBt) (GL Biochem, Shanghai, China)/N,N'-diisopropylcarbodiimide (DIC) (GL Biochem) coupling. The coupling completion was determined by the ninhydrin test. Beads were stored in 70% ethanol at 4° C. before use.

Example 1-2: Ethics and Cell Culture

All studies associated with human tissues were pre-approved by the Research Ethics Review Board (IRB) of the Gwangju Institute of Science and Technology (#20191008-BR-48-03-02). All experiments animal were performed in accordance with the guidelines of the Institutional Animal Care and Use Committee (IACUC) of the Gwangju Institute of Science and Technology (GIST-2019-040). All cultures were grown in a humidified incubator maintained at 37° C. in 95% air/5% $CO_2$ atmosphere. The normal human breast cell line MCF-10A was obtained from the American Type Culture Collection and grown in MEGM complete growth medium (MEGM, Lonza, Walkersville, MD) supplemented with bovine pituitary extract (Cambrex Bioscience, Walkersville, MD). Normal human colorectal cell line CCD-18Co was obtained from Korea Cell Line Bank (Seoul, Republic of Korea). Human breast and colorectal cancer cell lines including MCF-7, MDA-MB-231, HT-29 and HCT-116 were obtained from Korea Cell Line Bank. Jurkat T cells were also obtained from the Korea Cell Line Bank. Luciferase-expressing MDA-MB-231 cancer cell line was obtained from PerkinElmer (PerkinElmer, Hopkinton, MA). Each cancer cell line was grown in RPMI1640 (Gibco, Waltham, USA) and DMEM (Gibco, Waltham, USA) supplemented with 10% heat-inactivated fetal bovine serum (FBS) (Gibco), 0.1 mg/ml of streptomycin (Gibco) and 100 units/ml of penicillin (Gibco). Gibco).

Example 1-3: OBOC Library Screening of Cancer-Specific Ligands

Before screening, beads were extensively washed with double distilled water and phosphate buffered saline (PBS; Welgene Inc., Republic of Korea). Cancer cells and normal cells were separated from the culture dish using trypsin/EDTA (Gibco) and washed with the corresponding culture medium. The cells were resuspended at $10^6$ cells/ml and cultured while shaking (60 rpm) in a 37° C. humidified $CO_2$ incubator with OBOC beads in a Petri dish. Beads bound by cells observed with the microscope had the shape of rosettes having central beads covered with one or more cell layers. Under an inverted microscope, positive beads were picked out with a pipette, and treated with guanidine-HCL (8M, 20 minutes) to remove cells and proteins from the bead surface, and secondary screening was performed with normal breast epithelial cells to detect false positive binding. Peptide sequencing was performed by selecting only beads having cell binding in both rounds.

Example 1-4: Serum Stability Test

A peptide stock solution (100 UM) was diluted 10-fold using preheated 100% human serum (Sigma-Aldrich) and incubated at 37° C. for 0, 3, 6, 9 and 24 hours. Peptides in PBS were used as controls. Serum proteins were denatured with urea at a final concentration of 3M at 4° C. for 10 minutes, were precipitated with trichloroacetic acid at a final concentration of 7% (v/v) (4° C. for 10 minutes) and then centrifuged (17,000×g, 10 minutes) to stop the reaction. The supernatant of each sample was recovered and the analytical column was run over 25 minutes at a flow rate of 1 ml/min while monitoring at 215 nm using a linear gradient of 5-65% solvent B (acetonitrile 90% (v/v) with 0.045% (v/v) TFA in solvent A (0.05% (v/v) TFA in $H_2O$)). The elution profile of each peptide was observed with a PBS sample from time 0. The percentage of peptide remaining in the serum-treated sample was determined by comparing the height of the peptide peak obtained at time point 0 with the height of the peptide peak obtained at each time point. Each experiment was performed in triplicate.

Example 1-5: Biotin Pull-Down Assay

The cell lysate (500 μg/ml) was incubated with biotinylated AGM-330 (500 ng/ml) at 4° C. for 12 hours, and then streptavidin beads (Thermo Fisher Scientific, Rockford, IL) were pulled down at room temperature for 1 hour. After incubation, the beads were washed 3 times with wash buffer. Elution buffer was added to the beads, and proteins were extracted from the beads, and finally analyzed by SDS-PAGE. LC-coupled ESI-MS/MS analysis was performed by ProteomeTech (Seoul, Korea) to identify and characterize the proteins derived from the biotin pull-down assay.

Example 1-6: Identification of AGM-330 Binding Domain

NCL constructs including GFP-NCL (residues 1-710), GFP-AN-NCL (residues 322-710) and GFP-AC-NCL (residues 1-321) were produced from human NCL cDNA clones (Addgene), and subcloned into the XhoI and BamHI sites of the pEGFP-$C_2$ vector (Addgene). These vectors were transfected with Lipofectamine 2000 (Invitrogen, Carlsbad, CA, USA) in accordance with the recommendations of the manufacturer. Biotinylated AGM-330 peptide was added to streptavidin beads (Thermo Fisher Scientific) and the mixture was incubated at room temperature for 1 hour with shaking. The beads were washed 3 times with wash buffer. After washing, the beads were added to lysates (300 μl) prepared from transfected cell lysates containing GFP-tagged NCL protein. The reaction mixture was incubated at 4° C. for 12 hours to allow AGM-330 to be bound to the GFP-tagged NCL protein. Then, the beads were washed with wash buffer. An equal volume of 2× electrophoresis sample buffer was added to the beads and heated at 95° C. for 5 minutes to extract proteins from the beads. The proteins were finally analyzed by SDS-PAGE and immunoblot analysis.

Example 1-7: Purification of NCL from Jurkat Cells $1.0 \times 10^9$ Jurkat cells were lysed in the presence of 25 ml of 20 mM Tris/HCl, pH 7.5, 150 mM NaCl, 5 mM of $MgCl_2$, 5 mM β-mercaptoethanol, 0.5% (v/v) Triton X-100, 1 mM marimastat (AdooQ Bioscience, Irvine, CA, USA), and a protease inhibitor cocktail (Millipore, Billerica, MA, USA) at 4° C. for 1 hour to prepare NCL. v) Triton X-100, 1 mM Marimastat (AdooQ Bioscience, Irvine, CA, USA), protease inhibitor cocktail (Millipore, Billerica, MA, USA). Nuclei were pelleted by centrifugation at 1,200×g for 5 minutes, and the supernatant was centrifuged at 12,000×g for 30 min and then stored at −80° C. A rapid two-step chromatographic procedure was used to purify NCL from nucleus-free extracts. All steps were performed at 4° C. using ice-cold buffers and columns in the presence of 1 mM marimastat and complete protease inhibitor cocktail. Cytoplasmic extracts from Jurkat cells (25 ml) were diluted 10× with 20 mM sodium phosphate, pH 7.0, and passed through a 5 ml Mono Q 5/50 GL column (Sigma-Aldrich). The column was washed with 150 ml of 20 mM sodium phosphate, pH 7.0, and the adsorbed protein was eluted with 10 ml of the same buffer containing 1M NaCl. The eluate was diluted 10-fold with 50 mM Tris/HCl, pH 7.9, 5 mM $MgCl_2$, 0.1 mM EDTA, and 1 mM β-mercaptoethanol (buffer A), and loaded onto a 1 ml HiFiQ heparin HP column (Protein Ark, UK) equilibrated with the same buffer. The gel was washed with 20 ml of buffer A containing 0.2 M ammonium sulfate, and the protein was eluted in 50 µl fractions with 2 ml of buffer A containing 0.6 M ammonium sulfate. The NCL was collected and dialyzed against PBS containing 1 mM marimastat for 2 hours at 4° C., and then stored at −80° C. The presence of purified NCL as a single 105 kDa protein band was determined by further controlling the 10% SDS acrylamide gel stained with Coomassie blue. Two 70 and 50 kDa protein bands corresponding to partial degradation products of NCL were detected in amounts of less than 10% of the total protein.

Example 1-8: Binding Affinity

The binding affinity of AGM-330 was tested by surface plasmon resonance (SPR) spectroscopy (Biacore T-200). The recombinant nucleolin protein was immobilized on a CM5 sensor chip and treated with AGM-330 at each concentration (20 nM-2.5 µM), the sensogram thereof was analyzed, and $K_D$ was determined.

Example 1-9: Statistical Analysis

All statistical data were expressed as meantSD (n=3). Statistical comparison between two groups was determined by Student's t test and comparison between multiple groups was determined by one-way ANOVA with Dunnett's multiple comparison. For in vivo experiments, the number of mice is indicated in each legend. Log-rank test was used for Kaplan-Meier analyses. *,  and * indicate P<0.05, P<0.01 and P<0.001, respectively.

Example 2: Identification and Characterization of Cancer-Targeting Peptide Ligands by OBOC Combinatorial Screening and MAP Synthesis To identify novel cancer-specific peptide ligands, 2,600,000 libraries were synthesized using 5 g of Tentagel MB NH$_2$ resins (200 µm, 520,000 beads/g, FIG. 3). Libraries of peptides listed in beads (50,000 to 100,000 beads were used at one time) was mixed with a human breast cancer cell line (MDA-MB-231). A total of ~1,000,000 beads was screened, and 8 positive beads were detected and isolated for microsequencing. Three of these eight peptides (AGM-330, AGM-331 and AGM-332) had strong preferential binding to MDA-MB-231, and did not bind to a normal human breast cell line (MCF-10A) or weakly bound thereto (FIG. 4 in A and B thereof). Then, these three peptides were labeled with fluorescein isothiocyanate (FITC) and the ability thereof to bind to MDA-MB-231 cells was determined. Compared to AGM-331 and AGM-332, AGM-330 exhibited the strongest fluorescence signal (FIG. 4 in C thereof). To obtain the results of screening by cell-growth-on-bead assay and fluorescence imaging, AGM-330 was re-synthesized from Tentagel MB NH$_2$ resin. As a result of cell growth bead analysis, AGM-330 beads were completely covered with human breast cancer cell lines (MCF7 and MDA-MB-231) and human colorectal cancer cell lines (HT-29 and HCT-116) within 15 minutes (FIG. 4 in D thereof). Meanwhile, AGM-331 and AGM-332 were relatively non-specific and bound to human normal breast cell line (MCF-10A) and human normal colorectal cell line (CCD-18Co). In addition, AGM-330 bound very weakly to MCF-10A or CCD-18Co cells or did not bind thereto at all, and thus are highly suitable for candidates for both imaging and therapeutic targeting agents.

Currently, the use of peptides as therapeutics has been largely limited due to low stability thereof: peptides are degraded in vivo mainly by proteases and peptidases (Bottger R, et al. PLOS One. 2017; 12: e0178943). In the present invention, in order to improve the stability of the peptide ligand, AGM-330 in the form of a MAP dendrimer was synthesized, which may exhibit increased stability due to acquired resistance to protease and peptidase activity. The synthesis of AGM-330 (FIG. 4 in E thereof) was initiated in the presence of 20% piperidine and DMF by Fmoc-Cys (Trt) Wang resin (1) and Fmoc-Lys (Fmoc)-OH to produce lysine core-conjugated Wang resin (2,3). Then, Fmoc- and Trt-protected AGM-330 (4) was prepared by treatment with RHGAMVYLK-PEG12-OH in the presence of 20% piperidine. The Fmoc- and Trt-protecting groups of AGM-330 (4) were rapidly removed by piperidine in DMF to prepare AGM-330 (5).

In order to improve the in vivo stability and binding affinity of the selected peptide ligand AGM-330, dimers and tetramers were synthetized by multiple antigen peptide (MAP) synthesis.

In order to determine whether or not the stability of the peptide is enhanced, the in vivo half-life of the peptide was analyzed. 2 mg/kg of AGM-330m, AGM-330d, or AGM-330t was injected through the tail vein of C57BL/6 mice and the remaining serum peptide was immediately immobilized on an ELISA plate with an anti-AGM-330 antibody. The absorbance was measured at a wavelength of 450 nm using a VersaMax ELISA plate reader (Molecular Devices) and pharmacokinetics were analyzed with the phoenix WinNonlin 8.1 (Pharsight Corporation, Mountain View, CA, USA) program. The result of analysis showed that the half-lives ($T_{1/2}$) of AGM-330m, AGM-330d, and AGM-330t were 0.42±0.33 hours, 1.82±0.36 hours, and 9.43±1.21 hours, respectively, and the maximum concentration time ($T_{max}$) in blood was 0.167 hours. The maximum plasma concentrations ($C_{max}$) thereof were 1.27±0.12 µg/mL, 1.71±0.11 ug/mL, and 1.875±0.67 ug/mL, respectively, and the areas under the curve (AUC) thereof were 0.64±0.09 µg/h/mL, 1.77±0.12 ug/h/mL, and 21.42±0.81 ug/h/mL, respectively (FIG. 5). The result showed that tetrameric AGM-330 (AGM-330t) has higher stability than monomeric or dimeric peptides.

Then, in order to determine whether or not MAP ligands selectively bind to cancer cells, cancer cells treated with FITC-labeled AGM-330 (AGM-330-FITC) were compared with untreated cells. AGM-330-FITC was incubated along with cells ($1×10^5$) at 37° C. in a serum-free medium for 2 hours to keep the conjugates intact. Then, native fluorescent peptide-treated cells were compared with untreated cells and measured based on changes in mean fluorescence intensity (MFI) (FIG. 4 in F thereof). As a result, AGM-330-FITC exhibited significant cancer cell binding affinity to MCF-7, MDA-MB-231, HT-29, and HCT-116, which is supported by a relative increase in MFI of treated cells compared to untreated cells. In contrast, after incubation 2 hours, the conjugate had significantly reduced binding affinity to normal cells, including MCF-10A and CCD-18Co, while having strong preferential binding affinity to cancer cells.

Example 3: NCL, Potent Regulator of Cancer Cell Growth as Potential Target of AGM-330

In order to identify the unknown target protein of AGM-330, affinity column chromatography and mass spectrometry-based proteomics approaches were used to identify AGM-330-interactive proteins from cell lysates of MDA-MB-231 cells (FIG. 6 in A thereof). After affinity column chromatography, SDS-PAGE analysis showed that several distinct protein bands (55-100 kDa) were present only in the elution fraction (FIG. 6 in B thereof). Six proteins were identified using LC-MS/MS analysis, and peptide identification of these excised bands showed that one of the major protein bands at 100 kDa was characterized as nucleolin (NCL). NCL consists of 710 amino acids and 22 other peptide fragments identified by LC-MS/MS analysis corresponded to the amino acid sequence of NCL (total score 881 and 24% sequence coverage for human NCL (accession number: gi189306) in NCBI database) (FIG. 6 in C and D thereof). In addition, immunoblot analysis using an anti-NCL antibody further showed the enrichment of NCL in the eluate from the AGM-330 affinity column (FIG. 6 in E thereof). Thus, proteomic studies suggest that NCL is an AGM-330-interacting protein.

In order to determine the binding affinity of AGM-330 to NCL, a surface plasmon resonance (SPR) test was performed using AGM-330. As shown in FIG. 7, the Ka was about 57.7 nM, indicating very high binding affinity to NCL.

A biotin pull-down assay was used to determine domains involved in the interaction between AGM-330 and NCL. NCL mutants were pulled down using biotinylated AGM-330 (AGM-330-Biotin) as a bait. Several deletion mutants of NCL have been produced. Cell extracts were prepared from HEK293T cells transfected with expression vectors encoding wild-type and various NCL mutants, NCL1 (1-710), NCL2 (323-710) and NCL3 (1-322), all fused to GFP. AGM-330-biotin pulled down wild-type NCL1 (1-710) and NCL3 (1-322), but NCL2 (323-710) did not pull down them (FIG. 6 in F thereof). These results indicate that the N-terminal region (1-322) of NCL is important for AGM-330 binding. To further identify the direct interaction between AGM-330 and NCL, purified NCL and AGM-330-biotin were used in biotin pull-down assay. Enrichment of NCL in the elution fraction was confirmed through immunoblot analysis using an anti-NCL antibody (FIG. 8). Overall, AGM-330 directly interacts with NCL.

Example 4: Synthesis of Fusion Peptide in which AGM-330 is Fused with CPP

In order to increase the cell permeability of AGM-330, a cell-penetrating peptide (CPP) was fused with AGM-330 to prepare a fusion peptide.

When AGM-330t is reacted with maleimide-bound CPP (RIMRILILKLAR; SEQ ID NO: 38) at a pH of 7.0 to 7.5, an AGM-330t-mCPP fusion peptide is synthesized by fusing with a thiol group, a functional group of AGM-330t, through thiol-maleimide reaction (FIG. 9).

The result of HPLC and MS analysis of the prepared AGM-330t-mCPP fusion peptide showed that the retention time was 23.2 minutes and the molecular weight was 7,876 Da. The results of analysis of AGM-330t and maleimide-mCPP are shown in FIG. 10.

Example 5: Confirmation of Influenza a Virus (IAV) Inhibitory Effect of AGM-330 Through In Vitro Experiments Western blot analysis was performed to detect the decrease in viral antigen content by inhibition of influenza A virus proliferation by AGM-330d-mCPP and AGM-330t-mCPP. First, each well of a 12-well plate containing confluently grown A549 cells (lung cancer cell line, American Type Culture Collection [ATCC]) was washed twice with DPBS (Dulbecco's phosphate-buffered saline), and the washing solution was discarded. Then, the cells were inoculated with influenza A virus (IAV, Puerto Rico/8 (PR8) (H1N1), ATCC) at 0.1 MOI FFU/mL and incubated (adsorbed) for 1 hour. After virus adsorption, the cells were washed twice again with DPBS and incubated in a preservation medium containing a predetermined concentration of the compound, 1 µg/mL of TPCK (N-tosyl-L-phenylalanine chloromethyl ketone)-treated trypsin, 1% penicillin, and 1% streptomycin at 36° C. for 24 hours. Then, each plate was frozen and thawed three times to detach cells from each well and Western blotting was performed using a rabbit polyclonal primary antibody against influenza A virus PB1 antigen and a HRP-conjugated goat anti-rabbit IgG secondary antibody. In addition, in order to measure the amount of viral antigen reduced by AGM-380d-mCPP and AGM-380t-mCPP, western blotting was performed using an HRP-conjugated goat anti-mouse IgG secondary antibody and a mouse monoclonal primary antibody against the host protein, GAPDH (glyceraldehyde 3-phosphate dehydrogenase) (FIG. 11A).

An immunofluorescence assay was performed to detect the decrease in the amount of viral antigen in the cytoplasm caused by the inhibition of influenza A virus proliferation by AGM-330d-mCPP and AGM-330t-mCPP. First, each chamber of an 8-well chamber slide containing confluently grown A549 cells was washed twice with DPBS and the washing solution was discarded. Then, the cells were inoculated with influenza A virus (IAV, Puerto Rico/8 (PR8) (H1N1), ATCC) at 0.1 MOI FFU/mL, and incubated (adsorbed) for 1 hour. After virus adsorption, the cells twice with DPBS and incubated in a preservation medium containing a predetermined concentration of the compound, 1 µg/mL of TPCK (N-tosyl-L-phenylalanine chloromethyl ketone)-treated trypsin, 1% penicillin, and 1% streptomycin at 36° C. for 8 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a mouse monoclonal primary antibody against an influenza A virus M2 antigen was added to each chamber and allowed to stand at 4° C. for 12 hours. Then, each chamber was washed three times with phosphate buffered saline (pH 7.4), the washing solution was discarded, and a dilution of a goat anti-mouse IgG polyclonal antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and observed with an LSM 800 confocal microscope (FIG. 11B).

Real-time PCR was performed to detect the number of viral genomes reduced by inhibition of influenza A virus proliferation by AGM-330d-mCPP and AGM-330t-mCPP. First, each well of a 12-well plate containing A549 cells grown confluently was washed twice with DPBS (Dulbecco's phosphate-buffered saline) and then the washing solution was discarded. Then, the cells were inoculated with influenza A virus (IAV, Puerto Rico/8 (PR8) (H1N1), ATCC) at 0.1 MOI FFU/mL, and incubated (adsorbed) for 1 hour. After virus adsorption, the cells were washed twice with DPBS and incubated in the preservation medium containing a predetermined amount of the compound, 1 µg/mL of TPCK (N-tosyl-L-phenylalanine chloromethyl ketone)-treated trypsin, 1% penicillin, and 1% streptomycin for 24 hours. Then, each plate was frozen and thawed three times to detach cells from each well and then RNA was extracted using an RNeasy mini kit (Qiagen). cDNA was synthesized from the extracted RNA using a TOPscript™ CDNA synthesis kit (Enzynomics) containing random hexamer and poly(rA)-oligo(dT). Then, the synthesized CDNA, and a forward primer (5'-CTGCCAGAAGACAATGAACC-3', SEQ ID NO: 71) and a reverse primer (5'-GGCCAT-TGCTTCCAATACAC-3', SEQ ID NO: 72) specific for PB1 of influenza A virus were inserted into a TOPreal™ qPCR 2× PreMix (Enzynomics) solution, and real-time PCR was performed in a LineGene 9600 Plus real-time PCR detection system (Bioer, Hangzhou, China) (FIG. 11C).

A cell culture immunofluorescence assay was performed to detect reduced production of influenza A virus progeny virus by AGM-330d-mCPP and AGM-330t-mCPP. First, each well of a 12-well plate containing confluently grown A549 cells was washed twice with DPBS and the washing solution was discarded. Then, the cells were inoculated with influenza A virus (IAV, Puerto Rico/8 (PR8) (H1N1), ATCC) at 0.1 MOI FFU/mL, and incubated (adsorbed) for 1 hour. After virus adsorption, the cells were washed twice with DPBS and incubated in a preservation medium containing a predetermined concentration of the compound, 1 µg/mL of TPCK (N-tosyl-L-phenylalanine chloromethyl ketone)-treated trypsin, 1% penicillin, and 1% streptomycin for 8 hours. Then, each plate was frozen and thawed three times to detach cells from each well, and the supernatant was serially diluted 10×, and then seeded on each well of a 96-well plate containing A549 cells grown confluently. Then, each well was washed twice with phosphate buffered saline (pH 7.4) and the washing solution was discarded. 4% paraformaldehyde fixative was added to each well and immobilization was performed at 20° C. for 10 minutes. In order to increase cell permeability, each chamber was treated with 0.2% Triton-X at 20° C. for 10 minutes. Then, each well was washed twice with phosphate buffered saline (pH 7.4), and the washing solution was discarded. Then, a mouse monoclonal primary antibody against an influenza A virus nucleoprotein (NP) antigen was added to each well and allowed to react at 4° C. for 12 hours. Each chamber was washed three times with phosphate-buffered saline (pH 7.4), the washing solution was discarded, and a dilution of a goat anti-mouse IgG polyclonal antibody conjugated with Alexa Fluor 488 was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 11D).

As a result, the amount of viral protein (PB1), the amount of intracellular viral antigen (M2), the number of viral genomes, and the number of viral progeny decreased depending on the concentration of the treated NCL target peptide ligand (FIG. 11). Therefore, it was verified that the NCL-targeting peptide ligand inhibited influenza A virus infection.

Example 6: Confirmation of Bovine Coronavirus (BCoV) Inhibitory Effect of AGM-330 Through In Vitro Experiments Western blot analysis was performed to detect the decrease in viral antigen content by inhibition of bovine coronavirus proliferation by AGM-330d-mCPP and AGM-330t-mCPP. First, each well of a 12-well plate containing confluently grown HRT-18G cells (human cororectal adeno-carcinoma cell line, ATCC) was washed twice with DPBS (Dulbecco's phosphate-buffered saline), and the washing solution was discarded. Then, the cells were inoculated with bovine coronavirus (BCoV, KWD20 strain ATCC) at 0.1 MOI FFU/mL and incubated (adsorbed) for 1 hour. After virus adsorption, the cells were washed twice again with DPBS and incubated in a preservation medium containing a predetermined concentration of the compound, 5 µg/mL of porcine pancreatin, 1% penicillin, and 1% streptomycin at 36° C. for 36 hours. Then, each plate was frozen and thawed three times to detach cells from each well and Western blotting was performed using a mouse monoclonal primary antibody: a bovine coronavirus spike(S) antigen and a HRP-conjugated goat anti-mouse IgG secondary antibody. In addition, in order to measure the amount of viral antigen reduced by AGM-330d-mCPP and AGM-330t-mCPP, western blotting was performed using an HRP-conjugated goat anti-mouse IgG secondary antibody and a mouse monoclonal primary antibody against the host protein, GAPDH (glyceraldehyde 3-phosphate dehydrogenase) (FIG. 12A).

An immunofluorescence assay was performed to detect the decrease in the amount of viral antigen in the cytoplasm caused by the inhibition of bovine coronavirus proliferation by AGM-330d-mCPP and AGM-330t-mCPP. First, each chamber of an 8-well chamber slide containing confluently grown HRT-18G cells was washed twice with DPBS and the washing solution was discarded. Then, the cells were inoculated with bovine coronavirus (BCoV, KWD20 strain, ATCC) at 0.1 MOI FFU/mL, and incubated (adsorbed) for 1 hour. After virus adsorption, the cells were washed twice with DPBS and incubated in a preservation medium containing a predetermined concentration of the compound, 5 µg/mL of porcine pancreatin, 1% penicillin, and 1% streptomycin at 36° C. for 24 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a mouse monoclonal primary antibody against a bovine coronavirus spike(S) antigen was added to each chamber and allowed to stand at 4° C. for 12 hours. Then, each chamber was washed three times with phosphate buffered saline (pH 7.4), the washing solution was discarded, and a dilution of a goat anti-mouse IgG polyclonal antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and then observed with an LSM 800 confocal microscope (FIG. 12B).

Real-time PCR was performed to detect the number of viral genomes reduced by inhibition of bovine coronavirus proliferation by AGM-330d-mCPP and AGM-330t-mCPP. First, each well of a 12-well plate containing HRT-18G cells grown confluently was washed twice with DPBS (Dulbecco's phosphate-buffered saline) and then the washing solution was discarded. Then, the cells were inoculated with bovine coronavirus (BCoV, KWD20 strain, ATCC) at 0.1 MOI FFU/mL and incubated (adsorbed) for 1 hour. After virus adsorption, the cells were washed twice with DPBS and incubated in a preservation medium containing a predetermined amount of the compound, 5 µg/mL of porcine pancreatin, 1% penicillin, and 1% streptomycin for 24 hours. Then, each plate was frozen and thawed three times to detach cells from each well and then RNA was extracted using an RNeasy mini kit (Qiagen). CDNA was synthesized from the extracted RNA using a TOPscript™ cDNA synthesis kit (Enzynomics) containing random hexamer and poly(rA)-oligo (dT). Then, the synthesized cDNA, and a forward primer (5'-TGGATCAAGATTAGAGTTGGC-3', SEQ ID NO: 73) and a reverse primer (5'-CCTTGTCCAT-TCTTCTGACC-3', SEQ ID NO: 74) specific for N genes of bovine coronavirus were inserted into TOPreal™ qPCR 2× PreMix (Enzynomics) solution, and real-time PCR was performed in a LineGene 9600 Plus real-time PCR detection system (Bioer, Hangzhou, China) (FIG. 12C).

A cell culture immunofluorescence assay was performed to detect reduced production of bovine coronavirus progeny virus by AGM-330d-mCPP and AGM-330t-mCPP. First, each well of a 12-well plate containing confluently grown HRT-18G cells was washed twice with DPBS and the washing solution was discarded. Then, the cells were inoculated with bovine coronavirus (BCoV, KWD20 strain, ATCC) at 0.1 MOI FFU/mL, and incubated (adsorbed) for 1 hour. After virus adsorption, the cells were washed twice with DPBS and incubated in a preservation medium containing a predetermined concentration of the compound, 5 μg/mL of porcine pancreatin, 1% penicillin, and 1% streptomycin for 8 hours. Then, each plate was frozen and thawed three times to detach cells from each well, and the supernatant was serially diluted 10×, and then seeded on each well of a 96-well plate containing HRT-18G cells grown confluently. Then, each well was washed twice with phosphate buffered saline (pH 7.4) and the washing solution was discarded. 4% paraformaldehyde fixative was added to each well and immobilization was performed at 20° C. for 10 minutes. In order to increase cell permeability, each chamber was treated with 0.2% Triton-X at 20° C. for 10 minutes. Then, each well was washed twice with phosphate buffered saline (pH 7.4), and the washing solution was discarded. Then, a mouse monoclonal primary antibody against a bovine coronavirus spike(S) antigen was added to each well and allowed to react at 4° C. for 12 hours. Each chamber was washed three times with phosphate-buffered saline (pH 7.4), the washing solution was discarded, and a dilution of a goat anti-mouse IgG polyclonal antibody conjugated with Alexa Fluor 488 was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 12D).

As a result, the amount of viral protein(S), the amount of intracellular viral antigen(S), the number of viral genomes, and the number of viral progeny decreased depending on the concentration of the treated NCL target peptide ligand (FIG. 12). Therefore, it was verified that the NCL-targeting peptide inhibited bovine ligand coronavirus infection.

Example 7: Confirmation of Porcine Epidemic Diarrhea Virus (PEDV) Inhibitory Effect of AGM-330 Through In Vitro Experiments Western blot analysis was performed to detect the decrease in viral antigen content by inhibition of porcine epidemic diarrhea virus proliferation by AGM-330d-mCPP and AGM-330t-mCPP. First, each well of a 12-well plate containing confluently grown Vero E6 cells (African green monkey kidney epithelial cell line, ATCC) was washed twice with DPBS (Dulbecco's phosphate-buffered saline), and the washing solution was discarded. Then, the cells were inoculated with porcine epidemic diarrhea virus (PEDV, QIAP1401, a kind gift from the Animal and Plant Quarantine Agency, Korea) at 0.1 MOI FFU/mL and incubated (adsorbed) for 1 hour. After virus adsorption, the cells were washed twice again with DPBS and incubated in a preservation medium containing a predetermined concentration of the compound, 3 μg/mL of porcine pancreatic trypsin, 1% penicillin, and 1% streptomycin at 36° C. for 36 hours. Then, each plate was frozen and thawed three times to detach cells from each well and Western blotting was performed using a mouse monoclonal primary antibody against a porcine epidemic diarrhea virus nucleocapsid (N) antigen and an HRP-conjugated goat anti-mouse IgG secondary antibody. In addition, in order to measure the amount of viral antigen reduced by AGM-330d-mCPP and AGM-330t-mCPP, western blotting was performed using an HRP-conjugated goat anti-mouse IgG secondary antibody and a mouse monoclonal primary antibody against the host protein, GAPDH (glyceraldehyde 3-phosphate dehydrogenase) (FIG. 13A).

An immunofluorescence assay was performed to detect the decrease in the amount of viral antigen in the cytoplasm caused by the inhibition of porcine epidemic diarrhea virus proliferation by AGM-330d-mCPP and AGM-330t-mCPP. First, each chamber of an 8-well chamber slide containing confluently grown Vero E6 cells was washed twice with DPBS and the washing solution was discarded. Then, the cells were inoculated with porcine epidemic diarrhea virus (PEDV, QIAP1401, a kind gift from the Animal and Plant Quarantine Agency, Korea) at 0.1 MOI FFU/mL, and incubated (adsorbed) for 1 hour. After virus adsorption, the cells were washed twice with DPBS and incubated in a preservation medium containing a predetermined concentration of the compound, 3 μg/mL of porcine pancreatic trypsin, 1% penicillin, and 1% streptomycin at 36° C. for 24 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a mouse monoclonal primary antibody against a porcine epidemic diarrhea virus nucleocapsid (N) antigen was added to each chamber and allowed to stand at 4° C. for 12 hours. Then, each chamber was washed three times with phosphate buffered saline (pH 7.4), the washing solution was discarded, and a dilution of a goat anti-mouse IgG polyclonal antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and observed with an LSM 800 confocal microscope (FIG. 13B).

Real-time PCR was performed to detect the number of viral genomes reduced by inhibition of porcine epidemic diarrhea virus proliferation by AGM-330d-mCPP and AGM-330t-mCPP. First, each well of a 12-well plate containing Vero E6 cells grown confluently was washed twice with DPBS (Dulbecco's phosphate-buffered saline) and then the washing solution was discarded. Then, the cells were inoculated with porcine epidemic diarrhea virus (PEDV, QIAP1401, a kind gift from the Animal and Plant Quarantine Agency, Korea) at 0.1 MOI FFU/mL, and incubated (adsorbed) for 1 hour. After virus adsorption, the cells were washed twice with DPBS and incubated in the preservation medium containing a predetermined amount of the compound, 3 µg/mL of porcine pancreatic trypsin, 1% penicillin, and 1% streptomycin for 36 hours. Then, each plate was frozen and thawed three times to detach cells from each well and then RNA was extracted using an RNeasy mini kit (Qiagen). CDNA was synthesized from the extracted RNA using a TOPscript™ CDNA synthesis kit (Enzynomics) containing random hexamer and poly(rA)-oligo (dT). Then, the synthesized cDNA, and a forward primer (5'-GC-TATGCTCAGATCGCCAGT-3', SEQ ID NO: 75) and a reverse primer (5'-TCTCGTAAGAGTCCGCTAGCTC-3', SEQ ID NO: 76) specific for the N gene of porcine epidemic diarrhea virus were inserted into a TOPreal™ qPCR 2× PreMix (Enzynomics) solution, and real-time PCR was performed in a LineGene 9600 Plus real-time PCR detection system (Bioer, Hangzhou, China) (FIG. 13C).

A cell culture immunofluorescence assay was performed to detect reduced production of porcine epidemic diarrhea virus by AGM-330d-mCPP and AGM-330t-mCPP. First, each well of a 12-well plate containing confluently grown Vero E6 cells was washed twice with DPBS and the washing solution was discarded. Then, the cells were inoculated with a porcine epidemic diarrhea virus (PEDV, QIAP1401, a kind gift from the Animal and Plant Quarantine Agency, Korea) at 0.1 MOI FFU/mL, and incubated (adsorbed) for 1 hour. After virus adsorption, the cells were washed twice with DPBS and incubated in a preservation medium containing a predetermined concentration of the compound, 3 µg/mL of porcine pancreatic trypsin, 1% penicillin, and 1% streptomycin for 18 hours. Then, each plate was frozen and thawed three times to detach cells from each well, and the supernatant was serially diluted 10×, and then seeded on each well of a 96-well plate containing HRT-18G cells grown confluently. Then, each well was washed twice with phosphate buffered saline (pH 7.4) and the washing solution was discarded. 4% paraformaldehyde fixative was added to each well and immobilization was performed at 20° C. for 10 minutes. In order to increase cell permeability, each chamber was treated with 0.2% Triton-X at 20° C. for 10 minutes. Then, each well was washed twice with phosphate buffered saline (pH 7.4), and the washing solution was discarded. Then, a mouse monoclonal primary antibody against a porcine epidemic diarrhea virus nucleocapsid (N) antigen was added to each well and allowed to react at 4° C. for 12 hours. Each chamber was washed three times with phosphate-buffered saline (pH 7.4), the washing solution was discarded, and a dilution of a goat anti-mouse IgG polyclonal antibody conjugated with Alexa Fluor 488 was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 13D).

As a result, the amount of viral protein (N), the amount of intracellular viral antigen (N), the number of viral genomes, and the number of viral progeny decreased depending on the concentration of the treated NCL target peptide ligand (FIG. 13). Therefore, it was verified that the NCL-targeting peptide ligand inhibited PEDV infection.

Example 8: Confirmation of Bovine Rotavirus (RVA) Inhibitory Effect of AGM-330 Through In Vitro Experiments Western blot analysis was performed to detect the decrease in viral antigen content by inhibition of bovine rotavirus proliferation by AGM-330d-mCPP and AGM-330t-mCPP. First, each well of a 12-well plate containing confluently grown MA104 cells (African green monkey kidney epithelial cell line, ATCC) was washed twice with DPBS (Dulbecco's phosphate-buffered saline) and the washing solution was discarded. Then, the cells were inoculated with 10 µg/mL of bovine species A rotavirus activated with crystalized trypsin (RVA, NCDV strain, ATCC) at 0.1 MOI FFU/mL and incubated (adsorbed) for 1 hour. After virus adsorption, the cells were washed twice again with DPBS and incubated in a preservation medium containing a predetermined concentration of the compound, 1 µg/mL of crystalized trypsin, 1% penicillin, and 1% streptomycin at 36° C. for 12 hours. Then, each plate was frozen and thawed three times to detach cells from each well and Western blotting was performed using a mouse monoclonal primary antibody against a species A rotavirus VP6 antigen and an HRP-conjugated goat anti-mouse IgG secondary antibody. In addition, in order to measure the amount of viral antigen reduced by AGM-330d-mCPP and AGM-330t-mCPP, western blotting was performed using an HRP-conjugated goat anti-mouse IgG secondary antibody and a mouse monoclonal primary antibody against the host protein, GAPDH (glyceraldehyde 3-phosphate dehydrogenase) (FIG. 14A).

An immunofluorescence assay was performed to detect the decrease in the amount of viral antigen in the cytoplasm caused by the inhibition of bovine rotavirus proliferation by AGM-330d-mCPP and AGM-330t-mCPP. First, each chamber of an 8-well chamber slide containing confluently grown MA104 cells was washed twice with DPBS and the washing solution was discarded. Then, the cells were inoculated with 10 µg/mL of bovine species A rotavirus activated with crystalized trypsin (RVA, NCDV strain, ATCC) at 0.1 MOI FFU/mL, and incubated (adsorbed) for 1 hour. After virus adsorption, the cells were washed twice with DPBS and incubated in a preservation medium containing a predetermined concentration of the compound, 1 µg/mL of crystalized trypsin, 1% penicillin, and 1% streptomycin at 36° C. for 8 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a mouse monoclonal primary antibody against a species A rotavirus VP6 antigen was added to each chamber and allowed to stand at 4° C. for 12 hours. Then, each chamber was washed three times with phosphate buffered saline (pH 7.4), the washing solution was discarded, and a dilution of a goat anti-mouse IgG polyclonal antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and observed with an LSM 800 confocal microscope (FIG. 14B).

Real-time PCR was performed to detect the number of viral genomes reduced by inhibition of bovine rotavirus proliferation by AGM-330d-mCPP and AGM-330t-mCPP. First, each well of a 12-well plate containing MA104 cells grown confluently was washed twice with DPBS (Dulbecco's phosphate-buffered saline) and then the washing solution was discarded. Then, the cells were inoculated with 10 µg/mL of bovine species A rotavirus activated with crystalized trypsin (RVA, NCDV strain, ATCC) at 0.1 MOI FFU/ mL, and incubated (adsorbed) for 1 hour. After virus adsorption, the cells were washed twice with DPBS and incubated in the preservation medium containing a predetermined amount of the compound, 1 μg/mL of crystalized trypsin, 1% penicillin, and 1% streptomycin at 36° C. for 12 hours. Then, each plate was frozen and thawed three times to detach cells from each well and then RNA was extracted using an RNeasy mini kit (Qiagen). CDNA was synthesized from the extracted RNA using a TOPscript™ CDNA synthesis kit (Enzynomics) containing random hexamer and poly(rA)-oligo (dT). Then, the synthesized cDNA, and a forward primer (5'-TAGACCAAATAACGTTGAAGTTGA-3', SEQ ID NO: 77) and a reverse primer (5'-GATT-CACAAACTGCAGATTCAA-3', SEQ ID NO: 78) specific for rotavirus VP6 genes were inserted into a TOPreal™ qPCR 2× PreMix (Enzynomics) solution, and real-time PCR was performed in a LineGene 9600 Plus real-time PCR detection system (Bioer, Hangzhou, China) (FIG. 14C).

A cell culture immunofluorescence assay was performed to detect reduced production of bovine rotavirus progeny virus by AGM-330d-mCPP and AGM-330t-mCPP. First, each well of a 12-well plate containing confluently grown MA104 cells was washed twice with DPBS and the washing solution was discarded. Then, the cells were inoculated with 10 μg/mL of bovine species A rotavirus activated with crystalized trypsin (RVA, NCDV strain, ATCC) at 0.1 MOI FFU/mL, and incubated (adsorbed) for 1 hour. After virus adsorption, the cells were washed twice with DPBS and incubated n a preservation medium containing a predetermined concentration of the compound, 1 μg/mL of crystalized trypsin, 1% penicillin, and 1% streptomycin at 36° C. for 8 hours. Then, each plate was frozen and thawed three times to detach cells from each well, and the supernatant was serially diluted 10×, and then seeded on each well of a 96-well plate containing MA104 cells grown confluently. Then, each well was washed twice with phosphate buffered saline (pH 7.4) and the washing solution was discarded. 4% paraformaldehyde fixative was added to each well and immobilization was performed at 20° C. for 10 minutes. In order to increase cell permeability, each well was treated with 0.2% Triton-X at 20° C. for 10 minutes. Then, each well was washed twice with phosphate buffered saline (pH 7.4), and the washing solution was discarded. Then, a goat polyclonal primary antibody against a species A rotavirus VP6 antigen was added to each well and allowed to react at 4° C. for 8 hours. Each chamber was washed three times with phosphate-buffered saline (pH 7.4), the washing solution was discarded, and a dilution of a rabbit anti-goat IgG polyclonal antibody conjugated with fluorescein isothiocyanate (FITC) was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 14D).

As a result, the amount of viral protein (VP6), the amount of intracellular viral antigen (VP6), the number of viral genomes, and the number of viral progeny decreased depending on the concentration of the treated NCL target peptide ligand (FIG. 14). Therefore, it was verified that the NCL-targeting peptide ligand inhibited bovine rotavirus infection.

Example 9: Confirmation of Porcine Reproductive and Respiratory Syndrome Virus (PRRSV) Inhibitory Effect of AGM-330 Through In Vitro Experiments Western blot analysis was performed to detect the decrease in viral antigen content by inhibition of porcine reproductive and respiratory syndrome virus proliferation by AGM-330d-mCPP and AGM-330t-mCPP. First, each well of a 12-well plate containing confluently grown MARC-145 cells (African green monkey kidney epithelial cell line, ATCC) was washed twice with DPBS (Dulbecco's phosphate-buffered saline), and the washing solution was discarded. Then, the cells were inoculated with porcine reproductive and respiratory syndrome virus (PRRSV, LMY strain, a kind gift from the Animal and Plant Quarantine Agency, Korea) at 0.1 MOI FFU/mL and incubated (adsorbed) for 1 hour. After virus adsorption, the cells were washed twice again with DPBS and incubated in a preservation medium containing a predetermined concentration of the compound, 1 μg/mL of crystalized trypsin, 1% penicillin, and 1% streptomycin at 36° C. for 36 hours. Then, each plate was frozen and thawed three times to detach cells from each well and Western blotting was performed using a rabbit polyclonal primary antibody against porcine reproductive and respiratory syndrome virus membrane (M) antigen and an HRP-conjugated goat anti-rabbit IgG secondary antibody. In addition, in order to measure the amount of viral antigen reduced by AGM-330d-mCPP and AGM-330t-mCPP, western blotting was performed using an HRP-conjugated goat anti-mouse IgG secondary antibody and a rabbit polyclonal primary antibody against the host protein, GAPDH (glyceraldehyde 3-phosphate dehydrogenase) (FIG. 15A).

An immunofluorescence assay was performed to detect the decrease in the amount of viral antigen in the cytoplasm caused by the inhibition of porcine reproductive and respiratory syndrome virus proliferation by AGM-330d-mCPP and AGM-330t-mCPP. First, each chamber of an 8-well chamber slide containing confluently grown MARC-145 cells was washed twice with DPBS and the washing solution was discarded. Then, the cells were inoculated with porcine reproductive and respiratory syndrome virus (PRRSV, LMY strain, a kind gift from Animal and Plant Quarantine Agency, Korea) at 0.1 MOI FFU/mL, and incubated (adsorbed) for 1 hour. After virus adsorption, the cells were washed twice with DPBS and incubated in a preservation medium containing a predetermined concentration of the compound, 1 μg/mL of crystalized trypsin, 1% penicillin, and 1% streptomycin at 36° C. for 16 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a rabbit polyclonal primary antibody against a porcine reproductive and respiratory syndrome virus membrane (M) antigen was added to each chamber and allowed to stand at 4° C. for 12 hours. Then, each chamber was washed three times with phosphate buffered saline (pH 7.4), the washing solution was discarded, and a dilution of a goat anti-rabbit IgG polyclonal antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and observed with an LSM 800 confocal microscope (FIG. 15B).

Real-time PCR was performed to detect the number of viral genomes reduced by inhibition of porcine reproductive and respiratory syndrome virus proliferation by AGM-330d-mCPP and AGM-330t-mCPP. First, each well of a 12-well plate containing MARC-145 cells grown confluently was washed twice with DPBS (Dulbecco's phosphate-buffered saline) and then the washing solution was discarded. Then, the cells were inoculated with porcine reproductive and respiratory syndrome virus (PRRSV, LMY strain, a kind gift from Animal and Plant Quarantine Agency, Korea) at 0.1 MOI FFU/mL, and incubated (adsorbed) for 1 hour. After virus adsorption, the cells were washed twice with DPBS and incubated in the preservation medium containing a predetermined amount of the compound, 1 μg/mL of crystalized trypsin, 1% penicillin, and 1% streptomycin at 36° C. for 36 hours. Then, each plate was frozen and thawed three times to detach cells from each well and then RNA was extracted using an RNeasy mini kit (Qiagen). CDNA was synthesized from the extracted RNA using a TOPscript™ CDNA synthesis kit (Enzynomics) containing random hexamer and poly(rA)-oligo (dT). Then, the synthesized cDNA, and a forward primer (5'-CACCTCCAGATGCCGTTTG-3', SEQ ID NO: 79) and a reverse primer (5'-ATGCGTGGT-TATCATTTGCC-3', SEQ ID NO: 80) specific for PRRSV M genes were inserted into a TOPreal™ qPCR 2× PreMix (Enzynomics) solution, and real-time PCR was performed in a LineGene 9600 Plus real-time PCR detection system (Bioer, Hangzhou, China) (FIG. 15C).

A cell culture immunofluorescence assay was performed to detect reduced production of PRRSV virus progeny virus by AGM-330d-mCPP and AGM-330t-mCPP. First, each well of a 12-well plate containing confluently grown MARC-145 cells was washed twice with DPBS and the washing solution was discarded. Then, the cells were inoculated with porcine reproductive and respiratory syndrome virus (PRRSV, LMY strain, a kind gift from Animal and Plant Quarantine Agency, Korea) at 0.1 MOI FFU/mL and incubated (adsorbed) for 1 hour. After virus adsorption, the cells were washed twice with DPBS and incubated in a preservation a medium containing predetermined concentration of the compound, 1 μg/mL of crystalized trypsin, 1% penicillin, and 1% streptomycin at 36° C. for 16 hours. Then, each plate was frozen and thawed three times to detach cells from each well, and the supernatant was serially diluted 10×, and then seeded on each well of a 96-well plate containing MARC-145 cells grown confluently. Then, each well was washed twice with phosphate buffered saline (pH 7.4) and the washing solution was discarded. 4% paraformaldehyde fixative was added to each well and immobilization performed at 20° C. for 10 minutes. In order to increase cell permeability, each well was treated with 0.2% Triton-X at 20° C. for 10 minutes. Then, each well was washed twice with phosphate buffered saline (pH 7.4), and the washing solution was discarded. Then, a rabbit polyclonal primary antibody against PRRSV M antigen was added to each well and allowed to react at 4° C. for 8 hours. Each chamber was washed three times with phosphate-buffered saline (pH 7.4), the washing solution was discarded, and a dilution of a goat anti-rabbit IgG polyclonal antibody conjugated with Alexa Fluor 488 was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 15D).

As a result, the amount of viral protein (M), the amount of intracellular viral antigen (M), the number of viral genomes, and the number of viral progeny decreased depending on the concentration of the treated NCL target peptide ligand (FIG. 15). Therefore, it was verified that the NCL-targeting peptide ligand inhibited porcine reproductive and respiratory syndrome virus infection.

Example 10: Confirmation of Porcine Sapovirus (PSaV) Inhibitory Effect of AGM-330 Through In Vitro Experiments Western blot analysis was performed to detect the decrease in viral antigen content by inhibition of porcine sapovirus proliferation by AGM-330d-mCPP and AGM-330t-mCPP. First, each well of a 12-well plate containing confluently grown LLC-PK cells (pig kidney epithelial cell line, ATCC) was washed twice with DPBS (Dulbecco's phosphate-buffered saline), and the washing solution was discarded. Then, the cells were inoculated with porcine sapovirus (PSaV, Cowden strain, a kind gift from Dr. K. O. Chang, Kansas State, USA) at 0.1 MOI FFU/mL and incubated (adsorbed) for 1 hour. After virus adsorption, the cells were washed twice again with DPBS and incubated in a preservation medium containing a predetermined concentration of the compound, 200 μM GCDCA (glycochenodeoxycholic acid), 1% penicillin, and 1% streptomycin at 36° C. for 24 hours. Then, each plate was frozen and thawed three times to detach cells from each well and Western blotting was performed using a rabbit polyclonal primary antibody against PSaV VPg antigen and a HRP-conjugated goat anti-rabbit IgG secondary antibody. In addition, in order to measure the amount of viral antigen reduced by AGM-330d-mCPP and AGM-330t-mCPP, western blotting was performed using an HRP-conjugated goat anti-mouse IgG secondary antibody and a rabbit polyclonal primary antibody against the host protein, GAPDH (glyceraldehyde 3-phosphate dehydrogenase) (FIG. 16A). An immunofluorescence assay was performed to detect the decrease in the amount of viral antigen in the cytoplasm caused by the inhibition of PSaV proliferation by AGM-330d-mCPP and AGM-330t-mCPP. First, each chamber of an 8-well chamber slide containing confluently grown LLC-PK cells was washed twice with DPBS and the washing solution was discarded. Then, the cells were inoculated with porcine sapovirus (PSaV, Cowden strain, a kind gift from Dr. K. O. Chang, Kansas State, USA) at 0.1 MOI FFU/mL, and incubated (adsorbed) for 1 hour. After virus adsorption, the cells were washed twice with DPBS and incubated in a preservation medium containing a predetermined concentration of the compound, 200 μM GCDCA (glycochenodeoxycholic acid), 1% penicillin, and 1% streptomycin at 36° C. for 16 hours. Then, each well was washed twice with DPBS and the washing solution was discarded. 4% paraformaldehyde fixative was added to each chamber and immobilization was performed at 20° C. for 10 minutes. In order to improve cell permeability, each chamber was treated with 0.2% Triton-X at 20° C. for 10 minutes. Then, each well was washed twice with DPBS and the washing solution was discarded. Then, a rabbit polyclonal primary antibody against a PSaV VPg antigen was added to each chamber and allowed to stand at 4° C. for 12 hours. Then, each chamber was washed three times with phosphate buffered saline (pH 7.4), the washing solution was discarded, and a dilution of a goat anti-rabbit IgG secondary antibody conjugated with Alexa Fluor 594 was added to each chamber, followed by incubation at 20° C. for 1 hour. Each chamber was washed three times with phosphate buffered saline (pH 7.4), the washing solution was discarded, and each slide was sealed with a SlowFade Gold antifade solution containing DAPI to stain nuclei and observed with an LSM 800 confocal microscope (FIG. 16B).

Real-time PCR was performed to detect the number of viral genomes reduced by inhibition of PSaV proliferation by AGM-330d-mCPP and AGM-330t-mCPP. First, each well of a 12-well plate containing LLC-PK cells grown confluently was washed twice with DPBS (Dulbecco's phosphate-buffered saline) and then the washing solution was discarded. Then, the cells were inoculated with porcine sapovirus (PSaV, Cowden strain, a kind gift from Dr. K. O. Chang, Kansas State, USA) at 0.1 MOI FFU/mL, and incubated (adsorbed) for 1 hour. After virus adsorption, the cells were washed twice with DPBS and incubated in the preservation medium containing a predetermined amount of the compound, 200 μM GCDCA (glycochenodeoxycholic acid), 1% penicillin, and 1% streptomycin at 36° C. for 24 hours. Then, each plate was frozen and thawed three times to detach cells from each well and then RNA was extracted using an RNeasy mini kit (Qiagen). CDNA was synthesized from the extracted RNA using a TOPscript™ CDNA synthesis kit (Enzynomics) containing random hexamer and poly(rA)-oligo (dT). Then, the synthesized cDNA, and a forward primer (5'-CGAAAGGGAAAAACAAACGC-3', SEQ ID NO: 81) and a reverse primer (5'-TCACTCACTGT-CATAGGTGTCACC-3', SEQ ID NO: 82) specific for PSaV VPg were inserted into a TOPreal™ qPCR 2× PreMix (Enzynomics) solution, and real-time PCR was performed in a LineGene 9600 Plus real-time PCR detection system (Bioer, Hangzhou, China) (FIG. 16C).

A cell culture immunofluorescence assay was performed to detect reduced production of PsaV progeny virus by AGM-330d-mCPP and AGM-330t-mCPP. First, each well of a 12-well plate containing confluently grown LLC-PK cells was washed twice with DPBS and the washing solution was discarded. Then, the cells were inoculated with porcine sapovirus (PSaV, Cowden strain, a kind gift from Dr. K. O. Chang, Kansas State, USA) at 0.1 MOI FFU/mL and incubated (adsorbed) for 1 hour. After virus adsorption, the cells were washed twice with DPBS and incubated in a preservation medium containing a predetermined concentration of the compound, 200 μM GCDCA (glycochenodeoxycholic acid), 1% penicillin, and 1% streptomycin at 36° C. for 16 hours. Then, each plate was frozen and thawed three times to detach cells from each well, and the supernatant was serially diluted 10×, and then seeded on each well of a 96-well plate containing LLC-PK cells grown confluently. Then, each well was washed twice with phosphate buffered saline (pH 7.4) and the washing solution was discarded. 4% paraformaldehyde fixative was added to each well and immobilization was performed at 20° C. for 10 minutes. In order to increase cell permeability, each well was treated with 0.2% Triton-X at 20° C. for 10 minutes. Then, each well was washed twice with phosphate buffered saline (pH 7.4), and the washing solution was discarded. Then, a rabbit polyclonal primary antibody against a PSaV VPg antigen was added to each well and allowed to react at 4° C. for 8 hours. Each chamber was washed three times with phosphate-buffered saline (pH 7.4), the washing solution was discarded, and a dilution of a goat anti-rabbit IgG polyclonal antibody conjugated with Alexa Fluor 488 was added to each well, followed by incubation at 20° C. for 1 hour. Each well was washed three times with phosphate buffered saline (pH 7.8), the washing solution was discarded, the nuclei were stained with propidium iodide and sealed with glycerol, and the number of positive cells was counted with an inverted fluorescence microscope (FIG. 16D).

As a result, the amount of viral protein (VPg), the amount of intracellular viral antigen (VPg), the number of viral genomes, and the number of viral progeny decreased depending on the concentration of the treated NCL target peptide ligand (FIG. 16). Therefore, it was verified that the NCL-targeting peptide ligand inhibited porcine sapovirus infection.

Example 11: Confirmation of $CC_{50}$ of AGM-330, $IC_{50}$ of AGM-330 for IAV, BCoV, PEDV, RVA, PRRSV, and PSaV, and Selective Index Through In Vitro Experiments In order to determine the half maximal cytotoxic concentration ($CC_{50}$) of AGM-330, confluent A549, MDCK, Vero E6, MA104, MARC-145, and LLC-PK cells grown in 96-well plates were treated with dilutions of NCL-targeting peptide ligands (AGM-330d-mCPP, AGM-330t-mCPP) prepared from a low concentration to 10 μM, followed by incubation for 24 hours. After removing each culture medium, 200 μL of a 3-(4,5-dimethylthiazol-2-yl)-2,5-diphenyl tetrazolium bromide (MTT) solution was added thereto, followed by incubation in a 5% $CO_2$ incubator at 36° C. for 4 hours. Then, 150 μL of a DMSO solution was added to each well and then incubated at 20° C. Then, the optical density (OD) was measured at a wavelength of 570 nm with an enzyme-linked immunosorbent assay (ELISA) reader (Table 6).

TABLE 6

Half maximal cytotoxic concentration ($CC_{50}$) of AGM-380d-mCPP and AGM-380t-mCPP determined by cellular NAD(P)H-dependent cellular oxidoreductase assay (MTT assay) in different cell lines.

| | $CC_{50}$ (μM) | |
|---|---|---|
| Cell lines | AGM-330d-mCPP | AGM-330t-mCPP |
| A549 | 102.00 | 92.50 |
| HRT-18 | 89.53 | 91.93 |
| Vero E6 | 107.50 | 99.92 |
| MA-104 | 99.93 | 89.95 |
| MARC-145 | 97.97 | 88.68 |
| LLC-PK | 101.30 | 92.70 |

In order to determine the half maximal inhibitory concentration ($IC_{50}$) of AGM-330 for each virus, the supernatant of confluent A549, MDCK, Vero E6, MA104, MARC-145 and LLC-PK cells grown in 12-well plates was removed, the remaining cells were inoculated at an MOI of 0.1 with influenza A virus (IAV, PR8 strain), bovine coronavirus (BCoV, KWD20 strain), porcine epidemic diarrhea virus (PEDV, QIAP1401 strain), bovine rotavirus (RVA, NCDV strain), porcine reproductive and respiratory syndrome virus (PRRSV, LMY strain), and porcine sapovirus (PSaV, Cowden strain), and then the virus was adsorbed to the cells for 1 hour. Then, 2 ml of a culture medium containing serial (stepwise) dilutions of the NCL-targeting peptide ligands (AGM-330d-mCPP, AGM-330t-mCPP) from low concentration to a concentration of 10 μM was added to the cells, the cells infected with influenza A virus and bovine rotavirus were incubated for 24 hours, the cells infected with bovine coronavirus, porcine epidemic diarrhea virus, and porcine sapovirus were incubated for 36 hours, and the cells infected with porcine reproductive and respiratory syndrome virus were incubated for 48 hours. After the completion of the incubation, each plate was frozen and thawed three times, and then the supernatant was serially diluted 10×. To test the titer of the virus, the supernatant of confluent A549, MDCK, Vero E6, MA104, MARC-145 and LLC-PK cells grown on 96-well plates was removed, and each well was washed three times with phosphate buffered saline. Each well of the 96-well plate on which A549, MDCK, Vero E6, MA104, MARC-145, and LLC-PK cells were confluently grown was inoculated with 100 µL of each 10-fold serially diluted viral solution left after removal of the supernatant and incubated in a 5% $CO_2$ incubator at 36° C. for 18 hours. After removing the supernatant, the cells were immobilized with a 4% paraformaldehyde solution for 15 minutes and each well was washed three times with phosphate buffered saline, and then treated with 0.2% Triton X-100 at 20° C. for 10 minutes. Each well was washed three times with phosphate buffered saline and 100 to 200× dilutions of primary antibodies against the NP antigen of influenza A virus, the S antigen of bovine coronavirus, the N antigen of porcine epidemic diarrhea virus, the VP6 antigen of species rotavirus, the M antigen of porcine reproductive and respiratory syndrome virus, and the VPg antigen of porcine sapovirus were seeded on each well and allowed to react in a refrigerator at 4° C. for 12 hours. After removing the supernatant, each well was washed three times with phosphate buffered saline and a 100 to 200× diluted Alexa Fluor 488 or fluorescein isothiocyanate-conjugated secondary antibody was seeded into each well for 2 hours and then allowed to react at room temperature for 2 hours. After removing the supernatant, the nuclei were stained with a propidium iodide solution, a 60% glycerol solution was added to each well, and each virus-positive cell was observed with a fluorescence microscope. Based on the experiments, $CC_{50}$ and $IC_{50}$ were calculated and then selective index (SI) was calculated by dividing the $CC_{50}$ by the $IC_{50}$ ($CC_{50}/IC_{50}$) (Table 7).

TABLE 7

| Half maximal inhibitory concentration ($IC_{50}$) and selectivity index (SI) of AGM-380d-mCPP and AGM-380t-mCPP against 6 RNA viruses | | | |
| --- | --- | --- | --- |
| | AGM-330d-mCPP (µM) | | AGM-330t-mCPP (µM) | |
| Viruses | $IC_{50}$ | SI | $IC_{50}$ | SI |
| IAV | 1.40 | 72.90 | 1.10 | 84.1 |
| BCoV | 1.27 | 70.49 | 1.31 | 70.17 |
| PEDV | 2.82 | 38.12 | 1.89 | 52.86 |
| RVA | 1.88 | 53.15 | 1.32 | 68.14 |
| PRRSV | 2.26 | 43.26 | 2.80 | 31.67 |
| PSaV | 9.80 | 10.30 | 5.20 | 17.80 |

The result showed that the NCL-targeting peptide ligands (AGM-330d-mCPP, AGM-330t-mCPP) did not exhibit significant cytotoxicity even at a high concentration of 10 µM, and inhibited infection with influenza A virus, bovine coronavirus, porcine epidemic diarrhea virus, bovine rotavirus, porcine reproductive and respiratory syndrome virus, and porcine sapovirus even at low concentrations (FIG. 17).

Example 12: Confirmation of SARS-COV-2 Inhibitory Effect of AGM-330 Through In Vitro Experiments In order to determine the half maximal cytotoxic concentration ($CC_{50}$) of AGM-330, confluent Vero cell line (African green monkey kidney cell line, ATCC) cells grown in 96-well plates were treated with dilutions of NCL-targeting peptide ligands (AGM-330d-mCPP, AGM-330t-mCPP) prepared from a low concentration to 20 µM, followed by incubation for 24 hours. After removing each culture medium, 200 µL of a 3-(4,5-dimethylthiazol-2-yl)-2,5-diphenyl tetrazolium bromide (MTT) solution was added thereto, followed by incubation in a 5% $CO_2$ incubator at 36° C. for 4 hours. Then, 150 µL of a DMSO solution was added to each well and then incubated at 20° C. Then, the optical density (OD) was measured at a wavelength of 570 nm with an enzyme-linked immunosorbent assay (ELISA) reader.

In order to determine the half maximal inhibitory concentration ($IC_{50}$) of AGM-330 for SARS-COV-2, the confluent Vero E6 cells grown in 384-well microplates were inoculated at an MOI of 0.125 with SARS-COV-2 and then the virus was adsorbed on the cells for 1 hour. Then, the cells were treated with the culture solution containing serial (stepwise) dilutions of the NCL-targeting peptide ligands (AGM-330d-mCPP, AGM-330t-mCPP) and chloroquine, remdesivir or lopinavir as a positive control from a low concentration to a concentration of 20 µM 1 hour before and 1 hour after virus inoculation. After treatment with the NCL target peptide ligand and positive control, the cells were incubated for 24 hours. After the completion of incubation, each plate was washed three times with phosphate buffered saline. Then, the primary antibody against SARS-COV-2 nucleocapsid (N) was seeded on each well and then incubated in a refrigerator at 4° C. for 12 hours. After removing the supernatant, each well was washed three times with phosphate buffered saline, and an Alexa Fluor 488-conjugated secondary antibody was seeded on each well, followed by incubation at room temperature for 2 hours. After removing the supernatant, the nucleus was stained with Hoechst 33342, and the fluorescence image of the infected cells was detected with Operetta, a large-capacity image analysis device. Based on the experiments, $CC_{50}$ and $IC_{50}$ were calculated and then selective index (SI) was calculated by dividing the $CC_{50}$ by the $IC_{50}$ ($CC_{50}/IC_{50}$).

TABLE 8

| Type | $IC_{50}$ (µM) | $CC_{50}$ (µM) |
| --- | --- | --- |
| Chloroquine | 8.25 | >150 |
| Remdesivir | 10.87 | >50 |
| Lopinavir | 15.45 | >50 |
| AGM-330t-mCPP | 7.22 | >20 |
| AGM-330d-mCPP | 12.46 | >20 |
| AGM-330d-dCPP | 5.2 | 7.73 |

The result showed that the NCL-targeting peptide ligands exhibited increased $IC_{50}$ compared to conventional drugs used as positive control and exhibited no significant cytotoxicity even at a high concentration of 20 µM (FIG. 18).

The result showed that the NCL-targeting peptide ligands inhibited SAR-COV-2 infection.

Example 13: Evaluation of Antiviral Efficacy of AGM-330 Using Hamster Corona 19-Infected Model Syrian hamsters (Female, 11 weeks, Raon Bio Co., Ltd.) were infected with SARS-COV-2 ($2 \times 10^5$ pfu/mL) through intranasal irrigation.

The NCL-targeting peptide ligand, AGM-330d-mCPP (AGM-380D) (0.2, 2, 6 mg/kg) was intraperitoneally administered to the infected hamster animal model eight times for four days at 12-hour intervals. Mortality and general symptoms were observed for 5 days after infection. The result showed that no dead animals occurred during the test period and no clinical abnormalities related to the test substance were observed. Body weight was measured on the day of infection, the second day after infection, and the fourth day after infection. The result showed that body weight decreased in the test group and the virus control group (VC) excluding the normal control group (NC). No significant weight change was observed between the virus control group and the test group (FIG. 19).

Autopsy was measured on the fourth day after infection. The result showed that macroscopic changes including congestion/bleeding and edema due to viral infection were detected in the lungs of the test group and the virus control group excluding the normal control group. Macroscopic changes were significantly alleviated in the group administered with AGM-330d-mCPP (6 mg/kg), compared to the virus control group (FIGS. 20 to 25).

Upon the histopathological observation of the lungs, findings such as infiltration of inflammatory cells in the alveolar cavity and interstitial tissue due to viral infection, hemorrhage, and hyaline membrane formation were observed (Table 9). Histopathological lesions were significantly reduced in the group administered with AGM-330d-mCPP (6 mg/kg) compared to the virus control group (FIG. 26).

TABLE 9

Incidence and severity of lung histopathological findings
(AGM-1: AGM-380D 0.2 mg/kg, AGM-2: AGM-380D 2 mg/kg,
AGM-3: AGM-380D 6 mg/kg)

| Organ | Group | | Findings | | | | |
|---|---|---|---|---|---|---|---|
| | | | NC | VC | AGM-1 | AGM-2 | AGM-3 |
| | Dose (mg/kg) | | 0 | 0 | 0.2 | 2 | 6 |
| | No of Animals | | 5 | 5 | 5 | 5 | 5 |
| Lung | Neutrophilic/ | Normal | 5 | 0 | 0 | 0 | 0 |
| | lymphocytic | Minimal | 0 | 1 | 2 | 2 | 5 |
| | cell, | Mild | 0 | 3 | 3 | 3 | 0 |
| | alveolar | Moderate | 0 | 1 | 0 | 0 | 0 |
| | Inflammatory | Normal | 5 | 0 | 0 | 0 | 0 |
| | cell, | Minimal | 0 | 1 | 0 | 0 | 2 |
| | intestinal | Mild | 0 | 0 | 2 | 1 | 3 |
| | | Moderate | 0 | 3 | 3 | 3 | 0 |
| | | Severe | 0 | 1 | 0 | 1 | 0 |
| | Hyaline | Normal | 5 | 0 | 0 | 0 | 0 |
| | membrane | Minimal | 0 | 1 | 0 | 0 | 4 |
| | | Mild | 0 | 0 | 3 | 3 | 1 |
| | | Moderate | 0 | 4 | 2 | 2 | 0 |
| | | Severe | 0 | 0 | 0 | 0 | 0 |
| | Hemorrhage | Normal | 5 | 1 | 0 | 0 | 0 |
| | | Minimal | 0 | 1 | 3 | 2 | 5 |
| | | Mild | 0 | 3 | 2 | 3 | 0 |
| | | Moderate | 0 | 0 | 0 | 0 | 0 |
| | | Severe | 0 | 0 | 0 | 0 | 0 |
| | Proteinaceous | Normal | 5 | 0 | 0 | 0 | 0 |
| | debris | Minimal | 0 | 1 | 3 | 3 | 4 |
| | | Mild | 0 | 4 | 2 | 2 | 1 |
| | | Moderate | 0 | 0 | 0 | 0 | 0 |
| | | Severe | 0 | 0 | 0 | 0 | 0 |
| | Alveolar wall | Normal | 4 | 0 | 0 | 0 | 0 |
| | thickening | Minimal | 0 | 1 | 0 | 0 | 2 |
| | | Mild | 0 | 2 | 3 | 3 | 3 |
| | | Moderate | 1 | 2 | 2 | 2 | 0 |
| | | Severe | 0 | 0 | 0 | 0 | 0 |

Example 14: Confirmation of In Vivo Antiviral Effect of AGM-330 Against Influenza a Virus C57BL/6 mice were infected with influenza A virus by intranasal administration ($1\times10^4$ pfu/ml, 50 µl), the NCL-targeting peptide ligand was intraperitoneally administered thereto once a day for 5 days at each concentration, and the survival rate for 16 days was observed. AGM-330d-mCPP had a significantly improved survival rate at the dose concentrations of 0.04, 0.2, and 1.00 mg/kg (FIG. 27A), and AGM-330t-mCPP had a significantly improved survival rate at dose concentrations of 0.334 and 1.67 mg/kg (FIG. 27B).

Example 15: Confirmation of In Vivo Antiviral Effect of Combined Administration of AGM-330 and Oseltamivir Against Influenza a Virus After intranasal infection of C57BL/6 mice with influenza A virus ($1\times10^4$ pfu/ml, 50 µl), the NCL-targeting peptide ligand, AGM-380d-mCPP 1.00 mg/kg, the NCL-targeting peptide ligand, AGM-330t-mCPP 1.67 mg/kg, a combination of the AGM-330d-mCPP 1.00 mg/kg and oseltamivir 2 mg/kg, and a combination of AGM-330t-mCPP 1.67 mg/kg and oseltamivir 2 mg/kg were administered daily for 5 days. AGM-330d-mCPP and AGM-330t-mCPP were intraperitoneally administered and oseltamivir was orally administered. The survival rate was observed for 16 days after virus inoculation. Compared to AGM-330d-mCPP alone and AGM-330t-mCPP alone, the combination of AGM-330d-mCPP and oseltamivir exhibited a survival rate of 100% (FIG. 28A), and the combination of AGM-330t-mCPP and oseltamivir exhibited a survival rate of 90% (FIG. 28B), which indicates that the combined administration with oseltamivir had a clear therapeutic effect on influenza A virus infection.

Example 16: Confirmation of In Vivo Inhibitory Effect of AGM-330 on Influenza a Virus Replication The levels of PB1 mRNA and protein expression and viral titer were measured in the lung tissues of mice of the NCL-targeting peptide ligand test group at days post infection (DPI) of 4 and 6 in Example 14.

The result showed that the mRNA and protein expression levels of PB1 were significantly reduced at the DPI of 4 and 6, respectively. In addition, the result of detection of the virus titer showed that the influenza A virus infection was inhibited by the NCL-targeting peptide and the number of viruses was remarkably reduced. This result means that the number of viruses decreased due to the NCL-targeting peptide ligand and this result is related to the survival rate of Example 14 (FIG. 29).

INDUSTRIAL APPLICABILITY

The present invention demonstrated that the AGM peptide ligands and mutants thereof screened using the MAP synthesis and OBOC combination inhibited the proliferation and replication of viruses (in vitro and in vivo). Therefore, NCL-targeting AGM is useful for antiviral activity.

Although specific configurations of the present invention have been described in detail, those skilled in the art will appreciate that this description is provided to set forth preferred embodiments for illustrative purposes, and should not be construed as limiting the scope of the present invention. Therefore, the substantial scope of the present invention is defined by the accompanying claims and equivalents thereto.

SEQUENCE LISTING FREE TEXT

An electronic file is attached.

The invention claimed is:

1. An antiviral composition comprising an AGM peptide that specifically binds to nucleolin (NCL),
   wherein the AGM peptide consists of an amino acid sequence selected from the group consisting of: the amino acid sequence of any one of SEQ ID NO: 1, SEQ ID NO: 9 to SEQ ID NO: 15 and SEQ ID NO: 20.

2. The antiviral composition according to claim 1, wherein the amino acid sequence is selected from the group consisting of the amino acid sequence of any one of SEQ ID NO: 9 to SEQ ID NO: 15 and SEQ ID NO: 20.

3. The antiviral composition according to claim 1, wherein the antiviral composition comprises an AGM peptide-PEG conjugate conjugated with a polyethylene glycol (PEG) chain.

4. The antiviral composition according to claim 3, wherein the polyethylene glycol chain comprises 2 to 24 ethylene glycol groups.

5. The antiviral composition according to claim 3, wherein the polyethylene glycol chain is linked to the AGM peptide through a linker.

6. The antiviral composition according to claim 3, wherein the composition comprises a multimer comprising two or more AGM peptide-PEG conjugates comprising the AGM peptide-PEG conjugate.

7. The antiviral composition according to claim 6, wherein the multimer comprises 2 to 8 AGM peptide-PEG conjugates.

8. The antiviral composition according to claim 7, wherein the 2 to 8 AGM peptide-PEG conjugates are linked to each other via a linker.

9. The antiviral composition according to claim 1, wherein the composition has antiviral activity against at least one selected from the group consisting of coronavirus, influenza virus, porcine epidemic diarrhea virus, bovine rotavirus, porcine sapovirus, porcine reproductive and respiratory syndrome virus, Alfuy virus, Banzi virus, Chikungunya virus, Dengue virus, hepatitis B virus (HBV), hepatitis C virus (HCV), human cytomegalovirus, human immunodeficiency virus (HIV), Japanese encephalitis virus, Kokobera virus, Kunjin virus, Kyasanur forest disease virus, louping ill virus, measles virus, metapneumovirus, mosaic virus, Murray Valley virus, parainfluenza virus, polio virus, Powassan virus, respiratory syncytial virus (RSV), Rocio virus, Saint Louis encephalitis virus, tick-borne encephalitis virus, West Nile virus and Yellow fever virus.

10. An antiviral composition comprising an AGM peptide-CPP fusion peptide in which an AGM peptide that specifically binds to nucleolin (NCL) is fused with a cell-penetrating peptide (CPP), wherein the AGM peptide consists of comprises an amino acid sequence selected from the group consisting of: the amino acid sequence of any one of SEQ ID NO: 1, SEQ ID NO: 9 to SEQ ID NO: 15 and SEQ ID NO: 20.

11. The antiviral composition according to claim 10, wherein the amino acid sequence is selected from the group consisting of the amino acid sequence of any one of SEQ ID NO: 9 to SEQ ID NO: 15 and SEQ ID NO: 20.

12. The antiviral composition according to claim 10, wherein the antiviral composition comprises an AGM peptide-PEG conjugate conjugated with a polyethylene glycol (PEG) chain.

13. The antiviral composition according to claim 12, wherein the composition comprises a multimer comprising two or more AGM peptide-PEG conjugates comprising the AGM peptide-PEG conjugate.

14. The antiviral composition according to claim 10, wherein the cell-penetrating peptide is selected from the group consisting of amino acid sequences of SEQ ID NO: 21 to SEQ ID NO: 70.

15. The antiviral composition according to claim 10, wherein the composition has antiviral activity against at least one selected from the group consisting of coronavirus, influenza virus, porcine epidemic diarrhea virus, bovine rotavirus, porcine sapovirus, porcine reproductive and respiratory syndrome virus, Alfuy virus, Banzi virus, Chikungunya virus, Dengue virus, hepatitis B virus (HBV), hepatitis C virus (HCV), human cytomegalovirus, human immunodeficiency virus (HIV), Japanese encephalitis virus, Kokobera virus, Kunjin virus, Kyasanur forest disease virus, louping ill virus, measles virus, metapneumovirus, mosaic virus, Murray Valley virus, parainfluenza virus, polio virus, Powassan virus, respiratory syncytial virus (RSV), Rocio virus, Saint Louis encephalitis virus, tick-borne encephalitis virus, West Nile virus and Yellow fever virus.

16. A composition for preventing or treating viral infections comprising the antiviral composition according to claim 1.

17. A health functional food composition for preventing or ameliorating viral infections comprising the antiviral composition according to claim 1.

18. A composition for preventing or treating viral infections comprising the antiviral composition according to claim 10.

19. A health functional food composition for preventing or ameliorating viral infections comprising the antiviral composition according to claim 10.

* * * * *

```
                          SEQUENCE LISTING

<160> NUMBER OF SEQ ID NOS: 84

<210> SEQ ID NO 1
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 1

Arg His Gly Ala Met Val Tyr Leu Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic construct AGM-331

<400> SEQUENCE: 2

Ala Asp His Arg His Arg Arg Ser Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct AGM-332

<400> SEQUENCE: 3

Ala Val Ala Arg Ala Arg Arg Arg Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct AGM-333

<400> SEQUENCE: 4

Arg Phe Leu Lys Asn Lys Lys Ala Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic construct AGM-334

<400> SEQUENCE: 5

Arg Trp Leu Lys Asn Lys Lys Ala Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic construct AGM-335
```

```
<400> SEQUENCE: 6

Phe Gly Arg Leu Lys Lys Pro Leu Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct AGM-336

<400> SEQUENCE: 7

Lys Arg Arg Arg Arg Glu Arg Ala Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct AGM-337

<400> SEQUENCE: 8

Lys Arg Arg Arg Lys Ala Pro Thr Asp
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 9

Lys His Gly Ala Met Val Tyr Leu Lys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 10

Arg Arg Gly Ala Met Val Tyr Leu Lys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 11

Arg His Gly Leu Met Val Tyr Leu Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic construct AGM-330
```

```
<400> SEQUENCE: 12

Arg His Gly Ala Leu Val Tyr Leu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct AGM-330
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Arg His Gly Ala Xaa Val Tyr Leu Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 14

Arg His Gly Ala Met Ala Tyr Leu Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 15

Arg His Gly Ala Met Val Phe Leu Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic construct AGM-330

<400> SEQUENCE: 16

Gly Ala Met Val Tyr Leu Lys
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic construct AGM 330

<400> SEQUENCE: 17

Arg His Arg His Gly Ala Met Val Tyr Leu Lys
1               5                   10

<210> SEQ ID NO 18
<211> LENGTH: 13
<212> TYPE: PRT
<213> ORGANISM: Artificial Sequence
```

```
<220> FEATURE:
<223> OTHER INFORMATION: Synthetic construct AGM-330

<400> SEQUENCE: 18

Arg His Arg His Arg His Gly Ala Met Val Tyr Leu Lys
1               5               10

<210> SEQ ID NO 19
<211> LENGTH: 9
<212> TYPE: PRT
<213> ORGANISM: Artificial Sequence
<220> FEATURE:
<223> OTHER INFORMATION: Synthetic construct AGM-330

<400> SEQUENCE: 19

Lys Leu Tyr Val Met Ala Gly His Arg
1               5

<210> SEQ ID NO 20
<211> LENGTH: 13
<212> TYPE: PRT
<213> ORGANISM: Artificial Sequence
<220> FEATURE:
<223> OTHER INFORMATION: Synthetic construct AGM-330

<400> SEQUENCE: 20

Arg His Gly Ala Met Val Tyr Leu Lys Leu Lys Leu Lys
1               5               10

<210> SEQ ID NO 21
<211> LENGTH: 11
<212> TYPE: PRT
<213> ORGANISM: Artificial Sequence
<220> FEATURE:
<223> OTHER INFORMATION: Synthetic construct TAT

<400> SEQUENCE: 21

Tyr Gly Arg Lys Lys Arg Arg Gln Arg Arg Arg
1               5               10

<210> SEQ ID NO 22
<211> LENGTH: 13
<212> TYPE: PRT
<213> ORGANISM: Artificial Sequence
<220> FEATURE:
<223> OTHER INFORMATION: Synthetic construct TAT (48-60)

<400> SEQUENCE: 22

Gly Arg Lys Lys Arg Arg Gln Arg Arg Arg Pro Pro Gln
1               5               10

<210> SEQ ID NO 23
<211> LENGTH: 9
<212> TYPE: PRT
<213> ORGANISM: Artificial Sequence
<220> FEATURE:
<223> OTHER INFORMATION: Synthetic construct TAT (49-57)

<400> SEQUENCE: 23

Arg Lys Lys Arg Arg Gln Arg Arg Arg
1               5

<210> SEQ ID NO 24
<211> LENGTH: 16
<212> TYPE: PRT
<213> ORGANISM: Artificial Sequence
<220> FEATURE:
```

<223> OTHER INFORMATION: Synthetic construct Penetratin

<400> SEQUENCE: 24

Arg Gln Ile Lys Ile Trp Phe Gln Asn Arg Arg Met Lys Trp Lys Lys
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Synthetic construct R8

<400> SEQUENCE: 25

Arg Arg Arg Arg Arg Arg Arg Arg
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic construct R9-TAT

<400> SEQUENCE: 26

Gly Arg Arg Arg Arg Arg Arg Arg Arg Arg Pro Pro Gln
1               5                   10

<210> SEQ ID NO 27
<211> LENGTH: 21
<212> TYPE: PRT
<213> ORGANISM: Artificial Sequence
<220> FEATURE:
<223> OTHER INFORMATION: Synthetic construct Pep-1

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 11
<212> TYPE: PRT
<213> ORGANISM: Artificial Sequence
<220> FEATURE:
<223> OTHER INFORMATION: Synthetic construct Hph-1

<400> SEQUENCE: 28

Tyr Ala Arg Val Arg Arg Arg Gly Pro Arg Arg
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Synthetic construct MAP

<400> SEQUENCE: 29

Lys Leu Ala Leu Lys Leu Ala Leu Lys Ala Leu Lys Ala Ala Leu Lys
1               5                   10                  15

Leu Ala

<210> SEQ ID NO 30

```
<211> LENGTH: 18
<212> TYPE: PRT
<213> ORGANISM: Artificial Sequence
<220> FEATURE:
<223> OTHER INFORMATION: Synthetic construct pVEC

<400> SEQUENCE: 30

Leu Leu Ile Ile Leu Arg Arg Arg Ile Arg Lys Gln Ala His Ala His
1               5                   10                  15

Ser Lys

<210> SEQ ID NO 31
<211> LENGTH: 20
<212> TYPE: PRT
<213> ORGANISM: Artificial Sequence
<220> FEATURE:
<223> OTHER INFORMATION: Synthetic construct DS4

<400> SEQUENCE: 31

Val Gln Ile Phe Arg Ile Met Arg Ile Leu Arg Ile Leu Lys Leu Ala
1               5                   10                  15

Arg His Ser Thr
            20

<210> SEQ ID NO 32
<211> LENGTH: 27
<212> TYPE: PRT
<213> ORGANISM: Artificial Sequence
<220> FEATURE:
<223> OTHER INFORMATION: Synthetic construct Transportan

<400> SEQUENCE: 32

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 33
<211> LENGTH: 20
<212> TYPE: PRT
<213> ORGANISM: Artificial Sequence
<220> FEATURE:
<223> OTHER INFORMATION: Synthetic construct gH625

<400> SEQUENCE: 33

His Gly Leu Ala Ser Thr Leu Thr Arg Trp Ala His Tyr Asn Ala Leu
1               5                   10                  15

Ile Arg Ala Phe
            20

<210> SEQ ID NO 34
<211> LENGTH: 17
<212> TYPE: PRT
<213> ORGANISM: Artificial Sequence
<220> FEATURE:
<223> OTHER INFORMATION: Synthetic construct VP22

<400> SEQUENCE: 34

Asn Ala Lys Thr Arg Arg His Glu Arg Arg Arg Lys Leu Ala Ile Glu
1               5                   10                  15

Arg

<210> SEQ ID NO 35
<211> LENGTH: 20
```

```
<212> TYPE: PRT
<213> ORGANISM: Artificial Sequence
<220> FEATURE:
<223> OTHER INFORMATION: Synthetic construct DS4

<400> SEQUENCE: 35

Val Gln Ile Phe Arg Ile Met Arg Ile Leu Arg Ile Leu Lys Leu Ala
1               5                   10                  15

Arg His Ser Thr
            20

<210> SEQ ID NO 36
<211> LENGTH: 16
<212> TYPE: PRT
<213> ORGANISM: Artificial Sequence
<220> FEATURE:
<223> OTHER INFORMATION: Synthetic construct DS4-1

<400> SEQUENCE: 36

Arg Ile Met Arg Ile Leu Arg Ile Leu Lys Leu Ala Arg His Ser Thr
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: Synthetic construct DS4-2

<400> SEQUENCE: 37

Val Gln Ile Phe Arg Ile Met Arg Ile Leu Arg Ile Leu Lys Leu Ala
1               5                   10                  15

Arg

<210> SEQ ID NO 38
<211> LENGTH: 13
<212> TYPE: PRT
<213> ORGANISM: Artificial Sequence
<220> FEATURE:
<223> OTHER INFORMATION: Synthetic construct DS4-3

<400> SEQUENCE: 38

Arg Ile Met Arg Ile Leu Arg Ile Leu Lys Leu Ala Arg
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic construct KS4

<400> SEQUENCE: 39

Phe Arg Leu Val Arg Leu Leu Arg Phe Leu Arg Ile Leu Leu Ile Ile
1               5                   10                  15

Ser

<210> SEQ ID NO 40
<211> LENGTH: 14
<212> TYPE: PRT
<213> ORGANISM: Artificial Sequence
<220> FEATURE:
<223> OTHER INFORMATION: Synthetic construct KS4-1

<400> SEQUENCE: 40
```

```
Phe Arg Leu Val Arg Leu Leu Arg Phe Leu Arg Ile Leu Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic construct KS4-2

<400> SEQUENCE: 41

Arg Leu Val Arg Leu Leu Arg Phe Leu Arg
1               5                   10

<210> SEQ ID NO 42

<400> SEQUENCE: 42

000

<210> SEQ ID NO 43
<211> LENGTH: 9
<212> TYPE: PRT
<213> ORGANISM: Artificial Sequence
<220> FEATURE:
<223> OTHER INFORMATION: Synthetic construct N5

<400> SEQUENCE: 43

Arg Ile Leu Arg Ile Leu Arg Ile Leu
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic construct N5

<400> SEQUENCE: 44

Arg Ile Leu Arg Ile Leu Arg Ile Leu Arg Ile Leu Arg Ile Leu
1               5                   10                  15

<210> SEQ ID NO 45
<211> LENGTH: 21
<212> TYPE: PRT
<213> ORGANISM: Artificial Sequence
<220> FEATURE:
<223> OTHER INFORMATION: Synthetic construct N7

<400> SEQUENCE: 45

Arg Ile Leu Arg Ile Leu Arg Ile Leu Arg Ile Leu Arg Ile Leu Arg
1               5                   10                  15

Ile Leu Arg Ile Leu
            20

<210> SEQ ID NO 46
<211> LENGTH: 13
<212> TYPE: PRT
<213> ORGANISM: Artificial Sequence
<220> FEATURE:
<223> OTHER INFORMATION: Synthetic construct K3

<400> SEQUENCE: 46

Arg Ile Phe Trp Val Ile Lys Leu Ala Arg His Phe Ile
1               5                   10
```

-continued

```
<210> SEQ ID NO 47
<211> LENGTH: 16
<212> TYPE: PRT
<213> ORGANISM: Artificial Sequence
<220> FEATURE:
<223> OTHER INFORMATION: Synthetic construct C3

<400> SEQUENCE: 47

Lys Ser Leu Arg Val Leu Arg Val Leu Arg Pro Leu Lys Thr Ile Lys
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic construct C4

<400> SEQUENCE: 48

Arg Leu Phe Arg Val Met Arg Leu Val Lys Leu Leu Ser Arg Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic construct S2

<400> SEQUENCE: 49

Arg Ser Phe Arg Leu Leu Arg Val Phe Lys Leu Ala Lys Ser Trp
1               5                   10                  15

<210> SEQ ID NO 50
<211> LENGTH: 22
<212> TYPE: PRT
<213> ORGANISM: Artificial Sequence
<220> FEATURE:
<223> OTHER INFORMATION: Synthetic construct S4

<400> SEQUENCE: 50

Arg Val Ile Arg Leu Ala Arg Ile Gly Arg Ile Leu Arg Leu Val Lys
1               5                   10                  15

Gly Ala Lys Gly Ile Arg
            20

<210> SEQ ID NO 51
<211> LENGTH: 13
<212> TYPE: PRT
<213> ORGANISM: Artificial Sequence
<220> FEATURE:
<223> OTHER INFORMATION: Synthetic construct D1

<400> SEQUENCE: 51

Arg Ala Gly Arg Ile Leu Arg Ile Leu Lys Leu Ala Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic construct D2

<400> SEQUENCE: 52

Arg Ile Met Arg Gly Leu Arg Ile Leu Lys Leu Ala Arg
1               5                   10
```

-continued

```
<210> SEQ ID NO 53
<211> LENGTH: 13
<212> TYPE: PRT
<213> ORGANISM: Artificial Sequence
<220> FEATURE:
<223> OTHER INFORMATION: Synthetic construct D3

<400> SEQUENCE: 53

Arg Ile Met Arg Ile Leu Arg Leu Met Lys Leu Ala Arg
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic construct D4

<400> SEQUENCE: 54

Arg Ile Met Arg Ile Leu Arg Ile Leu Lys Met Phe Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic construct D5

<400> SEQUENCE: 55

Arg Ile Met Arg Ile Leu Arg Ala Leu Lys Leu Ala Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetic construct D6

<400> SEQUENCE: 56

Arg Ile Met Arg Gly Met Arg Ile Leu Lys Leu Ala Arg
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetic construct D7

<400> SEQUENCE: 57

Arg Leu Phe Arg Ile Leu Arg Ile Leu Lys Leu Ala Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic construct D8

<400> SEQUENCE: 58

Arg Ile Met Arg Met Val Arg Ile Leu Lys Leu Ala Arg
1               5                   10
```

```
<210> SEQ ID NO 59
<211> LENGTH: 13
<212> TYPE: PRT
<213> ORGANISM: Artificial Sequence
<220> FEATURE:
<223> OTHER INFORMATION: Synthetic construct D9

<400> SEQUENCE: 59

Arg Ile Met Arg Ile Leu Arg Leu Val Lys Leu Ala Arg
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic construct D10

<400> SEQUENCE: 60

Arg Ile Met Arg Ile Leu Arg Ile Leu Lys Gly Val Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic construct D11

<400> SEQUENCE: 61

Arg Asn Leu Arg Ile Leu Arg Ile Leu Lys Leu Ala Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic construct D12

<400> SEQUENCE: 62

Arg Ile Met Arg Asp Ile Arg Ile Leu Lys Leu Ala Arg
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic construct D13

<400> SEQUENCE: 63

Arg Ile Met Arg Ile Leu Arg Glu Leu Lys Leu Ala Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic construct D14

<400> SEQUENCE: 64

Arg Ile Met Arg Ile Leu Arg Ile Leu Lys Gln Leu Arg
1               5                   10
```

```
<210> SEQ ID NO 65
<211> LENGTH: 13
<212> TYPE: PRT
<213> ORGANISM: Artificial Sequence
<220> FEATURE:
<223> OTHER INFORMATION: Synthetic construct D15

<400> SEQUENCE: 65

Arg Ile Met Arg Ile Leu Arg His Met Lys Leu Ala Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic construct D16

<400> SEQUENCE: 66

Arg Ile Met Arg Ser Val Arg Ile Leu Lys Leu Ala Arg
1               5                   10

<210> SEQ ID NO 67
<211> LENGTH: 13
<212> TYPE: PRT
<213> ORGANISM: Artificial Sequence
<220> FEATURE:
<223> OTHER INFORMATION: Synthetic construct D17

<400> SEQUENCE: 67

Arg Thr Met Arg Ile Leu Arg Ile Leu Lys Leu Ala Arg
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Synthetic construct D18

<400> SEQUENCE: 68

Arg Ile Met Arg Tyr Ala Arg Ile Leu Lys Leu Ala Arg
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic construct D19

<400> SEQUENCE: 69

Arg Ile Met Arg Ile Leu Arg Gln Ile Lys Leu Ala Arg
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetic construct D20

<400> SEQUENCE: 70

Arg Ile Met Arg Ile Leu Arg Ile Leu Lys Glu Val Arg
1               5                   10

<210> SEQ ID NO 71
```

```
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 71
ctgccagaag acaatgaacc                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 72
ggccattgct tccaatacac                                           20

<210> SEQ ID NO 73
<211> LENGTH: 21
<212> TYPE: DNA
<213> ORGANISM: Artificial Sequence
<220> FEATURE:
<223> OTHER INFORMATION: Synthetic construct primer

<400> SEQUENCE: 73
tggatcaaga ttagagttgg c                                         21

<210> SEQ ID NO 74
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 74
ccttgtccat tcttctgacc                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 75
gctatgctca gatcgccagt                                           20

<210> SEQ ID NO 76
<211> LENGTH: 22
<212> TYPE: DNA
<213> ORGANISM: Artificial Sequence
<220> FEATURE:
<223> OTHER INFORMATION: Synthetic construct primer

<400> SEQUENCE: 76
tctcgtaaga gtccgctagc tc                                         22

<210> SEQ ID NO 77
<211> LENGTH: 24
<212> TYPE: DNA
<213> ORGANISM: Artificial Sequence
<220> FEATURE:
<223> OTHER INFORMATION: Synthetic construct primer

<400> SEQUENCE: 77
```
tagaccaaat aacgttgaag ttga                                               24

<210> SEQ ID NO 78
<211> LENGTH: 22
<212> TYPE: DNA
<213> ORGANISM: Artificial Sequence
<220> FEATURE:
<223> OTHER INFORMATION: Synthetic construct primer

<400> SEQUENCE: 78
gattcacaaa ctgcagattc aa                                                 22

<210> SEQ ID NO 79
<211> LENGTH: 19
<212> TYPE: DNA
<213> ORGANISM: Artificial Sequence
<220> FEATURE:
<223> OTHER INFORMATION: Synthetic construct primer

<400> SEQUENCE: 79
cacctccaga tgccgtttg                                                     19

<210> SEQ ID NO 80
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 80
atgcgtggtt atcatttgcc                                                    20

<210> SEQ ID NO 81
<211> LENGTH: 20
<212> TYPE: DNA
<213> ORGANISM: Artificial Sequence
<220> FEATURE:
<223> OTHER INFORMATION: Synthetic construct primer

<400> SEQUENCE: 81
cgaaagggaa aaacaaacgc                                                    20

<210> SEQ ID NO 82
<211> LENGTH: 24
<212> TYPE: DNA
<213> ORGANISM: Artificial Sequence
<220> FEATURE:
<223> OTHER INFORMATION: Synthetic construct primer

<400> SEQUENCE: 82
tcactcactg tcataggtgt cacc                                               24

<210> SEQ ID NO 83
<211> LENGTH: 13
<212> TYPE: PRT
<213> ORGANISM: Artificial Sequence
<220> FEATURE:
<223> OTHER INFORMATION: Synthetic construct

<400> SEQUENCE: 83

Arg Ala Leu Lys Leu Ile Arg Leu Ile Arg Met Ile Arg
1               5                   10

<210> SEQ ID NO 84
<211> LENGTH: 707

```
<212> TYPE: PRT
<213> ORGANISM: Artificial Sequence
<220> FEATURE:
<223> OTHER INFORMATION: Synthetic construct

<400> SEQUENCE: 84

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
            20                  25                  30

Met Ser Glu Asp Glu Glu Asp Asp Ser Ser Gly Glu Glu Val Val Ile
        35                  40                  45

Pro Gln Ala Lys Ala Val Thr Thr Pro Gly Lys Lys Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
            85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
            115                 120                 125

Ile Pro Ala Ala Val Thr Pro Gly Lys Lys Ala Ala Lys Lys Glu Asp
    130                 135                 140

Ser Asp Glu Glu Glu Asp Asp Asp Ser Glu Glu Asp Glu Glu Asp Asp
145                 150                 155                 160

Glu Asp Glu Asp Glu Asp Glu Asp Glu Ile Glu Pro Ala Ala Met Lys
            165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Asp Ser Glu Glu
            195                 200                 205

Glu Ala Met Glu Thr Thr Pro Ala Lys Gly Lys Lys Ala Ala Lys Val
    210                 215                 220

Val Pro Val Lys Ala Lys Asn Val Ala Glu Asp Glu Asp Glu Glu Glu
225                 230                 235                 240

Asp Asp Glu Asp Glu Asp Asp Asp Asp Glu Asp Asp Glu Asp Asp
            245                 250                 255

Asp Asp Glu Asp Asp Glu Glu Glu Glu Glu Glu Glu Glu Glu Pro
            260                 265                 270

Val Lys Glu Ala Pro Gly Lys Arg Lys Lys Glu Met Ala Lys Gln Lys
    275                 280                 285

Ala Ala Pro Glu Ala Lys Lys Gln Lys Val Glu Gly Thr Glu Pro Thr
    290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
            325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
        355                 360                 365

Leu Lys Val Phe Gly Asn Glu Ile Lys Leu Glu Lys Pro Lys Gly Lys
    370                 375                 380
```

-continued

```
Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
                420                 425                 430

Tyr Ile Glu Phe Lys Thr Glu Ala Asp Ala Glu Lys Thr Phe Glu Glu
            435                 440                 445

Lys Gln Gly Thr Glu Ile Asp Gly Arg Ser Ile Ser Leu Tyr Tyr Thr
            450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
            515                 520                 525

Glu Phe Ala Ser Phe Glu Asp Ala Lys Glu Ala Leu Asn Ser Cys Asn
            530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
                580                 585                 590

Asp Gly Ser Val Arg Ala Arg Ile Val Thr Asp Arg Glu Thr Gly Ser
            595                 600                 605

Ser Lys Gly Phe Gly Phe Val Asp Phe Asn Ser Glu Glu Asp Ala Lys
            610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
                645                 650                 655

Arg Gly Gly Gly Gly Gly Arg Gly Gly Arg Gly Gly Arg Gly Gly
            660                 665                 670

Phe Gly Gly Arg Gly Arg Gly Gly Phe Gly Gly Arg Gly Gly Phe Arg
            675                 680                 685

Gly Gly Arg Gly Gly Gly Gly Asp His Lys Pro Gln Gly Lys Lys Thr
            690                 695                 700

Lys Phe Glu
705
```